US008877181B2

(12) United States Patent
Emig et al.

(10) Patent No.: US 8,877,181 B2
(45) Date of Patent: *Nov. 4, 2014

(54) AMNION-DERIVED CELLS, METHODS OF MAKING AND USES THEREOF

(71) Applicants: Charlotte Emig, Gibsonia, PA (US); Vivienne S Marshall, San Antonio, TX (US); Richard A Banas, Turtle Creek, PA (US)

(72) Inventors: Charlotte Emig, Gibsonia, PA (US); Vivienne S Marshall, San Antonio, TX (US); Richard A Banas, Turtle Creek, PA (US)

(73) Assignee: Stemnion, Inc., Pittsburgh, PA (US)

( * ) Notice: Subject to any disclaimer, the term of this patent is extended or adjusted under 35 U.S.C. 154(b) by 34 days.

This patent is subject to a terminal disclaimer.

(21) Appl. No.: 13/644,026

(22) Filed: Oct. 3, 2012

(65) Prior Publication Data

US 2013/0071363 A1 Mar. 21, 2013

Related U.S. Application Data

(62) Division of application No. 11/392,892, filed on Mar. 29, 2006.

(60) Provisional application No. 60/666,949, filed on Mar. 31, 2005, provisional application No. 60/699,257, filed on Jul. 14, 2005, provisional application No. 60/742,067, filed on Dec. 2, 2005.

(30) Foreign Application Priority Data

Mar. 29, 2006 (WO) ................ PCT/US2006/011392

(51) Int. Cl.
| | |
|---|---|
| *A01N 63/00* | (2006.01) |
| *A61K 35/50* | (2006.01) |
| *A61Q 19/00* | (2006.01) |
| *A61K 8/98* | (2006.01) |
| *C12N 5/073* | (2010.01) |
| *C12N 5/071* | (2010.01) |
| *A61K 35/12* | (2006.01) |

(52) U.S. Cl.
CPC ................ *A61K 35/50* (2013.01); *A61K 35/12* (2013.01); *A61Q 19/00* (2013.01); *A61K 8/982* (2013.01); *C12N 2501/11* (2013.01); *A12N 2502/02* (2013.01); *C12N 5/0605* (2013.01); *C12N 5/0629* (2013.01)
USPC ........................................ 424/93.7; 435/325

(58) Field of Classification Search
CPC ... A61K 2300/00; A61K 35/50; A61K 35/48; A61K 35/51; A61K 47/48784; A61K 47/48769; A61K 47/00; C12N 5/0605; C12N 5/0607
See application file for complete search history.

(56) References Cited

U.S. PATENT DOCUMENTS

| | | | |
|---|---|---|---|
| 5,855,619 A * | 1/1999 | Caplan et al. .............. | 623/23.72 |
| 2003/0087394 A1 | 5/2003 | Sharma | |
| 2003/0235563 A1 | 12/2003 | Strom | |
| 2003/0235580 A1* | 12/2003 | Zhang ........................ | 424/130.1 |
| 2004/0110287 A1 | 6/2004 | Clarke | |
| 2004/0161419 A1 | 8/2004 | Strom | |
| 2004/0229351 A1* | 11/2004 | Rodriguez et al. ............ | 435/366 |
| 2005/0019865 A1 | 1/2005 | Kihm | |
| 2005/0032209 A1 | 2/2005 | Messina | |
| 2005/0037491 A1 | 2/2005 | Mistry | |
| 2005/0054093 A1 | 3/2005 | Haas | |
| 2005/0054098 A1 | 3/2005 | Mistry | |
| 2005/0058629 A1 | 3/2005 | Harmon | |
| 2005/0058631 A1 | 3/2005 | Kihm | |
| 2005/0124003 A1 | 6/2005 | Atala | |
| 2006/0078993 A1 | 4/2006 | Phan | |
| 2006/0153816 A1 | 7/2006 | Brown | |
| 2006/0153817 A1 | 7/2006 | Kihm | |
| 2006/0153818 A1 | 7/2006 | Dhanaraj | |
| 2006/0154366 A1 | 7/2006 | Brown | |
| 2006/0154367 A1 | 7/2006 | Kihm | |
| 2006/0166361 A1 | 7/2006 | Seyda | |
| 2006/0188983 A1 | 8/2006 | Harris | |
| 2006/0223177 A1 | 10/2006 | Harris | |
| 2006/0233765 A1 | 10/2006 | Messina | |
| 2006/0233766 A1 | 10/2006 | Messina | |
| 2006/0234376 A1 | 10/2006 | Mistry | |
| 2007/0009494 A1 | 1/2007 | Mistry | |
| 2007/0014771 A1 | 1/2007 | Mistry | |
| 2007/0015278 A1 | 1/2007 | Li | |
| 2007/0036767 A1 | 2/2007 | Mistry | |

FOREIGN PATENT DOCUMENTS

| | | |
|---|---|---|
| SG | PCTSG2005000174 | 6/2005 |
| WO | WO 00/73421 A2 | 6/2000 |

OTHER PUBLICATIONS

Hammer A et al. 1997. Amnion epithelial cells, in contrast to trophoblast cells, express all classical HLA Class I molecules together with HLA-G. Am J Reprod Immunol 37: 161-171.*
Brivinlou, A.H., et al, 2003, Science 300(5621):913-6.
Miki, T., et al., 2005, Stem Cells 23:1549-1559.

(Continued)

*Primary Examiner* — Lora E Barnhart Driscoll
(74) *Attorney, Agent, or Firm* — Linda O. Palladino; Gail M. Kempler

(57) ABSTRACT

The invention is directed to substantially purified amnion-derived cell populations, compositions comprising the substantially purified amnion-derived cell populations, and to methods of creating such substantially purified amnion-derived cell populations, as well as methods of use. The invention is further directed to antibodies, in particular, monoclonal antibodies, that bind to amnion-derived cells or, alternatively, to one or more amnion-derived cell surface protein markers. The invention is further directed to methods for producing the antibodies, methods for using the antibodies, and kits comprising the antibodies.

3 Claims, 2 Drawing Sheets

(56) References Cited

OTHER PUBLICATIONS

Tylki-Szymska, A., et al., 1985, J Inherited Metabolic Disease 8(3):101-104.
Yeager, A.M., et al., 1985, Am J Med Genet 22:347-355.
Wei, J., et al., 2003, Cell Transplantation 12:545-552.
Terada, S., et al., 2000, Cell Transplantation 9:701-704.
Parolina, O., et al., 2008, Stem Cells, 26:300-311.

* cited by examiner

SEQUENCE LISTING

```
<160> NUMBER OF SEQ ID NOS: 6

<210> SEQ ID NO 1
<211> LENGTH: 9
<212> TYPE: PRT
<213> ORGANISM: Human Immunodeficiency Virus

<400> SEQUENCE: 1

Arg Lys Lys Arg Arg Gln Arg Arg Arg
1               5

<210> SEQ ID NO 2
<211> LENGTH: 9
<212> TYPE: PRT
<213> ORGANISM: Human Immunodeficiency Virus

<400> SEQUENCE: 2

Lys Lys Lys Lys Lys Lys Lys Lys Lys
1               5

<210> SEQ ID NO 3
<211> LENGTH: 9
<212> TYPE: PRT
<213> ORGANISM: Human Immunodeficiency Virus

<400> SEQUENCE: 3

Arg Arg Arg Arg Arg Arg Arg Arg Arg
1               5

<210> SEQ ID NO 4
<211> LENGTH: 281
<212> TYPE: PRT
<213> ORGANISM: Homo sapiens

<400> SEQUENCE: 4

Met Asn Gly Glu Glu Gln Tyr Tyr Ala Ala Thr Gln Leu Tyr Lys Asp
1               5                   10                  15

Pro Cys Ala Phe Gln Arg Gly Pro Ala Pro Glu Phe Ser Ala Ser Pro
                20                  25                  30

Pro Ala Cys Leu Tyr Met Gly Arg Gln Pro Pro Pro Pro Pro Pro His
            35                  40                  45

Pro Phe Pro Gly Ala Leu Gly Ala Glu Gln Gly Ser Pro Pro Asp Ile
        50                  55                  60

Ser Pro Tyr Glu Val Pro Pro Leu Ala Asp Asp Pro Ala Val Ala His
65                  70                  75                  80
```

```
Leu His His His Leu Pro Ala Gln Leu Ala Leu Pro His Pro Pro Ala
         85                  90                  95

Gly Pro Phe Pro Glu Gly Ala Glu Pro Gly Val Leu Glu Glu Asn Arg
            100                 105                 110

Val Gln Leu Pro Phe Pro Trp Met Lys Ser Thr Lys Ala His Ala Trp
        115                 120                 125

Lys Gly Gln Trp Ala Gly Gly Ala Tyr Ala Ala Glu Pro Glu Glu Asn
    130                 135                 140

Lys Arg Thr Arg Thr Ala Tyr Thr Arg Ala Gln Leu Leu Glu Leu Glu
145                 150                 155                 160

Lys Glu Phe Leu Phe Asn Lys Tyr Ile Ser Arg Pro Arg Arg Val Glu
                165                 170                 175

Leu Ala Val Met Leu Asn Leu Thr Glu Arg His Ile Lys Ile Trp Phe
            180                 185                 190

Gln Asn Arg Arg Met Lys Trp Lys Lys Glu Glu Asp Lys Lys Arg Gly
                195                 200                 205

Gly Gly Thr Ala Val Gly Gly Gly Val Ala Glu Pro Glu Gln Asp
    210                 215                 220

Cys Ala Val Thr Ser Gly Glu Glu Leu Leu Ala Leu Pro Pro Pro
225                 230                 235                 240

Pro Pro Gly Gly Ala Val Pro Pro Ala Ala Pro Val Ala Ala Arg Glu
            245                 250                 255

Gly Arg Leu Pro Pro Gly Leu Ser Ala Ser Pro Gln Pro Ser Ser Val
                260                 265                 270

Ala Pro Arg Arg Pro Gln Glu Pro Arg
        275                 280

<210> SEQ ID NO 5
<211> LENGTH: 613
<212> TYPE: DNA
<213> ORGANISM: Homo sapiens
<220> FEATURE:
<221> NAME/KEY: CDS
<222> LOCATION: (48)..(227)

<400> SEQUENCE: 5
gccctgtgtc gcccgcaggc ggcgcctacg ctgcggagcc ggaggag aac aag cgg      56
                                                  Asn Lys Arg
                                                   1 acg cgc acg gcc tac acg cgc gca cag ctg cta gag ctg gag aag gag    104
Thr Arg Thr Ala Tyr Thr Arg Ala Gln Leu Leu Glu Leu Glu Lys Glu
  5              10                  15 ttc cta ttc aac aag tac atc tca cgg ccg cgc cgg gtg gag ctg gct    152
Phe Leu Phe Asn Lys Tyr Ile Ser Arg Pro Arg Arg Val Glu Leu Ala
20              25                  30                  35 gtc atg ttg aac ttg acc gag aga cac atc aag atc tgg ttc caa aac    200
Val Met Leu Asn Leu Thr Glu Arg His Ile Lys Ile Trp Phe Gln Asn
            40                  45                  50 cgc cgc atg aag tgg aaa aag gag gag gacaagaagc gcggcggcgg          247
Arg Arg Met Lys Trp Lys Lys Glu Glu
            55                  60 gacagctgtc gggggtggcg gggtcgcgga gcctgagcag gactgcgccg tgacctccgg   307
cgaggagctt ctggcgctgc cgccgccgcc gccccccgga ggtgctgtgc cgcccgctgc   367
ccccgttgcc gcccgagagg gccgcctgcc gcctggcctt agcgcgtcgc cacagccctc   427
cagcgtcgcg cctcggcggc cgcaggaacc acgatgagag caggagctg ctcctggctg   487 aggggcttca accactcgcc gaggaggagc agagggccta ggaggacccc gggcgtggac   547
```

```
cacccgccct ggcagttgaa tggggcggca attgcggggc ccaccttaga ccgaagggga    607
aaaccc                                                               613

<210> SEQ ID NO 6
<211> LENGTH: 60
<212> TYPE: PRT
<213> ORGANISM: Homo sapiens

<400> SEQUENCE: 6

Asn Lys Arg Thr Arg Thr Ala Tyr Thr Arg Ala Gln Leu Leu Glu Leu
1               5                   10                  15

Glu Lys Glu Phe Leu Phe Asn Lys Tyr Ile Ser Arg Pro Arg Arg Val
            20                  25                  30

Glu Leu Ala Val Met Leu Asn Leu Thr Glu Arg His Ile Lys Ile Trp
        35                  40                  45

Phe Gln Asn Arg Arg Met Lys Trp Lys Lys Glu Glu
    50                  55                  60
```

AMNION-DERIVED CELLS, METHODS OF MAKING AND USES THEREOF

FIELD OF THE INVENTION

The field of the invention is directed to amnion-derived cell populations, compositions comprising the amnion-derived cell populations, expanded amnion-derived cell populations, methods of creating such amnion-derived cell populations, as well as methods of use. The field is also directed to antibodies, in particular, monoclonal antibodies, that bind to amnion-derived cells or, alternatively, to one or more amnion-derived cell surface protein markers, methods for producing the antibodies, methods for using the antibodies, and kits comprising the antibodies. The field of the invention is further directed to novel pancreatic cell compositions, methods for their production and uses thereof, and to novel cell culture factor systems.

DESCRIPTION OF RELATED ART

Preliminary evidence suggests that amnion epithelial cells isolated and placed in culture exhibit many of the characteristics necessary to define a stem cell population (Brivanlou, A. H., et al., Science, 2003. 300 (5621): p. 913-6).

Placental-derived stem cells isolated from placenta have been shown to exhibit heterogeneous protein expression of the stage-specific embryonic antigens SSEA-3 and SSEA-4, TRA 1-60, TRA 1-81, c-kit, and Thy-1 (see US2003/0235563 and US2004/0161419). These cells have also been shown to express the cell surface proteins Oct-4 and nanog, markers reportedly expressed by pluripotent stem cells. Under appropriate conditions, placental-derived stem cells have been shown to differentiate into cells with characteristics of liver cells (hepatocytes), pancreatic cells (i.e. alpha and beta cells), central nervous system cells (neurons and glia), cardiac muscle cells (cardiomyocytes) and vascular endothelial cells. Placental-derived stem cells are non-tumorigenic upon transplantation (Miki, T., et al., Stem Cells 2005; 23:1549-1559). In fact, tumors have not been observed in immuno-compromised mice following transplantation of more than 20 million placental-derived stem cells, conditions under which ES cells form non-malignant tumors known as teratomas. US2003/0235563 and US2004/0161419 disclose preliminary studies indicating that placental-derived stem cells cultured in Matrigel supplemented with 10 mM nicotinamide for 14 days express insulin and glucagon as well as the pancreatic cell markers PDX1 (faint), Pax6 and Nkx2.2.

Others have transplanted amniotic cells into volunteers and patients in an attempt to correct lysosomal storage diseases with no evidence of tumorigenicity (Tylki-Szymanska, A., et al., Journal of Inherited Metabolic Disease, 1985. 8 (3): p. 101-4; Yeager, A. M., et al., American Journal of Medical Genetics, 1985. 22 (2): p. 347-55).

Amniotic membrane is regularly transplanted as a graft for ocular surface reconstruction without subsequent tumor formation (John, T., Human amniotic membrane transplantation: past, present, and future. Opthalmol Clin North Am, 2003. March 16 (1): p. 43-65, vi). This lack of tumorigenicity is an important distinction between ES cells and placental-derived stem cells.

Results of preliminary studies with other cells are disclosed in WO 2005/017117, WO2005/0042595, US 2005/0019865, US2005/0032209, US2005/0037491, US2005/0058631, and US2005/0054093. Results of preliminary studies with these other cells indicate that they have the potential to differentiate into various cell types.

Amniotic membranes have been used clinically as wound dressing for burn patients for over 100 years to promote epithelialization, reduce pain, and prevent infection (Bose, B. (1979) Ann R Coll Surg Engl, 61:444-7; Sawhney, C. P. (1989) Burns, 15:339-42, Thomson, P. D., Parks, D. H. (1981) Ann Plast Surg, 7:354-6). US2003/0235580 describes a method of delivering therapeutic molecules to skin using amniotic epithelial cells. US2004/0057938 describes the use of a human amniotic membrane composition for prophylaxis and treatment of diseases and conditions of the eye and skin. U.S. Pat. No. 4,361,552 describes a method of treating a wound or burn, which comprises covering the surface of the wound or burn with a cross-linked amnion dressing.

US2004/0170615 describes the use of compounds expressed in fetal tissue for use in skin repair and the improvement of skin appearance.

Wei, et al, (Wei, J P, et al, (2003) Cell Transplantation 12:545-552) have shown that human amnion-isolated cells can normalize blood glucose in streptozotocin-induced diabetic mice.

BACKGROUND OF THE INVENTION

Stem Cells—Stem cells have the remarkable potential to develop into many different cell types in the body. Serving as a repair system for the body, they can theoretically divide without limit to replenish other cells throughout a person's life. When a stem cell divides, each new cell has the potential to either remain a stem cell or become another type of cell with a more specialized function, such as a muscle cell, a red blood cell, or a brain cell. Perhaps the most important potential application of human stem cells is the generation of cells and tissues that could be used for cell-based therapies. Examples of stem cell studies are provided (Tylki-Szymanska, A., et al., Journal of Inherited Metabolic Disease, 1985. 8 (3): p. 101-4; Yeager, A. M., et al., American Journal of Medical Genetics, 1985. 22 (2): p. 347-55; John, T., 2003. 16 (1): p. 43-65, vi).

Placental tissue is abundantly available as a discarded source of a type of stem cell called placental-derived stem cells. Although discarded as part of the placental membranes, lineage analysis shows that unlike other tissues of the placenta, the epithelial layer of the amnion, from which the placental-derived stem cells are isolated, is uniquely descended from the epiblast in embryonic development (FIG. 1). The epiblast contains the cells that will ultimately differentiate into the embryo and cells that will give rise to an extraembryonic tissue, the amnion. Thus far, only four cell types that have been described in the literature as being pluripotent. These are the inner cell mass (ICM) of the pre-implantation embryo, which gives rise to the epiblast, the epiblast itself, embryonic stem (ES) and embryonic germ cells (EG). Thus, identification, purification and propagation of a pluripotent cell population from discarded amnion tissue would provide an extremely valuable source of stem cells for replacement cell therapy.

With an average yield of over 200 million placental-derived stem cells per placenta, large numbers of cells are available from this source. If placental-derived stem cells were to become useful cells for transplantation medicine, they could provide a nearly inexhaustible supply of starting material in every part of the world. No other stem cell source provides such a large starting population of cells, and collection does not require an invasive or destructive procedure. Furthermore, there are no ethical, religious or social issues associated with these placental-derived stem cells as the tissue is derived from the placenta.

Another important consideration in stem cell therapies is graft tolerance. In humans, the protein expression of the cell surface marker HLA-G was originally thought to be restricted to immune-privileged sites such as placenta, as well as related cells, including some isolated from amniotic fluid, placental macrophages, and cord blood, thus implicating its role in maternal-fetal tolerance (Urosevic, M. and Dummer, R. (2002) ASHI Quarterly; 3rd Quarter 2002:106-109). Additionally, studies involving heart-graft acceptance have suggested that the protein expression of HLA-G may enhance graft tolerance (Lila, N., et al. (2000) Lancet 355:2138; Lila, N. et al. (2002) Circulation 105:1949-1954). HLA-G protein is not expressed on the surface of undifferentiated or differentiated embryonic stem cells (Drukker, M, et al. (2002) PNAS 99 (15):9864-9869). Thus, it is desirable that stems cells intended for cell-based therapies express HLA-G protein.

Wound Healing—Placental-derived cells have been shown to secrete many cytokines and growth factors including prostaglandin E2, PGES, TGF-β, EGF, IL-4, IL-8, TNF, interferons, activin A, noggin, bFGF, some neuroprotective factors, and many angiogenic factors (Koyano et al., (2002) Develop. Growth Differ. 44:103-112; Blumenstein et al. (2000) Placenta 21:210-217; Tahara et al. (1995) J. Clin. Endocrinol. Metabol. 80:138-146; Paradowska et al. (1997) Placenta 12:441-446; Denison et al. (1998) Hum. Reprod. 13:3560-3565; Keelan et al. (1998) Placenta 19:429-434; Uchida et al. (2000) J. Neurosci. Res. 62:585-590; Sun et al. (2003) J. Clin. Endocrinol. Metabol. 88(11):5564-5571; Marvin et al. (2002) Am. J. Obstet. Gynecol. 187(3):728-734). Many of these cytokines are associated with wound healing and some have been credited with contributing to scarless healing in the fetus.

Approximately 50 million surgical procedures are performed in the United States each year. An additional 50 million wounds result from traumatic injuries. Subsequent acute wound healing failure at any anatomic site results in increased morbidity and mortality. Non-limiting examples of acute wound failure include muscle, fascial and skin dehiscence, incisional hernia formation, gastrointestinal fistulization and vascular anastamotic leaks. Besides the immediate functional disability, acute wounds that fail usually go on to form disabling scars.

Incisional hernias of the abdominal wall provide an excellent paradigm to study the mechanism and outcome of acute wound healing failure. Large, prospective, well-controlled series have shown that 11-20% of over 4 million abdominal wall fascial closures fail leading to ventral incisional hernia formation. Even after repair of acute wound failure, recurrence rates remain as high as 58%. Improvements in suture material, stitch interval, stitch distance from the margin of the wound, and administration of prophylactic antibiotics to avoid infection significantly decreased the rates of clinically obvious acute wound dehiscence, but only led to small decreases in the rates of ventral hernia formation and recurrence. The introduction of tissue prostheses, typically synthetic meshes, to create a tension-free bridge or patch of the myo-fascial defect reduced first recurrence rates significantly, supporting the concept that mechanical factors predominate in the pathogenesis of recurrent hernia.

Traditional surgical teaching is that laparotomy wound failure is a rare event, with reported "fascial dehiscence" rates clustered around 0.1%. One prospective study found that the true rate of laparotomy wound failure is closer to 11%, and that the majority of these (94%) go on to form incisional hernias during the first three years after abdominal operations. This is more in line with the high incidence of incisional hernia formation. The real laparotomy wound failure rate is therefore 100 times what most surgeons think it is. In simplest terms, most incisional hernias are derived from clinically occult laparotomy wound failures, or occult fascial dehiscences. The overlying skin wound heals, concealing the underlying myofascial defect. This mechanism of early mechanical laparotomy wound failure is more consistent with modern acute wound healing science. There are no other models of acute wound healing suggesting that a successfully healed acute wound goes on to breakdown and mechanically fail at a later date. This mechanism is also unique in that it assumes that the majority of abdominal wall laparotomy wound failures occur in hosts with no clearly identifiable wound healing defect. One model of laparotomy wound failure that was developed resulted in incisional hernias. The paramedian skin flap design isolates the skin and myofascial incisions and allows one to simultaneously study midline laparotomy wound repair and paramedian dermal repair. Skin and myofascial repairs can be controlled to achieve 100% intact repairs, or 100% structural failure and wound dehiscence.

Cosmetics—

Fetal skin has much more effective repair mechanisms, and, once wounded, it is able to heal without the formation of scars. This capability does appear to require the fetal immune system, fetal serum, or amniotic fluid (Bleacher J C, et al., J Pediatr Surg 28: 1312-4, 1993); Ihara S, Motobayashi Y., Development 114: 573-82. 1992). Such abilities of fetal tissue have led to the suggested use of compounds produced by fetal tissue for regenerating and/or improving the appearance of skin (see, for example, US 2004/0170615, which is incorporated by reference in its entirety herein).

Diabetes—

Traditional insulin therapy prolongs the life of a patient with Type I diabetes but does not prevent the long-term systemic complications that arise as the disease progresses. Even the best injection/infusion regime to monitor and control systemic glucose levels within an acceptable range inevitably leads to a deterioration of tissue microvascularization resulting in the plethora of health-related complications associated with the disease. These complications can be attributed to the inability of injectable or orally administered insulin to completely substitute for the insulin secretion from a normal complement of pancreatic islets. The failure of insulin as a substitute for the pancreatic islet beta cell can largely be explained when one examines the cellular architecture of a pancreatic islet itself. Intensive inter-cellular regulation of hormone secretion, accomplished by immediate islet cell proximity, is necessary to prevent the large temporal fluctuations in blood glucose levels that are responsible for cellular damage and the ensuing complications of the disease.

Presently, transplantation of cadaver pancreas or isolation and transplantation of cadaver islets are the only alternative treatments to insulin administration that exist for patients dependent on insulin to control their diabetes. The scarcity of donor tissue reserves these alternative therapies for select patients that are unable to stabilize their blood glucose adequately using traditional insulin injection/infusion regimes.

This conundrum profiles diabetes as a prime candidate for cell-based therapies. This candidacy is made stronger by the unique quality of islets to function as self-contained, functional, glucose-sensing multicellular units Studies have also been undertaken to promote differentiation of stem cells, progenitor cells or their progeny using protein transduction domains (PTDs) such as that contained in the HIV-1 TAT protein. The HIV-1 TAT protein has been found to penetrate cells in a concentration-dependent, receptor-independent fashion. Studies have been undertaken with TAT PTDs to determine their usefulness in delivering proteins to cells (see, for example, US 2005/0048629, Wadia et al., 2004, Nature Medicine 10:310-315 and Krosl et al., 2003, Nature Medicine 9:1-10). Such proteins may be used to promote differentiation of stem cells, progenitor cells or their progeny.

BRIEF SUMMARY OF THE INVENTION

Although heterogeneous populations of placental-derived stem cells have been previously characterized using established embryonic stem cell surface protein markers such as c-kit, SSEA-3, and SSEA-4, a set of protein markers useful for characterizing and isolating a preferred substantially purified population of cells is required. This substantially purified population of cells, termed amnion-derived cells, could then be fully discriminated from other cells such as embryonic stem cells, mesenchymal stem cells or adult-derived stem cells.

Therefore, it is an object of this invention to provide such protein markers capable of characterizing and isolating amnion-derived cells from placental-derived stem cells. It is also an object of the invention to use those protein markers as antigens to make hybridoma cell lines that produce monoclonal antibodies specific for those protein markers.

Accordingly, a first aspect of the invention is a substantially purified population of amnion-derived cells that is negative for expression of the protein markers CD90 and CD117.

A second aspect of the invention is a substantially purified population of the first aspect of the invention that is further negative for expression of the protein marker CD105.

A third aspect of the invention is a substantially purified population of the first aspect of the invention that is positive for expression of the protein marker CD29.

A fourth aspect of the invention is a substantially purified population of the third aspect of the invention that is negative for expression of the protein marker CD105.

A fifth aspect of the invention is a substantially purified population of the third aspect of the invention, that is further positive for expression of at least one of the protein markers selected from the group consisting of CD9, CD10, CD26, CD71, CD166, CD227, EGF-R, SSEA-4, and HLA-G.

A sixth aspect of the invention is a substantially purified population of the fourth aspect of the invention, that is further positive for expression of at least one of the protein markers selected from the group consisting of CD9, CD10, CD26, CD71, CD166, CD227, EGF-R, SSEA-4, and HLA-G.

A seventh aspect of the invention is a substantially purified population of the second aspect of the invention that is further negative for the expression of at least one of the protein markers selected from the group consisting of CD140b, telomerase, CD34, CD44, and CD45.

An eighth aspect of the invention is a substantially purified population of the fourth aspect of the invention that is further negative for the expression of at least one of the protein markers selected from the group consisting of CD140b, telomerase, CD34, CD44, and CD45.

A ninth aspect of the invention is a substantially purified population of the sixth aspect of the invention that is further negative for the expression of at least one of the protein markers selected from the group consisting of CD140b, telomerase, CD34, CD44, and CD45.

A tenth aspect of the invention is a population of amnion-derived cells of aspects one through nine of the invention, which is a composition. In a preferred embodiment, the composition is a pharmaceutical composition.

An eleventh aspect of the invention is a method of obtaining the substantially purified population of amnion-derived cells of the first aspect of the invention, comprising: a) providing a population of amnion-derived cells; b) contacting the population of amnion-derived cells with anti-CD90 and anti-CD117 antibodies; and c) separating the amnion-derived cells that bind to the antibodies from the cells that do not bind to the antibodies such that the substantially purified population of amnion-derived cells of the first aspect of the invention that do not bind to the antibodies is obtained.

A twelfth aspect of the invention is a method of obtaining the substantially purified population of amnion-derived cells of the second aspect of the invention, comprising: a) providing a population of amnion-derived cells; b) contacting the cells with anti-CD90, anti-CD117, and anti-CD105 antibodies; and c) separating the cells that bind to the antibodies from the cells that do not bind to the antibodies such that the substantially purified population of amnion-derived cells of the second aspect of the invention that do not bind to the antibodies is obtained.

A thirteenth aspect of the invention is a method of obtaining the substantially purified population of amnion-derived cells of the seventh aspect of the invention, comprising: a) providing a population of amnion-derived cells; b) contacting the cells with (i) anti-CD90, anti-CD117, and anti-CD105 antibodies and (ii) with at least one antibody selected from the group consisting of anti-CD140b, anti-CD34, anti-CD44, and anti-CD45 antibodies; and c) separating the cells that bind to the antibodies of (i) from the cells that do not bind to the antibodies of (i) and separating the cells that bind to the antibodies of (ii) from the cells that do not bind to the antibodies of (ii); and such that the substantially purified population of amnion-derived cells of the seventh aspect of the invention that do not bind to the antibodies of (i) and (ii) is obtained.

A fourteenth aspect of the invention is a method of obtaining the substantially purified population of amnion-derived cells of the third aspect of the invention, comprising: a) providing a population of amnion-derived cells; b) contacting the cells with (i) anti-CD90 and anti-CD117 antibodies and (ii) with an anti-CD29 antibody; and c) separating the cells that do not bind to the antibodies of (i) from the cells that do bind to the antibody of (i) and separating the cells that do not bind to the antibodies of (ii) from the cells that do bind to the antibody of (ii) such that the substantially purified population of amnion-derived cells of the third aspect of the invention that do not bind to the antibodies of (i) and do bind to the antibody of (ii) is obtained.

A fifteenth aspect of the invention is a method of obtaining the substantially purified population of amnion-derived cells of the fourth aspect of the invention, comprising: a) providing a population of amnion-derived cells; b) contacting the cells with (i) anti-CD90, anti-CD117 and anti-CD105 antibodies and (ii) with an anti-CD29 antibody; and c) separating the cells that do not bind to the antibodies of (i) from the cells that do bind to the antibodies of (i) and separating the cells that do not bind to the antibody of (ii) from the cells that do bind to the antibody of (ii) such that the substantially purified population of amnion-derived cells of the fourth aspect of the invention that do not bind to the antibodies of (i) and do bind to the antibody of (ii) is obtained.

A sixteenth aspect of the invention is a method of obtaining the substantially purified population of amnion-derived cells of the fifth aspect of the invention, comprising: a) providing a population of amnion-derived cells; b) contacting the cells with (i) anti-CD90, anti-CD117 antibodies and (ii) anti-CD29 antibodies and (iii) with one or more antibodies selected from the group consisting of anti-CD9, anti-CD10, anti-CD26, anti-CD71, anti-CD166, anti-CD227, anti-EGF-R, anti-SSEA-4, and anti-HLA-G antibodies; and c) separating the cells that do not bind to the antibody of (i) from the cells that do bind to the antibodies of (i) and separating the cells that do not bind to the antibody of (ii) from the cells that do bind to the antibody of (ii) and separating the cells that do not bind to the antibodies of (iii) from the cells that do bind to the antibodies of (iii) such that the substantially purified population of amnion-derived cells of the fifth aspect of the invention that do not bind to antibodies of (i), do bind to antibody of (ii) and do bind to antibodies of (iii) is obtained.

A seventeenth aspect of the invention is a method of obtaining the substantially purified population of amnion-derived cells of the sixth aspect of the invention, comprising: a) providing a population of amnion-derived cells; b) contacting the cells with (i) anti-CD90, anti-CD117, and anti-CD105 antibodies and (ii) and anti-CD29 antibodies and (iii) with one or more antibodies selected from the group consisting of anti-CD9, anti-CD10, anti-CD26, anti-CD71, anti-CD166, anti-CD227, anti-EGF-R, anti-SSEA-4, and anti-HLA-G antibodies; and c) separating the cells that do not bind to the antibody of (i) from the cells that do bind to the antibodies of (i) and separating the cells that do not bind to the antibody of (ii) from the cells that do bind to the antibody of (ii) and separating the cells that do not bind to the antibodies of (iii) from the cells that do bind to the antibodies of (iii) such that the substantially purified population of amnion-derived cells of the sixth aspect of the invention that do not bind to antibodies of (i), do bind to antibody of (ii) and do bind to antibodies of (iii) is obtained.

An eighteenth aspect of the invention is a method of obtaining the substantially purified population of amnion-derived cells of the eighth aspect of the invention, comprising: a) providing a population of amnion-derived cells; b) contacting the cells with (i) anti-CD90, anti-CD117, and anti-CD105 antibodies and (ii) and anti-CD29 antibodies and (iii) with one or more antibodies selected from the group consisting of anti-CD140b, anti-CD34, anti-CD44, and anti-CD45 antibodies; and c) separating the cells that do not bind to the antibody of (i) from the cells that do bind to the antibodies of (i) and separating the cells that do not bind to the antibody of (ii) from the cells that do bind to the antibody of (ii) and separating the cells that do not bind to the antibodies of (iii) from the cells that do bind to the antibodies of (iii) such that the substantially purified population of amnion-derived cells of the eighth aspect of the invention that do not bind to antibodies of (i), do bind to antibody of (ii) and do not bind to antibodies of (iii) is obtained.

A nineteenth aspect of the invention is a method of obtaining the substantially purified population of amnion-derived cells of the ninth aspect of the invention, comprising: a) providing a population of amnion-derived cells; b) contacting the cells with (i) anti-CD90, anti-CD117, and anti-CD105 antibodies and (ii) and anti-CD29 antibodies and (iii) one or more antibodies selected from the group consisting of anti-CD140b, anti-CD34, anti-CD44, and anti-CD45 antibodies and (iv) one or more antibodies selected from the group consisting of anti-CD9, anti-CD10, anti-CD26, anti-CD71, anti-CD166, anti-CD227, anti-EGF-R, anti-SSEA-4, and anti-HLA-G antibodies; and c) separating the cells that do not bind to the antibody of (i) from the cells that do bind to the antibodies of (i) and separating the cells that do not bind to the antibody of (ii) from the cells that do bind to the antibody of (ii) and separating the cells that do not bind to the antibodies of (iii) from the cells that do bind to the antibodies of (iii) and separating the cells from that do bind to the antibody of (iv) from the cells that do not bind to the antibodies of (iv) such that the substantially purified population of amnion-derived cells of the ninth aspect of the invention that do not bind to antibodies of (i), do bind to antibody of (ii), do not bind to antibodies of (iii) and do bind to the antibodies of (iv) is obtained.

A twentieth aspect of the invention is a method of obtaining a substantially purified population of amnion-derived cells, comprising: a) providing a population of amnion-derived cells; b) contacting the cells with one or more antibodies selected from the group consisting of anti-CD105, anti-CD90, anti-CD117, anti-CD140b, anti-CD34, anti-CD44, and anti-CD45 antibodies; and one or more antibodies selected from the group consisting of anti-CD29, anti-CD9, anti-CD10, anti-CD26, anti-CD71, anti-CD166, anti-CD227, anti-EGF-R, anti-SSEA-4, and anti-HLA-G antibodies; and c) separating the cells that do not bind to the antibodies of (i) from the cells that do bind to the antibody of (i) and separating the cells that do not bind to the antibodies of (ii) from the cells that do bind to the antibody of (ii) such that a substantially purified population of amnion-derived cells that do not bind to the antibodies of (i) and do bind to the antibody of (ii) is obtained.

A twenty-first aspect of the invention is the method of aspects 11 through 20, wherein the cells are separated by FACS sorting.

A twenty-second aspect of the invention is one in which the antibodies of aspects 11 through 20 are monoclonal antibodies, fully human antibodies, humanized antibodies, chimeric antibodies, a scfv, or a fragment or derivative of any one of the aforementioned antibodies.

In addition to aspects 1 through 22 of the invention, additional aspects provide for expanded and/or clustered amnion-derived cells and populations, which provide several advantages over previously described placental-derived cell compositions as well as embryonic stem cells compositions.

Accordingly, a twenty-third aspect of the invention is the amnion-derived cells of the first aspect of the invention, which are an expanded amnion-derived cell composition. In a preferred embodiment, the composition of aspect twenty three is animal-free. In another preferred embodiment the composition is a clustered amnion-derived cell composition.

A twenty-fourth aspect of the invention is a composition comprising conditioned medium obtained from the expanded amnion-derived cell composition of the twenty-third aspect of the invention.

A twenty-fifth aspect of the invention is a composition comprising cell lysate obtained from the amnion-derived cell composition of the twenty-third aspect of the invention.

A twenty-sixth aspect of the invention is the expanded amnion-derived cell composition of the twenty-third aspect having a concentration of at least $500 \times 10^6$ amnion-derived cells/g of starting amnion.

A twenty-seventh aspect of the invention is a method of creating a hepatocyte comprising differentiating, in vitro or in vivo, an amnion-derived cell population of the first aspect of the invention.

A twenty-eighth aspect of the invention is a hepatocyte created by the method of the twenty-seventh aspect of the invention.

A twenty-ninth aspect of the invention is a liver assist device comprising an amnion-derived cell composition of the twenty-seventh aspect of the invention.

A thirtieth aspect of the invention is a method of creating a cardiomyocyte comprising differentiating, in vitro or in vivo, an amnion-derived cell population of the first aspect of the invention.

A thirty-first aspect of the invention is a cardiomyocyte created by the method of the thirtieth aspect of the invention.

A thirty-second aspect of the invention is a method for promoting accelerated wound healing in an injured patient in need thereof comprising administering to the patient one or more compositions of placental-derived cells. In a preferred embodiment the composition of placental-derived cells is an expanded amnion-derived cell composition. In another preferred embodiment of the method the composition is administered in a scaffold or matrix. In a specific, preferred embodiment, the scaffold or matrix is amniotic tissue. In another preferred embodiment, the wound is selected from the group consisting of mechanical, thermal, acute, chronic, infected, and sterile wounds. And in yet another preferred embodiment the injured patient is a human.

A thirty-third aspect of the invention is a cosmetic preparation comprising one or more compositions of placental-derived cells. In a preferred embodiment, the composition of placental-derived cells is an expanded amnion-derived cell composition.

A thirty-fourth aspect of the invention is a method for treating hearing loss in a patient in need thereof comprising administering to the patient one or more compositions of placental-derived cells. In a preferred embodiment, the composition of placental-derived cells is an expanded amnion-derived cell composition.

A thirty-fifth aspect of the invention is a method of proliferating embryonic stem cells comprising using the amnion-derived cells of the first aspect as a feeder layer. One preferred embodiment of this aspect is one which is free of animal products.

In addition to aspects 23 through 35 of the invention, the invention also contemplates compositions comprising differentiated amnion-derived cell populations, method for identifying such populations, methods of making such populations, and methods of using them.

Accordingly, a thirty-sixth aspect of the invention is the population of the first aspect of the invention wherein the cells express a pancreatic progenitor cell marker protein. In a preferred embodiment, the progenitor cell marker is PDX1 protein. In another preferred embodiment, the PDX1 protein is expressed in the nucleus.

A thirty-seventh aspect of the invention is the population of cells of the thirty-sixth aspect further optionally expressing any one or more of the protein markers selected from the group consisting of Foxa2, p48, Hblx9 and Neurogenin 3 (Ngn3). In a preferred embodiment, the cells further optionally express any one or more of the protein markers selected from the group consisting of NKx2.2, Nkx6.1, insulin and islet-1.

In a thirty-eighth aspect of the invention is a population of cells of the thirty-sixth aspect, wherein the cells are differentiated pancreatic progenitor cells. In a preferred embodiment, the differentiated progenitor cells express any one or more of the protein markers selected from the group consisting of PDX1, insulin, C-peptide, somatostatin, pancreatic polypeptide, and glucagon. In another preferred embodiment the differentiated pancreatic progenitor cells are islet-like cells. In a specific, preferred embodiment the islet-like cells are alpha, beta, delta or phi cells and in a most preferred embodiment the islet-like cells are functional islet-like cells. In another preferred embodiment the functionality of the islet-like cells is incremental glucose-dependent insulin secretion.

A thirty-ninth aspect of the invention is an islet comprising the population of cells of the thirty-sixth and thirty-eighth aspects.

A fortieth aspect of the invention is a tissue comprising the population of the thirty-sixth and thirty-eighth aspects.

A forty-first aspect of the invention is the population of the thirty-sixth aspect wherein the cells form spheroids. In a preferred embodiment the spheroids form buds. In another preferred embodiment the buds express PDX1 protein and in a most preferred embodiment the PDX1 protein is expressed in the nucleus.

A forty-second aspect of the invention is the population of the thirty-sixth aspect of the invention which comprises one or more mammalian embryonic islet progenitor cells. In a preferred embodiment of this aspect, the mammalian embryonic islet progenitor cells are human cells.

A forty-third aspect of the invention is the population of the thirty-sixth aspect wherein the cells express a heterologous protein. In one embodiment the heterologous protein is a TAT fusion protein. In specific embodiments the TAT fusion protein is TAT-PDX1, TAT-Hblx9, TAT-p48, TA-Ngn3 or TAT-Foxa2. In another preferred embodiment the heterologous protein is a therapeutic protein of interest.

A forty-fourth aspect of the invention is the population of the thirty-sixth aspect wherein the cells have the identifying characteristics of endoderm. In a preferred embodiment the identifying characteristics of endoderm are expression of HNF1α, HNF1β, HNF4α, HNF6, Foxa2 and PDX1 proteins. In another preferred embodiment the cells further optionally express any one or more of the protein markers Sox17, Cerberus, Hesx1, LeftyA, Otx1 or Otx2.

A forty-fifth aspect of the invention is a composition comprising one or more nuclei isolated from pancreatic progenitor cells of the thirty eighth aspect, wherein the cells express PDX1 protein in the nucleus and/or express Nkx2.2, Nkx6.1, insulin and islet-1 protein and/or have the identifying characteristics of endoderm. In a preferred embodiment of this aspect the identifying characteristics of endoderm are protein expression of HNF1α, HNF1β, HNF4α, HNF6, Foxa2 and PDX1. In another preferred embodiment the cells further optionally express any one or more of the protein markers Sox17, Cerberus, Hesx1, LeftyA, Otx1 or Otx2.

A forty-sixth aspect of the invention is a pharmaceutical composition comprising an effective amount of the population of the first, thirteenth, thirty-six and thirty-eighth aspects of the invention and a carrier.

A forty-seventh aspect of the invention is a substantially purified composition comprising one or more undifferentiated cells wherein the cells express a pancreatic progenitor cell marker protein. In a preferred embodiment the cells are embryonic stem cells. In another preferred embodiment the cells are adult stem cells. In yet another preferred embodiment the cells are hematopoietic stem cells and in still another preferred embodiment the cells are mesenchymal stem cells.

A forty-eighth aspect of the invention is the composition of the forty-seventh aspect which is transplanted into a subject. In a preferred embodiment the subject is a human subject.

A forty-ninth aspect of the invention is an in vivo method for inducing differentiation of resident pancreatic cells into islet cells comprising a) introducing factors into the pancreas of a subject; and b) allowing the introduced factors to prime the resident pancreatic cells such that the cells are induced to differentiate into islet progenitor cells and/or islet cells. In a preferred embodiment the islet cells are alpha, beta, delta or phi cells.

A fiftieth aspect of the invention is an in vivo method for promoting the generation of islet cells in a subject comprising a) transplanting amnion-derived cells into the pancreas of the subject; (b) introducing factors into the pancreas of the subject; and c) allowing the introduced factors to promote generation of islet progenitor cells or islet cells from the transplanted amnion-derived cells. In a preferred embodiment the amnion-derived cells are undifferentiated amnion-derived cells or partially differentiated amnion-derived cells. In another embodiment the cells are transplanted subcutaneously, into liver, mammary gland, kidney capsule, spleen or any other site in which the cells are able to engraft.

A fifty-first aspect of the invention is an in vivo method for promoting the differentiation of amnion-derived cells into pancreatic cells comprising (a) co-culturing the amnion-derived cells with differentiating embryonic pancreatic or non-pancreatic tissue; and (b) transplanting the co-cultures into the pancreas of a subject. In a preferred embodiment the non-pancreatic tissue is selected from the group consisting of epithelium, mesenchyme, islets, ducts, and exocrine tissue. In another preferred embodiment the amnion-derived cells are undifferentiated amnion-derived cells or partially differentiated amnion-derived cells. In another embodiment the cells are transplanted subcutaneously, into liver, mammary gland, kidney capsule, spleen or any other site in which the cells are able to engraft.

A fifty-second aspect of the invention is an in vivo method for promoting the differentiation of amnion-derived cells into pancreatic cells comprising (a) co-culturing the amnion-derived cells with differentiating or pre-differentiating non-embryonic heterologous or autologous tissue; and (b) transplanting the co-cultures into the pancreas of a subject. In a preferred embodiment the amnion-derived cells are undifferentiated amnion-derived cells or partially differentiated amnion-derived cells. In another embodiment the cells are transplanted subcutaneously, into liver, mammary gland, kidney capsule, spleen or any other site in which the cells are able to engraft.

A fifty-third aspect of the invention is an in vivo method for promoting the differentiation of amnion-derived cells into pancreatic cells comprising (a) introducing factors to the amnion-derived cells in vitro; and (b) subsequently transplanting the amnion-derived cells into the pancreas of a subject. In a preferred embodiment the amnion-derived cells are undifferentiated amnion-derived cells or partially differentiated amnion-derived cells. In another embodiment the cells are transplanted subcutaneously, into liver, mammary gland, kidney capsule, spleen or any other site in which the cells are able to engraft.

A fifty-fourth aspect of the invention is a cell culture system comprising a cell culture medium comprising a SHh antagonist and the population of the first aspect or the thirty-sixth aspect of the invention. In a preferred embodiment the cell culture system further comprises one or more mammalian embryonic islet progenitor cells. In another preferred embodiment the SHh antagonist is cyclopamine or jervine. In a specific preferred embodiment the cyclopamine is at a concentration of 10 µM. In another preferred embodiment the cell culture system further comprises a solid surface. In a specific embodiment the solid is extracellular matrix and in another specific embodiment the extracellular matrix is composed of one or more of the substances selected from the group consisting of Matrigel, fibronectin, superfibronectin, laminin, collagen, heparin sulfate proteoglycan and naturally occurring acellular biological substances. In another embodiment the solid surface forms a scaffold and in a specific embodiment the scaffold is a fiber, gel, fabric, sponge-like sheet or complex three-dimensional form containing pores and channels.

A fifty-fifth aspect of the invention is a cell culture system comprising a cell culture medium comprising a TAT fusion peptide and the population of the first aspect or the thirty-sixth aspect of the invention. In preferred embodiments the TAT fusion protein is TAT-PDX1, TAT-Hblx9, TAT-Ngn3, TAT-p48, or TAT-Foxa2. In a preferred embodiment, the cell culture system further comprises a SHh antagonist. In another preferred embodiment the cell culture system further comprises one or more mammalian embryonic islet progenitor cells. In another preferred embodiment the SHh antagonist is cyclopamine or jervine. In a specific preferred embodiment the cyclopamine is at a concentration of 10 µM. In another preferred embodiment the cell culture system further comprises a solid surface. In a specific embodiment the solid is extracellular matrix and in another specific embodiment the extracellular matrix is composed of one or more of the substances selected from the group consisting of Matrigel, fibronectin, superfibronectin, laminin, collagen, heparin sulfate proteoglycan and naturally occurring acellular biological substances. In another embodiment the solid surface forms a scaffold and in a specific embodiment the scaffold is a fiber, gel, fabric, sponge-like sheet or complex three-dimensional form containing pores and channels.

A fifty-sixth aspect of the invention is a method for obtaining a pancreatic progenitor cell comprising culturing an undifferentiated cell in the culture system of the fifty-fifth aspect of the invention.

A fifty-seventh aspect of the invention is a composition comprising a donor cell comprising a nucleus isolated from the amnion-derived cell of the first aspect of the invention. In a preferred embodiment the amnion derived cell is an expanded amnion-derived cell of the twenty-third aspect of the invention. In another preferred embodiment amnion-derived cell is a pancreatic progenitor cell of aspect thirty-six of the invention. In another preferred embodiment the amnion-derived cell is an alpha, beta, delta or phi cell. In another preferred embodiment the recipient cell is a mammalian cell and in a specific embodiment the mammalian cell is selected from the group consisting of germ cells, oocytes and sperm.

DEFINITIONS

The amino acid residues described herein are preferred to be in the "L" isomeric form. However, residues in the "D" isomeric form can be substituted for any L-amino acid residue, as long as the desired function is retained by the polypeptide. NH2 refers to the free amino group present at the amino terminus of a polypeptide. COOH refers to the free carboxy group present at the carboxy terminus of a polypeptide.

As defined herein "isolated" refers to material removed from its original environment and is thus altered "by the hand of man" from its natural state.

As defined herein, a "gene" is the segment of DNA involved in producing a polypeptide chain; it includes regions preceding and following the coding region, as well as intervening sequences (introns) between individual coding segments (exons).

As used herein, the term "protein marker" means any protein molecule characteristic of the plasma membrane of a cell or in some cases of a specific cell type.

As used herein, "enriched" means to selectively concentrate or to increase the amount of one or more materials by elimination of the unwanted materials or selection and separation of desirable materials from a mixture (i.e. separate cells with specific cell markers from a heterogenous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of marker As used herein, the term "monoclonal antibody library" means a collection of at least one monoclonal antibody useful for identifying unique amnion-derived cells protein markers or generating substantially purified populations of amnion-derived cells. As defined herein, "specific for" means that the antibody(ies) specifically bind to amnion-derived cells, but not embryonic stem cells, mesenchymal stem cells or adult-derived stem cells.

The term "placenta" as used herein means both preterm and term placenta.

As used herein, the term "totipotent cells" shall have the following meaning. In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning. Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

"Amnion-derived cells" are a population of cells that are derived from the amnion of the placenta. Amnion-derived cells grow without feeder layers, do not express the protein telomerase and are non-tumorigenic. Amnion-derived cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated amnion-derived cells will not react with antibodies to the stem/progenitor cell markers c-kit and Thy-1. Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172: 493-500). However, the methods used herein provide improved compositions and populations of cells.

The term "composition of placental-derived cells" as used herein includes the cells and compositions described in this application and in US2003/0235563, US2004/0161419, US2005/0124003, U.S. Provisional Application Nos. 60/666, 949, 60/699,257, 60/742,067 and U.S. application Ser. No. 11/333,849, the contents of which are incorporated herein by reference in their entirety.

By the term "animal-free" when referring to compositions, growth conditions, culture media, etc. described herein, is meant that no animal-derived materials, such as animal-derived serum, other than human materials, such as native or recombinantly produced human proteins, are used in the preparation, growth, culturing, expansion, or formulation of the composition or process.

By the term "expanded", in reference to amnion-derived cell compositions, means that the amnion-derived cell population constitutes a significantly higher concentration of multipotent cells than is obtained using previous methods. The level of multipotent cells per gram of amniotic tissue in expanded compositions is at least 50 and up to 150 fold higher than the number of cells in the primary culture after 5 passages, as compared to about a 20 fold increase in such cells using previous methods. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the proportion of the amnion-derived cells. As used herein "passage" or "passaging" refers to subculturing of cells. For example, cells isolated from the amnion are referred to as primary cells. Such cells are expanded in culture by being grown in the growth medium described herein. When such primary cells are subcultured, each round of subculturing is referred to as a passage. As used herein, "primary culture" means the freshly isolated amnion-derived cell population.

As used herein a "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, and granules. The medium containing the cellular factors is the conditioned medium. Examples of methods of preparing conditioned media are described in U.S. Pat. No. 6,372,494 which is incorporated by reference in its entirety herein. As used herein, conditioned medium also refers to components, such as proteins, that are recovered and/or purified from conditioned medium or from amnion-derived cells.

The term "lysate" as used herein refers to the composition obtained when the amnion-derived cell are lysed and the cellular debris (e.g., cellular membranes) is removed. This may be achieved by mechanical means, by freezing and thawing, by use of detergents, such as EDTA, or by enzymatic digestion using, for example, hyaluronidase, dispase, proteases, and nucleases.

As used herein, the term "substrate" means a defined coating on a surface that cells attach to, grown on, and/or migrate on. As used herein, the term "matrix" means a substance that cells grow in or on that may or may not be defined in its components. The matrix includes both biological and non-biological substances. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions.

The term "transplantation" refers to the administration of a composition either in an undifferentiated, partially differentiated, or fully differentiated form into a human or other animal.

As used herein, the term "pharmaceutically acceptable" means that the components, in addition to the therapeutic agent, comprising the formulation, are suitable for administration to the patient being treated in accordance with the present invention.

The term "liver disease" as used herein includes but is not limited to cirrhosis of the liver, metabolic diseases of the liver, such as alpha 1-antitrypsin deficiency and ornithine transcarbamylase (OTC), alcohol-induced hepatitis, chronic hepatitis, primary sclerosing cholangitis, alpha 1-antitrypsin deficiency and liver cancer. As used herein, the term "pancreatic disease" may include but is not limited to pancreatic cancer, insulin-deficiency disorder such as Insulin-dependent (Type 1) diabetes mellitus (IDDM) and Non-insulin-dependent (Type 2) diabetes mellitus (NIDDM), hepatitis C infection, exocrine and endocrine pancreatic diseases. As used herein, the term "neurological disease" refers to a disease or condition associated with any defects in the entire integrated system of nervous tissue in the body: the cerebral cortex, cerebellum, thalamus, hypothalamus, midbrain, pons, medulla, brainstem, spinal cord, basal ganglia and peripheral nervous system. As used herein, the term "vascular disease" refers to a disease of the human vascular system. As used herein, the term "cardiac disease" or "cardiac dysfunction" refers to diseases that result from any impairment in the heart's pumping function. The term "cardiomyopathy" refers to any disease or dysfunction of the myocardium (heart muscle) in which the heart is abnormally enlarged, thickened and/or stiffened.

As used herein, the term "hepatocytes" refers to cells that have characteristics of epithelial cells obtained from liver. As used herein, the term "pancreatic cell" is used to refer to cells that produce glucagon, insulin, somatostatin, and/or pancreatic polypeptide (PP). Preferred pancreatic cells are positive for pancreatic cell-specific markers, such as homeobox transcription factor Nkx-2.2, glucagon, paired box gene 6 (Pax6), pancreatic duodenal homeobox 1 (PDX1), and insulin. As used herein, the term "vascular endothelial cell" refers to an endothelial cell that exhibits essential physiological functions characteristic of vascular endothelial cells including modulation of vasoreactivity and provision of a semi-permeable barrier to plasma fluid and protein. As used herein, the term "cardiomyocyte" refers to a cardiac muscle cell that may spontaneously beat or may exhibit calcium transients (flux in intracellular calcium concentrations measurable by calcium imaging). As used herein, the term "neural cells" refer to cells that exhibit essential functions of neurons, and glial cells (astrocytes and oligodendrocytes).

As used herein, the term "tissue" refers to an aggregation of similarly specialized cells united in the performance of a particular function.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

As used herein, "pancreas" refers generally to a large, elongated, racemose gland situated transversely behind the stomach, between the spleen and duodenum. The pancreatic exocrine function, e.g., external secretion, provides a source of digestive enzymes. These cells synthesize and secrete digestive enzymes such as trypsinogen, chymotrypsinogen, carboxypeptidase, ribonuclease, deoxyribonuclease, triacylglycerol lipase, phospholipase A2 elastase, and amylase. The endocrine portion of the pancreas contains the islets of Langerhans. The islets of Langerhans appear as rounded spheroids of cells embedded within the exocrine pancreas. Four different types of cells—alpha, beta, delta, and phi—have been identified in the islets. The alpha cells constitute about 20% of the cells found in pancreatic islets and produce the hormone glucagon. Glucagon acts on several tissues to make energy available in the intervals between feeding. In the liver, glucagon causes breakdown of glycogen and promotes gluconeogenesis from amino acid precursors. The delta cells produce somatostatin which acts in the pancreas to inhibit glucagon release and to decrease pancreatic exocrine secretion. The hormone pancreatic polypeptide (PP) is produced in the phi cells. This hormone inhibits pancreatic exocrine secretion of bicarbonate and enzymes, causes relaxation of the gallbladder, and decreases bile secretion. The most abundant cell in the islets, constituting 60-80% of the cells, is the beta cell, which produces insulin. Insulin is known to cause the storage of excess nutrients arising during and shortly after feeding. The major target organs for insulin are the liver, muscle, and fat-organs specialized for storage of energy. The term "pancreatic duct" as used herein includes the accessory pancreatic duct, dorsal pancreatic duct, main pancreatic duct and ventral pancreatic duct, interlobular pancreatic duct, and interlobular pancreatic duct.

As used herein, the term "clustered amnion-derived cell compositions" refers to amnion-derived cell compositions wherein at least 50% and up to about 95% of the cells form clusters.

"Pancreatic progenitor cell" as defined herein is a cell which can differentiate into a cell of pancreatic lineage, e.g., a cell which can produce a hormone or enzyme normally produced by a pancreatic cell. For instance, a pancreatic progenitor cell may be caused to differentiate, at least partially, into alpha, beta, delta, or phi islet cells, or a cell of exocrine fate. In accordance with the method of the invention, the pancreatic progenitor cells of the invention can be cultured prior to administration to a subject under conditions which promote cell proliferation and/or differentiation. These conditions include but are not limited to culturing the cells to allow proliferation in vitro at which time the cells may form pseudo islet-like spheroids and secrete insulin, glucagon, and somatostatin. The term "islet-like cell" as used herein means having some but not necessarily all of the characteristics of one of the cell types ($\alpha$, $\beta$, $\gamma$ or $\delta$) present in a mature pancreatic islet. The islet-like cell will express only one of the following pancreatic endocrine cell hormones: Insulin, glucagon, Somatostatin, Pancreatic Polypeptide. The term "islet-like structures" as defined herein are structures containing islet-like cells. Islet-like structures refers to the spheroids of cells derived from the methods of the invention which take on both the appearance of pancreatic alpha, beta, delta or phi cells, as well as their function. Their coordinated function includes the ability to respond to glucose.

As used herein, the term "spheroid" or "spheroids" means multicellular clusters in suspension cultures. As used herein the term "bud" or "buds" means the segregation of a subset of cells in a spheroid into a group on the surface of the spheroid.

As used herein "germ cells" means embryonic germ cells, adult germ cells and the cells that they give rise to (i.e. oocyte and sperm).

As used herein, "cloning" refers to producing an animal that develops from the combination of an oocyte and the genetic information contain within the nucleus or the nucleic acid sequence of another animal, the animal being cloned. The resulting oocyte having the donor genome is referred to herein as a "nuclear transfer cell." The cloned animal has substantially the same or identical genetic information as that of the animal being cloned. "Cloning" may also refer to cloning a cell, which includes producing an oocyte containing genetic information from the nucleus or the nucleic acid sequence of another animal. Again, the resulting oocyte having the donor genome is referred to herein as a "nuclear transfer cell."

The term "transplantation" as used herein refers to the administration of a composition comprising cells that are either in an undifferentiated, partially differentiated, or fully differentiated form into a human or other animal.

"Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; or (c) relieving the disease or condition, i.e., causing regression of the disease or condition. The population of subjects treated by the methods of the invention includes subjects suffering from the undesirable condition or disease, as well as subjects at risk for development of the condition or disease.

A "wound" is any disruption, from whatever cause, of normal anatomy including but not limited to traumatic injuries such as mechanical, thermal, and incisional injuries; elective injuries such as surgery and resultant incisional hernias; acute wounds, chronic wounds, infected wounds, and sterile wounds, as well as wounds associated with disease states (i.e. ulcers caused by diabetic neuropathy). A wound is dynamic and the process of healing is a continuum requiring a series of integrated and interrelated cellular processes that begin at the time of wounding and proceed beyond initial wound closure through arrival at a stable scar. These cellular processes are mediated or modulated by humoral substances including but not limited to cytokines, lymphokines, growth factors, and hormones. In accordance with the subject invention, "wound healing" refers to improving, by some form of intervention, the natural cellular processes and humoral substances such that healing is faster, and/or the resulting healed area has less scaring and/or the wounded area possesses tissue tensile strength that is closer to that of uninjured tissue.

Definitions of additional terms are set forth in the table of abbreviations below.

TABLE 1

| Abbreviation | Description |
| --- | --- |
| A1AT | Alpha-1 Antitrypsin |
| CD34 | Clustered Differentiation Antigen 34 |
| c-Kit | Stem Cell Factor Receptor |
| C/EBPα | CCAAT/enhancer binding protein-alpha |
| CNP | Natriuretic Peptide C |
| CYP | Cytochrome |
| ELISA | Enzyme-Linked Immunosorbent Assay |
| EROD | Ethoxyresorufin-o-deethylase |
| EG | Embryonic Germ |
| ES | Embryonic Stem |
| FCS | Fetal Calf Serum |
| FGF | Fibroblast growth factor |
| FACS | Fluorescence Activated Cell Sorting |
| Foxa2 | Forkhead box protein A2; Hepatocyte nuclear factor 3-beta |
| GABA | Gamma-amino butyric acid |
| GAD | Glutamic acid decarboxylase |
| HB9 | Homeobox Protein-HB9 |
| HNF4α | Hepatocyte nuclear factor-4α |
| HNF6 | Hepatocyte nuclear factor-6 |
| ICC | Immunocytochemistry |
| IHC | Immunohistochemistry |
| ICM | Inner Cell Mass |
| IE | Islet equivalent |
| LeftyA | Endometrial bleeding associated factor preprotein |
| MBP | Myelin basic protein |

TABLE 1-continued

| Abbreviation | Description |
| --- | --- |
| Nkx 2.2 | NK2 transcription factor related, locus 2 |
| IE | Islet equivalent |
| Oct-4 | Octamer binding protein 3/4 |
| Pax | Paired homeobox gene |
| PCR | Polymerase chain reaction |
| PDX1 | Pancreatic duodenal homeobox protein-1 |
| PP | Pancreatic Polypeptide |
| Rex-1 | Reduced expression-1 |
| RIA | Radio Immuno-Assay |
| Rt-PCR | Quantitative real-time polymerase chain reaction |
| RT-PCR | Reverse Transcription polymerase chain reaction |
| SHh | Sonic Hedgehog |
| Sox-2 | SRY-related HMG-box 2 |
| SSEA | Stage Specific Embryonic Antigen |
| TDGF-1 | Teratocarcinoma-derived growth factor 1 |
| Thy-1 | Thymus cell antigen-1; CD90 |
| TRA 1-60 | Tumor related antigen-1-60 |
| TRA 1-81 | Tumor related antigen-1-81 |
| UGT1A1 | Uridine diphosphate glucuronosyltransferase |

DETAILED DESCRIPTION

Figure 1:
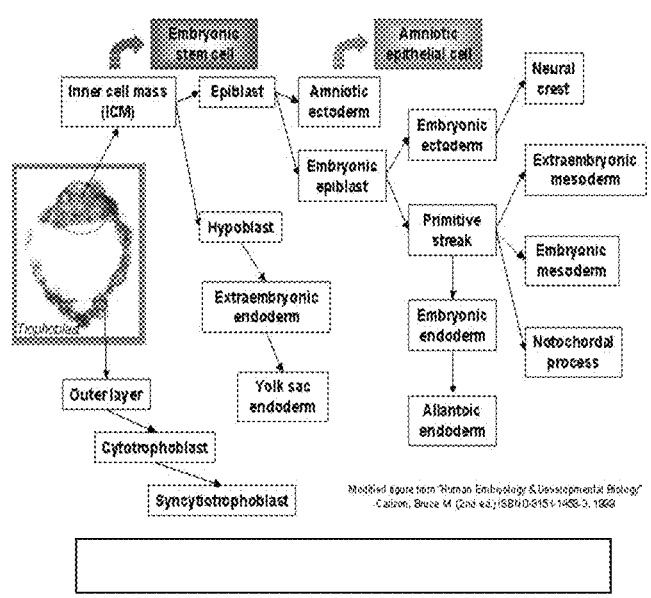
FIG. 1: A schematic representation of human embryological development.

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Production of Amnion-Derived Cell Compositions

In accordance with the invention, amnion-derived cell compositions are prepared using the steps of a) recovery of the amnion from the placenta, b) dissociation of the cells from the amniotic membrane, c) culturing of the cells in a basal medium with the addition of a naturally derived or recombinantly produced human protein; and optionally d) further proliferation of the cells using additional additives and/or growth factors.

Recovery of the Amnion—

The first step in obtaining the amnion-derived cell compositions of the invention is recovery of the cells from a placenta. In general, the placenta is processed as soon as possible after delivery. In preferred embodiments, the placenta is processed within four hours of delivery. If the placenta is refrigerated, or the amnion is stripped and refrigerated, the recovery may be done in up to 36 hours. The placenta used may be full term or pre-term placenta. Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172:493-500). However, the methods used herein provide improved compositions and populations of cells.

Under sterile conditions the amnion is stripped from the chorion manually, and placed in Hanks Balanced Salt Solution (HBSS) with no additives. This is preferably done at room temperature. The membranes are washed at least three times in HBSS, and washed further if necessary to remove remaining blood clots. Any tissue still heavily contaminated with blood is cut away and discarded.

Dissociation of Amniotic Membrane Cells—

The membranes are incubated with a dissociation reagent. This is done at least once and as many as ten times. In some embodiments, the dissociation reagent is a protease. In preferred embodiments, the protease is Protease XXIII (Sigma; 1 mg/ml). In other embodiments, the dissociation reagents include, but are not limited to: trypsin±EDTA, papain, elastase, hyaluronidase, collagenase type I, II, III, and IV, DNase, $Ca+2$ and $Mg+2$-free PBS, EDTA, EGTA, dispase, collagenase-dispase, Tryple (Gibco), collagenase, and dispase.

Characterizing, Identifying, Isolating and Creating Substantially Purified Populations of Amnion-Derived Cells.

Using commercially available antibodies to known stem cell markers, freshly isolated amnion-derived cells have been extensively characterized. As set forth in Example 7, freshly isolated amnion-derived cells are substantially purified with respect to CD90 and CD117. In addition, such populations are essentially negative for protein expression of CD34, CD44, CD45, CD140b, CD105; essentially positive for protein expression of CD9 and CD29; between about 70-95% positive for protein expression of SSEA4, CD10, CD166 and CD227; between about 60-95% positive for protein expression of HLA-G, EGFR and CD26; and between about 10-50% positive for protein expression of CD71.

In alternative embodiments substantially purified amnion-derived cell populations can be created using antibodies against protein markers expressed (positive selection) or not expressed (negative selection) on the cell surface of the amnion-derived cells. For instance, Example 8 below demonstrates how antibodies can be used to create substantially purified populations. These antibodies may be used to identify, characterize, isolate or create such substantially purified populations of amnion-derived cells expressing those protein markers using a variety of methods. Such procedures may involve a positive selection, such as passage of sample cells over a column containing anti-protein marker antibodies or by binding of cells to magnetic bead-conjugated antibodies to the protein markers or by panning on plates coated with protein marker antibodies and collecting the bound cells. Alternatively, a single-cell suspension may be exposed to one or more fluorescent-labeled antibodies that immuno-specifically bind to amnion-derived cell protein markers. Following incubation with the appropriate antibody or antibodies, the amnion-derived cells are rinsed in buffer to remove any unbound antibody. Amnion-derived cells expressing the protein marker(s) can then be sorted by fluorescence-activated cell sorting (FACS) using, for example, a Becton Dickinson FACStar flow cytometer. To create substantially purified populations of amnion-derived cells expressing a desired protein marker(s), the cells may be subjected to multiple rounds of FACS sorting.

In addition, protein markers that are not expressed on the surface of amnion-derived cells may also be used to identify, isolate or create populations of amnion-derived cells not expressing those markers. Such procedures may involve a negative selection method, such as passage of sample cells over a column containing anti-protein marker antibodies or by binding of cells to magnetic bead-conjugated antibodies to the protein markers or by panning on plates coated with protein marker antibodies and collecting the unbound cells. Alternatively, a single-cell suspension may be exposed to one or more fluorescent-labeled antibodies that immuno-specifically bind to the protein markers. Following incubation with the appropriate antibody or antibodies, the cells are rinsed in buffer to remove any unbound antibody. Cells expressing the protein marker(s) can then be sorted by fluorescence-activated cell sorting (FACS) using, for example, a Becton Dickinson FACStar flow cytometer and these cells can be removed. Remaining cells that do not bind to the antibodies can then be collected. To create substantially purified populations of amnion-derived cells that do not express a desired protein marker(s), the cells may be subjected to multiple rounds of FACS sorting as described above.

The present invention further contemplates novel antibodies to amnion-derived cells or to amnion-derived cell protein markers described herein. The antibodies are useful for detection of the amnion-derived cell protein markers in, for example, diagnostic applications. For preparation of monoclonal antibodies directed toward amnion-derived cells or to amnion-derived cell protein markers, any technique which provides for the production of antibody molecules by continuous cell lines in culture may be used. For example, various protocols for the production of monoclonal antibodies can be found in Monoclonal Antibody Protocols, Margaret E. Shelling, Editor, Humana Press; 2nd edition (Mar. 15, 2002). In addition, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77-96) and the like are within the scope of the present invention.

The monoclonal antibodies may be human monoclonal antibodies or chimeric human-mouse (or other species) trionoclonal antibodies. Human monoclonal antibodies may be made by any of numerous techniques known in the art (e g, Teng et al., 1983, Proc. Natl. Acad. Sci. U.S.A. 80:7308-7312; Kozbor et al., 1983, Immunology Today 4:72-79; Olsson et al., 1982, Meth. Enzymol. 92:3-16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of the amnion-derived cells or to the amnion-derived cell protein markers described herein. For the production of antibody, various host animals can be immunized by injection with amnion-derived cells or to amnion-derived cell protein markers, or a fragment or derivative thereof, including but not limited to rabbits, mice and rats. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

A molecular clone of an antibody to selected amnion-derived cells or to amnion-derived cell protein marker epitope(s) can be prepared by known techniques. Recombinant DNA methodology (Sambrook et al, 2001, "Molecular Cloning: A Laboratory Manual"; Ausubel, ed., 1994, "Current Protocols in Molecular Biology" Volumes I-III) may be used to construct nucleic acid sequences which encode a monoclonal antibody molecule, or antigen binding region thereof.

The present invention provides for antibody molecules as well as fragments of such antibody molecules. Antibody fragments which contain the idiotype of the molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent. Another antibody fragment is the single chain Fv (scFv) which is a truncated Fab having only the V region of a heavy chain linked by a stretch of synthetic peptide to a V region of a light chain. See, for example, U.S. Pat. Nos. 5,565,332; 5,733,743; 5,837,242; 5,858,657; and 5,871,907 assigned to Cambridge Antibody Technology Limited incorporated by reference herein. Antibody molecules may be purified by known techniques, e.g., immunoabsorption or immunoaffinity chromatography, chromatographic methods such as HPLC (high performance liquid chromatography), or a combination thereof.

Expanded Populations of Amnion-Derived Cells

As described herein, Applicants have discovered a novel method for isolation and propagation of pluripotent, amnion-derived cells. Such methods result in amnion-derived cell compositions which are expanded for pluripotent cells, thereby providing, for the first time, sufficient quantities of cells to enable therapeutic cell transplantation. Expanded amnion-derived cell compositions, which are made in accordance with the subject invention, are compositions in which the level of multipotent cells per gram of amniotic tissue is at least 50 fold and up to 150 fold higher after 5 passages, as compared to about 20 fold using previous methods.

Additionally, the methods used for cell culture and proliferation provide a means to culture the cells, as well as other pluripotent cells, including, but not limited to, embryonic stem cells, in an animal-free system. Furthermore, the culture conditions described provide a cell that is less dependent on attachment to a culture surface for viability, thus allowing for propagation of the cells using suspension culture for efficient scale-up.

The expanded amnion-derived cell compositions described herein demonstrate extensive proliferative potential, express certain genes known to be expressed only in undifferentiated cells (i.e. Nanog and Oct-4) and can differentiate into cell types that normally arise from all three embryonic germ layers (endoderm, ectoderm and mesoderm). This differentiation potential suggests that these expanded amnion-derived cells may be able to contribute to a variety of cell types. The amnion-derived cell compositions described herein are also useful as feeder layers for the growth of a variety of cell types, including but not limited to embryonic stem cells (ES cells). Amnion-derived cells, including those described herein, also produce a wide variety of cytokines and growth factors, thereby making both the cell compositions, conditioned medium derived from the cells, cell lysates thereform, extracellular matrices produced by the cells, and combinations thereof useful to achieve rapid and effective wound healing, including scarless healing, and also useful in cosmetics, i.e. to achieve improvement in skin appearance.

Culturing of the Amniotic Cells—

The cells are cultured in a basal medium. Such medium includes, but is not limited to, Epilife (Cascade Biologicals), Opti-pro, VP-SFM, IMDM, Advanced DMEM, K/O DMEM, 293 SFM II (all made by Gibco; Invitrogen), HPGM, Pro 293S-CDM, Pro 293A-CDM, UltraMDCK, UltraCulture (all made by Cambrex), Stemline I and Stemline II (both made by Sigma-Aldrich), DMEM, DMEM/F-12, Ham's F12, M199, and other comparable basal media. Such media should either contain human protein or be supplemented with human protein. As used herein a "human protein" is one that is produced naturally or one that is produced using recombinant technology. "Human protein" also is meant to include a human fluid or derivative or preparation thereof, such as human serum or amniotic fluid, which contains human protein. In preferred embodiments, the basal media is Stemline I or II, UltraCulture, or Opti-pro, or combinations thereof and the human protein is human albumin at a concentration of at least 0.5% and up to 10%. In particular embodiments, the human albumin concentration is from about 0.5 to about 2%. The human albumin may come from a liquid or a dried (powder) form and includes, but is not limited to, recombinant human albumin, plasbumin and plasmanate.

In a most preferred embodiment, the cells are cultured using a system that is free of animal products to avoid xeno-contamination. In this embodiment, the culture medium is Stemline I or II, Opti-pro, or DMEM, with human albumin (plasbumin) added up to concentrations of 10%. Alternatively, UltraCulture may be used, with substitution of transferrin with human recombinant transferrin, and replacement of the bovine albumin (BSA) with human albumin at concentrations of up to 10%. The invention further contemplates the use of any of the above basal media wherein animal-derived proteins are replaced with recombinant human proteins and animal-derived serum, such as BSA, is replaced with human albumin. In preferred embodiments, the media is serum-free in addition to being animal-free.

Further, the culture conditions described herein result in the formation of three-dimensional clusters of cells called spheroids, a property that may enhance the likelihood of differentiation to, for example, pancreatic islet cells, neural lineages and cardiac cells. Such compositions are prepared as described above using a basal media selected from the group consisting of Opti-pro SFM, VP-SFM, Iscove's MDM, HPGM, UltraMDCK, Stemline II and Stemline I, DMEM, and DMEM:F12 with added human albumin, plasmanate or plasbumin at levels of up to 10%.

In alternative embodiments, where the use of non-human serum is not precluded, such as for in vitro uses, the culture medium may be supplemented with serum derived from mammals other than humans, in ranges of up to 40%.

Additional Proliferation—

Optionally, other proliferation factors are used. In one embodiment, epidermal growth factor (EGF), at a concentration of between 0-1 μg/ml is used. In a preferred embodiment, the EGF concentration is around 10 ng/ml. Alternative growth factors which may be used include, but are not limited to, TGFα or TGFβ (5 ng/ml; range 0.1-100 ng/ml), activin A, cholera toxin (preferably at a level of about 0.1 μg/ml; range 0-10 μg/ml), transferrin (5 μg/ml; range 0.1-100 μg/ml), fibroblast growth factors (bFGF 40 ng/ml (range 0-200 ng/ml), αFGF, FGF-4, FGF-8; (all in range 0-200 ng/ml), bone morphogenic proteins (i.e. BMP-4) or other growth factors known to enhance cell proliferation.

Passaging—

Cells are initially plated at a density of 25,000/cm$^2$-1,000,000/cm$^2$, on tissue culture treated plates, preferably at a density of about 130,000/cm$^2$. In one embodiment, the cells are grown on extracellular matrix treated plates, such as collagen, laminin, fibronectin, or Matrigel. To create the expanded amnion-derived cell compositions of the invention, the cells are passaged at least five (5) times as described below in Example 1. To create the spheroidal amnion-derived cell compositions of the invention, only one passage is required.

Growth of ES Cells—

The culture media described above may also be used to produce expanded or spheroidal preparations of embryonic stem cells (ES cells). In some embodiments, the culture medium is free of animal products. In preferred embodiments, the culture medium is free of animal product and is made without serum.

Large Scale Culture of Amnion-Derived Cells—

In further embodiments, large scale culture is used to produce the amnion-derived cell compositions, conditioned media therefrom, and cells for the preparation of cell lysates. The literature describing large-scale mammalian cell culture has predominantly related to the culture of cells such as Chinese hamster ovary (CHO) cells to produce therapeutic proteins (Moreira, J. L. et al. (1995) Biotechnol Prog, 11:575). In this case, the secretory product of the cells is the main product of interest. Technologies most often used for large-scale cell production have been spinner flasks and roller bottles, although roller bottles are being replaced in some applications, especially adherent cell culture, by hollow-fibre culture bioreactors and microcarrier bioreactor systems (Martin, I., et al. (2004) Trends Biotechnol, 22:80). Hollow fibre bioreactors combine synthetic fibres with mammalian cells. The cells are seeded between the fibres and grow in a 3-dimensional tissue-like formation. The fibres act as conduits for nutritional factors and oxygen to reach the cells, and also provide an exit for toxins and cellular by-products which need to be removed from the proximity of the cells. One of the drawbacks of hollow-fibre technology is the difficulty in recovery of the cells, although for some applications, such as extracorporeal hepatic assist devices, the cells remain in situ to perform their therapeutic purpose (Gerlach, J. C., (1997) Cell Biol Toxicol, 13:349).

Large scale cell culture may be used to culture the amnion-derived cells as a product for some therapeutic purposes, including both growth of cells for transplantation, as well as for production of conditioned media. Hematopoietic cells for bone marrow transplant have been cultured in suspension (Cheshier, S. H., et al, (1999) Proc Natl Acad Sci USA, 96:3120; Madlambayan, G. J., et al, (2001) J Hematother Stem Cell Res, 10:481), hepatocytes for extracorporeal assist devices (Gerlach, J. C., (1997) Cell Biol Toxicol, 13:349), keratinocytes for artificial skin applications (Zacchi, V., et al, (1998) J Biomed Mater Res, 40:187; Pellegrini, G., et al, (1998) Med Biol Eng Comput, 36:778; Waymack, P., et al, (2000) Burns, 26:609), and neural stem cells for neurodegenerative diseases (Kallos, M. S., et al. (2003) Med Biol Eng Comput, 41:271). If mammalian cells are anchorage-dependent and cannot be cultured in suspension, microcarrier beads or microcarriers can be used as a large surface area to which the cells can attach and grow in the suspension apparatus. The cell-covered microcarrier beads are maintained in suspension in the apparati used for cell suspension cultures, allowing for reductions in media usage and space requirements. One of the technical difficulties of microcarrier bead culture is the efficient removal of the cells from the beads themselves, without compromising viability (Varani, J., et al. (1986) J Biol Stand, 14:331). The preferred method would be to culture amnion-derived cells in suspension.

The scalable production of amnion-derived cells may be accomplished using systems currently being developed for human embryonic stem (hES) cells. Most examples of scale-up for hES cells include partial or complete differentiation during the scale-up process, for instance Gerecht-Nir and coworkers (Gerecht-Nir, S., et al. (2004) Biotechnol Bioeng, 86:493) report the scalability of ES cells as embryoid bodies. Other examples of differentiated scale-up for ES cells include cardiac cells (Zandstra, P. W., et al. (2003) Tissue Eng, 9:767) in which embryoid bodies are formed and treated with retinoic acid, and ES-derived hepatocyte scale-up in hollow fibre bioreactors (Gerlach, J. C., (1997) Cell Biol Toxicol, 13:349). Reports of scale-up of undifferentiated human ES cells are scarce, although mouse ES cells can be proliferated in hollow fibre bioreactors, with maintenance of their stem cell surface characteristics.

In other embodiments, the cells are cultured in suspension culture conditions including in suspension culture treated plates, and roller bottles (in roller bottles density range 100,000/ml-5 million/ml; preferred 1 million/ml), or spinner flasks with or without attachment to microcarrier beads. Examples 2, 3 and 4 sets forth methods of large scale production that may be used in accordance with the invention.

Experiments are performed to determine the medium and supplements that can be used for optimal cell growth and expression of differentiated function. The use of multiple spinner flasks permits the use of 2 or 3 replicates of each condition per experiment.

Once cells are grown successfully in suspension, they are then cultured in sufficient quantities for transplantation. One skilled in the art will recognize that the number of cells needed for transplantation will depend upon the specific application. Cells are harvested as determined in the first set of experiments above but instead of seeding into T-flasks or spinner flasks they are put into Wave bags. These are sterile plastic bags (Wave, Inc.) into which cells and medium are added. The bag and its contents are placed on a rocker that gently agitates the entire bag. In addition, $CO_2$ and air can be added continuously to the bag to maintain adequate oxygen and pH control. The range of bag sizes is 1 liter to 1000 liters. In one embodiment, 1 liter bags and a minimum working volume of 125 ml are used. As the cells grow, additional medium can be added until the 500 ml working volume is attained.

Amnion-derived cells are placed both into the Wave bags and into the normal T-flasks and incubated at 37° C. at 5% $CO_2$ in air. Daily samples of cells are withdrawn, in a class 100 biosafety cabinet, from each flask and vessel, and the cells are stained with trypan blue and counted on a hemacytometer. A graph of total and viable cell counts per ml is plotted with time to ensure that amnion-derived cells divide and remain viable with time in culture.

Wave bags have two main advantages over alternative culture vessels. Firstly, they are disposable and therefore cleaning validation is not necessary for each lot of cells. Secondly, because the rocking motion creates a wave of liquid in the bags, the gas exchange in the liquid is much higher than if the cells were in a stationary flask or spinner flask. As a result, the total attainable cell number is higher than in either the T-flasks or spinner flasks.

At specific intervals, samples are analyzed using reverse transcriptase and/or real time PCR for gene expression over time. The samples are examined for amnion-derived cell-specific markers such as Oct-4, nanog, etc. In addition, samples are measured by FACS analysis for cell surface markers of undifferentiated cells (SSEA-3 and 4, Tra-1-60 and Tra-1-81).

In addition, the ability of amnion-derived cells after suspension culture and proliferation to undergo differentiation to all three germ lineages (endoderm, mesoderm, and ectoderm) is analyzed. Such characterization of differentiative capacity is assessed by performing differentiation assays and analysis of gene expression by reverse transcriptase and/or real-time PCR and by low volume FACS analysis (or IHC).

At designated time intervals, the cells are removed from the culture vessels and cultured in differentiation protocols to determine their ability to differentiate to the three germ lineages after proliferation.

Compositions—

The compositions of the invention include substantially purified populations and pharmaceutical compositions of such. The compositions of the invention can be prepared in a variety of ways depending on the intended use of the compositions. For example, a composition useful in practicing the invention may be a liquid comprising an agent of the invention, i.e. a substantially purified population of amnion-derived cells, in solution, in suspension, or both (solution/suspension). The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment, salve, cream, or the like.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous and muco-adhesive.

Pharmaceutical Compositions—

The present invention provides pharmaceutical compositions of substantially purified populations of amnion-derived cells, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the composition is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, and still others are familiar to skilled artisans.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Treatment Kits—

The invention also provides for an article of manufacture comprising packaging material and a pharmaceutical composition of the invention contained within the packaging material, wherein the pharmaceutical composition comprises a substantially purified population of amnion-derived cells, and wherein the packaging material comprises a label or package insert which indicates that the substantially purified population of amnion-derived cells can be used for treating a variety of disorders including but not limited to diabetes, liver disease, neural disease, etc.

Amnion-Derived Cell Nuclei

In addition to amnion-derived cells themselves and products derived therefrom, another embodiment of the invention is the nuclei of amnion-derived cells. Such nuclei may be obtained using methods known in the art. These include removing the membranes from cells by either mechanical disruption or chemical means such as treatment with hyaluronidase or performed by mechanically extracting the nucleus with a pipet. The nuclei may then subsequently be transferred into somatic or germ cells, by for example, intracytoplasmic injection or electrofusion using methods known in the art as described in for example, US 20030234430 or US 20040268422. As amnion-derived cells are derived from extraembryonic tissue, specifically the amnion, they are non-somatic, non-fetal, and non-germ cells, thus unique among the donor cells typically used in the art.

Once the nuclei are transferred into another cell, the resulting cell may be used for any number of applications. One embodiment relates to methods of therapeutic nuclear cloning or cloning an animal by combining any enucleated cell with the nuclei from an amnion-derived cell. This embodiment encompasses the cloning of a variety of animals. These animals include all mammals (e.g., human, canines, felines, mice, rats, livestock cattle, sheep, goats, camels, pigs, horses, llamas). The donor amnion-derived cell and the oocyte may or may not be from the same animal.

The genome of the donor amnion-derived cell can be the naturally occurring genome, for example, for the production of cloned animals, or the genome can be genetically altered to comprise a transgenic sequence, for example, for the production of transgenic cloned animals.

The oocytes used in the present invention could be in any stage of meiotic cell division, including metaphase I, anaphase I, anaphase II, telophase I, telophase II, and preferably metaphase II. Oocytes in metaphase II are considered to be in a resting state. The oocytes can be in the resting stage of metaphase II, and then be activated, using methods described herein. The stage that the oocyte is in can be identified by visual inspection of the oocyte under a sufficient magnification. Methods for identifying the stage of meiotic cell division are known in the art.

Oocytes can be activated by physical (e.g. electrical stimulation, cold shock) and chemical means (e.g. ethanol, acid tyrode's solution, strontium chloride, calcium ionophore, puromycin, hyaluronidase and media lacking calcium and magnesium). Some of these methods activate oocytes by increasing intracellular calcium levels. Several methods exist that allow for activation of the oocyte. In particular, a calcium ionophore (e.g., ionomycin) is an agent that increases the permeability of the oocyte's membrane and allows calcium to enter into the oocyte. Such methods of activation are described in U.S. Pat. No. 5,496,720. Ethanol has a similar affect. Prior to or following enucleation, an oocyte in metaphase II can be activated with ethanol according to the ethanol activation treatment as described in Presicce and Yang, Mol. Reprod. Dev., 37: 61-68 (1994); and Bordignon & Smith, Mol. Reprod. Dev., 49: 29-36 (1998). Exposure of calcium to the oocyte also occurs through electrical stimulation. The electrical stimulation allows increasing levels of calcium to enter the oocyte. Other known methods of activation can be used with the present invention to activate the oocyte.

Oocytes can be obtained from a donor animal during that animal's reproductive cycle. For example, oocytes can be aspirated from follicles of ovaries at given times during the reproductive cycle (exogenous hormone-stimulated i.e. super-ovulation or ovarian hyperstimulation or non-stimulated). Also at given times following ovulation, a significant percentage of the oocytes, for example, are in telophase. Additionally, oocytes can be obtained and then induced to mature in vitro to an arrested metaphase II stage. Arrested metaphase II oocytes, produced in vivo or in vitro, can then be induced in vitro to enter telophase. Thus, oocytes in telophase can readily be obtained for use in the present invention. Oocytes can also be recovered surgically by flushing the oocytes from the oviduct of a female donor. Methods for the collection of oocytes are known in the art.

Preferably, the cell stage of the activated oocytes correlates to the stage of the cell cycle of the donor amnion-derived cell. This correlation between the meiotic stage of the oocyte and the mitotic stage of the donor cell is also referred to herein as "synchronization."

The present invention utilizes an oocyte that is enucleated. An enucleated oocyte is one that is devoid of the genome, or one that is "functionally enucleated." A functionally enucleated oocyte contains a genome that is non-functional, e.g., cannot replicate or synthesize DNA. See, for example, Bordignon, V. and L. C. Smith, Molec. Reprod. Dev., 49: 29-36 (1998). Preferably, the genome of the oocyte is removed from the oocyte. A genome can be functionally enucleated from the oocyte by irradiation, by x-ray irradiation, by laser irradiation, by physically removing the genome, or by chemical means. Methods of using irradiation are known to those in the art and are described, for example, in Bradshaw et al., Molecul. Reprod. Dev., 41: 503-512 (1995). Methods of chemically inactivating the DNA are known to those of skilled in the art (Fulka and Moore, Molecul. Reprod. Dev., 34: 427-430 (1993). Other known methods of enucleation can be used with the present invention to enucleate the oocyte.

To physically remove the genome of an oocyte, one can insert a micropipette or needle through the zona pellucida of the oocyte to remove nuclear material from the oocyte. In one example, telophase oocytes which have two polar bodies can be enucleated with a micropipette or needle by removing the second polar body in surrounding cytoplasm. Specifically, oocytes in telophase stage of meiosis can be enucleated at any point from the presence of a protrusion in the plasma membrane from the second polar body up to the formation of the second polar body itself. Thus, as used herein, oocytes which demonstrate a protrusion in the plasma membrane, usually with a spindle abutted to it, up to extrusion of a second polar body are considered to be oocytes in telophase. In another example, metaphase II stage oocytes can be enucleated by puncturing the zona pellucida with a micropipette, abutting the micropipette to the oocyte nucleus, withdrawing the nucleus and part of the oolemma (or oocytes membrane) into the pipette. After withdrawal of the micropipette the oolemma pinches off to leave a membrane-intact enucleated oocyte. Oocytes can also be pre-treated with cytochalasin D to aid in this process.

The present invention includes enucleating the genome of an oocyte by treating the oocyte with a compound that will induce the oocyte genome (e.g., nuclear chromatin) to segregate into the polar bodies during meiotic maturaton thereby leaving the oocyte devoid of a functional genome, and resulting in the formation of a recipient cytoplast for use in nuclear transfer procedures. Examples of agents that will effect such differential segregation include agents that will disrupt cytoskeletal and metabolism (see, for example Andreau, J. M. and Timasheff, S, N., Proc. Nat. Acad. Sci. 79: 6753 (1982), Obrig, T. G., et al, J. Biol. Chem. 246: 174 (1971), Duskin, D. and Mahoney, W. C., J. Biol. Chem. 257: 3105 (1982), Scialli, A. R., et al, Teratogen, Carcinogen, Mutagen 14: 23 (1994), Nishiyama, I. and Fujii, T., Exp. Cell Res. 198: 214 (1992), Small, J. V., et al, J. Cell Sci. 89: 21 (1988), Lee, J. C., et al, Biochem. 19: 6209 (1980). The age of the oocyte and timing of the events (i.e. enucleation, fusion and activation) are also very important in successful nuclear transfer and are well known to those skilled in the art.

Combination of the activated, enucleated oocyte and the genome from the amnion-derived cell can occur a variety of ways to form the nuclear transfer embryo. A genome of an amnion-derived cell can be injected into the activated oocyte by employing a microinjector (i.e., micropipette or needle). The nuclear genome of the amnion-derived cell is extracted using a micropipette or needle. Once extracted, the amnion-derived cell's nuclear genome can then be placed into the activated oocyte by inserting the micropipette, or needle, into the oocyte and releasing the nuclear genome of the amnion-derived cell. (McGrath, J. and D. Solter, Science, 226: 1317-1319 (1984)).

The present invention also includes combining the genome of an amnion-derived cell with an activated oocyte by fusion e.g., electrofusion, viral fusion, liposomal fusion, biochemical reagent fusion (e.g., phytohemaglutinin (PHA) protein), or chemical fusion (e.g., polyethylene glycol (PEG) or ethanol). The amnion-derived cell, an amnion-derived cell karyoplast or the nucleus of the amnion-derived cell can be deposited within the zona pellucida which contains the oocyte. The steps of fusing the cell, karyoplast or nucleus with the oocyte can then be performed by techniques known in the art. The combination of the genome of the amnion-derived cell with the activated oocyte results in a nuclear transfer embryo.

A nuclear transfer cell of the present invention could then be transferred into a recipient non-human female animal and allowed to develop or gestate into a cloned or transgenic animal. Conditions suitable for gestation are those conditions that allow for the embryo to develop and mature into a fetus, and eventually into a live animal. Such conditions are known in the art. The nuclear transfer cell can be maintained in a culture system until at least the first cleavage (2-cell stage) up to the blastocyst stage. Preferably the nuclear transfer cells are transferred at the 2-cell or 4-cell stage. Various culture media for nuclear transfer cell development are known to those skilled in the art.

The present invention also relates to methods for generating transgenic animals by combining an activated oocyte with a genetically engineered genome from an amnion-derived cell. Such a combination results in a transgenic nuclear transfer cell. A transgenic animal is an animal that has been produced from a genome from a donor cell that has been genetically altered, for example, to produce a particular protein (a desired protein), or that has been altered to knock-out a particular gene. Methods for introducing DNA constructs into the germ line of an animal to make a transgenic animal are known in the art.

The present invention is also directed to "therapeutic cloning", which is the production of ES cells from a cloned embryo. Previously, Munsie, at al. reported the isolation of mouse ES cells from blastocysts derived by somatic cell nuclear transfer (Current Biology 10: 989-992, 2000). Wakayama, et al. obtained mouse ES cells, which can be induced to various types of specific cells in vitro, from the cultures of blastocysts derived by somatic cell nuclear transfer (Science, 292 (5517); 740-743. 2001). The result of the research done by Wakayama, et al. demonstrates that ES cells can be isolated from nuclear transfer embryos by somatic cell nuclear transfer. The nuclear transfer ES cells of somatic cell origin are pluripotent and can differentiate into any specific cell types as ES cells derived from the normal zygote.

In the present invention, therapeutic cloning is accomplished by the nuclear transfer of an amnion-derived cell nucleus into an oocyte. The nuclear transfer cells obtained are further differentiated into a specific cell type needed by, for example, a patient suffering from a disease (i.e. diabetes, liver failure, etc.).

Therapeutic Uses of Amnion-Derived Cells and Differentiated Cells

Because these compositions comprise much higher cell numbers per amniotic tissue than have previously been achieved, they allow for therapeutic use in situations, such as transplantation, which require large numbers of cells. These cells have been found to be multipotent, i.e. capable of differentiating into a variety of tissue types including but not limited to hematopoietic, liver, pancreatic, nervous, muscle and endothelial tissues. Such cells are particularly useful to restore function in diseased tissues via transplantation therapy or tissue engineering, and to study metabolism and toxicity of compounds in drug discovery efforts.

Cell transplantation strategies currently used in the clinic or in clinical trials have demonstrated promising results, e.g., 1) Pancreatic islets, isolated from cadaver tissue, are currently transplanted to restore proper insulin secretion and alleviate the need for insulin injections in Type I diabetic patients and 2) Hepatocytes isolated from cadaver livers are transplanted to treat patients awaiting liver transplant and for treatment of metabolic disorders. However, the need for clinical grade pancreatic islets and hepatocytes far exceeds the number of cells that can be isolated and transplanted from donor tissue. Expanded amnion-derived cell compositions described herein provide an abundant cell source that can be differentiated to these cell types.

Compositions comprising amnion-derived cell or cells differentiated therefrom may be administered to a subject to provide various cellular or tissue functions. As used herein "subject" may mean either a human or non-human animal.

Such compositions may be formulated in any conventional manner using one or more physiologically acceptable carriers optionally comprising excipients and auxiliaries. Proper formulation is dependent upon the route of administration chosen. The compositions may be packaged with written instructions for use of the cells in tissue regeneration, or restoring a therapeutically important metabolic function. Amnion-derived cells may also be administered to the recipient in one or more physiologically acceptable carriers. Carriers for these cells may include but are not limited to solutions of phosphate buffered saline (PBS) or lactated Ringer's solution containing a mixture of salts in physiologic concentrations.

One of skill in the art may readily determine the appropriate concentration of cells for a particular purpose. A preferred dose is in the range of about $0.25$-$1.0 \times 10^6$ cells.

Amnion-derived cells or cells differentiated therefrom can be administered by injection into a target site of a subject, preferably via a delivery device, such as a tube, e.g., catheter. In a preferred embodiment, the tube additionally contains a needle, e.g., a syringe, through which the cells can be introduced into the subject at a desired location. Specific, non-limiting examples of administering cells to subjects may also include administration by subcutaneous injection, intramuscular injection, or intravenous injection. If administration is intravenous, an injectable liquid suspension of cells can be prepared and administered by a continuous drip or as a bolus.

Cells may also be inserted into a delivery device, e.g., a syringe, in different forms. For example, the cells can be suspended in a solution contained in such a delivery device. As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating amnion-derived cells or differentiated cells as described herein, in a pharmaceutically acceptable carrier or diluent and, as required, other ingredients enumerated above, followed by filter sterilization.

Undifferentiated, partially differentiated or fully differentiated amnion-derived cells may be administered systemically (for example intravenously) or locally (for example directly into a myocardial defect under echocardiogram guidance or by direct application under visualization during surgery). For such injections, the cells may be in an injectable liquid suspension preparation or in a biocompatible medium which is injectable in liquid form and becomes semi-solid at the site of damaged tissue. A conventional intra-cardiac syringe or a controllable endoscopic delivery device can be used so long as the needle lumen or bore is of sufficient diameter (e.g. 30 gauge or larger) that shear forces will not damage the cells being delivered.

Cells may be administered in a manner that permits them to graft to the intended tissue site and reconstitute or regenerate the functionally deficient area. Undifferentiated, partially differentiated or fully differentiated amnion-derived cells can be used in therapy by direct administration, or as part of a bio-assist device that provides temporary or permanent organ function. In this respect, undifferentiated, partially differentiated or fully differentiated amnion-derived cells may be grown in a bioreactor to provide extracorporeal organ support for organ relief, such as in the case of a liver assist device, to provide a plentiful source of cells for transplantation to restore organ function, or provide a source of conditioned medium that may be used to stimulate tissue regeneration. Liver assist devices utilizing primary porcine cells as well as primary human liver cells have been used successfully (Sauer, I. M., et al. Xenotransplantation (2003) 10:460-469; Irgang, M. et al. (2003) 28(2):141-154; Sauer, I. M. et al. (2002) Int. J. Art. Org. 25(10):1001-1006; Sauer, I. M. et al. (2002) J. Metabolic Brain Disease 17(4): 477-484, Sauer, I. M. et al. (2003) J. Hepatology 39(4):649-653). Amnion-derived cell-derived hepatocytes may be utilized in conjunction with this technology.

Alternatively, amnion-derived cells may be transplanted into the recipient where the cells will proliferate and differentiate to form new cells and tissues thereby providing the physiological processes normally provided by that tissue, or may produce factors that cause the migration and/or differentiation of cells in the area of the transplant. Tissues are an aggregation of similarly specialized cells united in the performance of a particular function. Tissue is intended to encompass all types of biological tissue including both hard and soft tissue. Soft tissue refers to tissues that connect, support, or surround other structures and organs of the body. Soft tissue includes muscles, tendons (bands of fiber that connect muscles to bones), fibrous tissues, fat, blood vessels, nerves, and synovial tissues (tissues around joints). Hard tissue includes connective tissue (e.g., hard forms such as osseous tissue or bone) as well as other muscular or skeletal tissue.

Support matrices into which the amnion-derived cells can be incorporated or embedded include matrices which are recipient-compatible and which degrade into products which are not harmful to the recipient. These matrices provide support and protection for undifferentiated and differentiated amnion-derived cells in vivo and are, therefore, the preferred form in which such cells are transplanted into the recipient subjects.

Natural and/or synthetic biodegradable matrices are examples of such matrices. Natural biodegradable matrices include plasma clots, e.g., derived from a mammal, collagen, fibronectin, and laminin matrices. Suitable synthetic material for a cell transplantation matrix must be biocompatible to preclude migration and immunological complications, and should be able to support extensive cell growth and differentiated cell function. It must also be resorbable, allowing for a completely natural tissue replacement. The matrix should be configurable into a variety of shapes and should have sufficient strength to prevent collapse upon implantation. Recent studies indicate that the biodegradable polyester polymers made of polyglycolic acid fulfill all of these criteria (Vacanti, et al. J. Ped. Surg. 23:3-9 (1988); Cima, et al. Biotechnol. Bioeng. 38:145 (1991); Vacanti, et al. Plast. Reconstr. Surg. 88:753-9 (1991)). Other synthetic biodegradable support matrices include synthetic polymers such as polyanhydrides, polyorthoesters, and polylactic acid. Further examples of synthetic polymers and methods of incorporating or embedding cells into these matrices are also known in the art. See e.g., U.S. Pat. Nos. 4,298,002 and 5,308,701.

Attachment of the cells to the polymer may be enhanced by coating the polymers with compounds such as basement membrane components, agar, agarose, gelatin, gum arabic, collagens types I, II, III, IV and V, fibronectin, laminin, glycosaminoglycans, mixtures thereof, and other materials known to those skilled in the art of cell culture. All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

One of the advantages of a biodegradable polymeric matrix is that angiogenic and other bioactive compounds can be incorporated directly into the support matrix so that they are slowly released as the support matrix degrades in vivo. As the cell-polymer structure is vascularized and the structure degrades, amnion-derived cells may differentiate according to their inherent characteristics. Factors, including nutrients, growth factors, inducers of differentiation or de-differentiation (i.e., causing differentiated cells to lose characteristics of differentiation and acquire characteristics such as proliferation and more general function), products of secretion, immuno-modulators, inhibitors of inflammation, regression factors, biologically active compounds which enhance or allow ingrowth of the lymphatic network or nerve fibers, hyaluronic acid, and drugs, which are known to those skilled in the art and commercially available with instructions as to what constitutes an effective amount, from suppliers such as Collaborative Research, Sigma Chemical Co., vascular growth factors such as vascular endothelial growth factor (VEGF), epidermal growth factor (EGF), and heparin binding epidermal growth factor like growth factor (HB-EGF), could be incorporated into the matrix or be provided in conjunction with the matrix. Similarly, polymers containing peptides such as the attachment peptide RGD (Arg-Gly-Asp) can be synthesized for use in forming matrices (see e.g. U.S. Pat. Nos. 4,988,621, 4,792,525, 5,965,997, 4,879,237 and 4,789,734).

In another example, the undifferentiated, partially differentiated or fully differentiated amnion-derived cells may be transplanted in a gel matrix (such as Gelfoam from Upjohn Company) which polymerizes to form a substrate in which the cells can grow. A variety of encapsulation technologies have been developed (e.g. Lacy et al., Science 254:1782-84 (1991); Sullivan et al., Science 252:718-712 (1991); WO 91/10470; WO 91/10425; U.S. Pat. No. 5,837,234; U.S. Pat. No. 5,011,472; U.S. Pat. No. 4,892,538). During open surgical procedures, involving direct physical access to the damaged tissue and/or organ, all of the described forms of undifferentiated, partially differentiated or fully differentiated amnion-derived cell delivery preparations are available options. These cells can be repeatedly transplanted at intervals until a desired therapeutic effect is achieved.

The present invention also relates to the use of amnion-derived cells in three dimensional cell and tissue culture systems to form structures analogous to tissue counterparts in vivo. The resulting tissue will survive for prolonged periods of time, and perform tissue-specific functions following transplantation into the recipient host. Methods for producing such structures are described in U.S. Pat. Nos. 5,624,840 and 6,428,802, which are incorporated herein in their entireties.

The three-dimensional matrices to be used are structural matrices that provide a scaffold for the cells, to guide the process of tissue formation. Scaffolds can take forms ranging from fibers, gels, fabrics, sponge-like sheets, and complex 3-D structures with pores and channels fabricated using complex Solid Free Form Fabrication (SFFF) approaches. Cells cultured on a three-dimensional matrix will grow in multiple layers to develop organotypic structures occurring in three dimensions such as ducts, plates, and spaces between plates that resemble sinusoidal areas, thereby forming new liver tissue. Thus, in preferred aspects, the present invention provides a scaffold, multi-layer cell and tissue culture system. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions. The structure of the scaffold can include a mesh, a sponge or can be formed from a hydrogel.

Examples of such scaffolds include a three-dimensional stromal tissue or living stromal matrix which has been inoculated with stromal cells that are grown on a three dimensional support. The extracellular matrix proteins elaborated by the stromal cells are deposited onto the scaffold, thus forming a living stromal tissue. The living stromal tissue can support the growth of amnion-derived cells or differentiated cells later inoculated to form the three-dimensional cell culture. Examples of other three dimensional scaffolds are described in U.S. Pat. No. 6,372,494.

The design and construction of the scaffolding to form a three-dimensional matrix is of primary importance. The matrix should be a pliable, non-toxic, injectable porous template for vascular ingrowth. The pores should allow vascular ingrowth. These are generally interconnected pores in the range of between approximately 100 and 300 microns, i.e., having an interstitial spacing between 100 and 300 microns, although larger openings can be used. The matrix should be shaped to maximize surface area, to allow adequate diffusion of nutrients, gases and growth factors to the cells on the interior of the matrix and to allow the ingrowth of new blood vessels and connective tissue. At the present time, a porous structure that is relatively resistant to compression is preferred, although it has been demonstrated that even if one or two of the typically six sides of the matrix are compressed, that the matrix is still effective to yield tissue growth.

The polymeric matrix may be made flexible or rigid, depending on the desired final form, structure and function. For repair of a defect, for example, a flexible fibrous mat is cut to approximate the entire defect then fitted to the surgically prepared defect as necessary during implantation. An advantage of using the fibrous matrices is the ease in reshaping and rearranging the structures at the time of implantation.

A sponge-like structure can also be used to create a three-dimensional framework. The structure should be an open cell sponge, one containing voids interconnected with the surface of the structure, to allow adequate surfaces of attachment for sufficient amnion-derived cells or differentiated cells to form a viable, functional implant.

The invention also provides for the delivery of amnion-derived cells, including amnion-derived cell compositions described herein, in conjunction with any of the above support matrices as well as amnion-derived membranes. Such membranes may be obtained as a by-product of the process described herein for the recovery of amnion-derived cells, or by other methods, such as are described, for example, in U.S. Pat. No. 6,326,019 which describes a method for making, storing and using a surgical graft from human amniotic membrane, US 2003/0235580 which describes reconstituted and recombinant amniotic membranes for sustained delivery of therapeutic molecules, proteins or metabolites, to a site in a host, U.S. 2004/0181240, which describes an amniotic membrane covering for a tissue surface which may prevent adhesions, exclude bacteria or inhibit bacterial activity, or to promote healing or growth of tissue, and U.S. Pat. No. 4,361,552, which pertains to the preparation of cross-linked amnion membranes and their use in methods for treating burns and wounds. In accordance with the present invention, amnion-derived cells may be grown on such membranes, added to the membrane in either an undifferentiated, partially differentiated or fully differentiated form, or amnion-derived cell conditioned media or cell lysates may be added to such membranes. Alternatively, amniotic tissue in which amnion-derived cells have not been stripped away may be used to deliver amnion-derived cells to a particular site. In all cases, amnion-derived cells used in conjunction with amniotic tissue or other matrices can be used in combination with other therapeutically useful cells and/or cells expressing biologically active therapeutics such as those described in below.

Amnion-derived cells and cells differentiated therefrom may also be used to humanize animal organs. Human amnion-derived cells may be similarly transplanted into another organ such as pancreas or brain or heart. The animal organ may or may not be depleted of its native cells prior to the transplant. "Humanized" organs of an animal such as a mouse, rat, monkey, pig or dog could be useful for organ transplants into humans with specific diseases.

Humanized animal models may also be used for diagnostic or research purposes relating but not limited to, drug metabolism, toxicology studies or for the production, study, or replication of viral or bacterial organisms. Mice transplanted with human hepatocytes forming chimeric human livers are currently being used for the study of hepatitis viruses (Dandri et al. Hepatol. 33:981-988 (2001); Mercer et al. Nature Med. 7:927-933 (2001)).

Amnion-derived cells may be genetically engineered to produce a particular therapeutic protein. Therapeutic protein includes a wide range of biologically active proteins including, but not limited to, growth factors, enzymes, hormones, cytokines, inhibitors of cytokines, blood clotting factors, peptide growth and differentiation factors. Particular differentiated cells may be engineered with a protein that is normally expressed by the particular cell type. For example, pancreatic cells can be engineered to produce digestive enzymes. Hepatocytes can be engineered to produce the enzyme inhibitor, A1AT, or clotting factors to treat hemophilia. Furthermore, neural cells can be engineered to produce chemical transmitters.

Methods which are well known to those skilled in the art can be used to construct expression vectors containing a nucleic acid encoding the protein of interest linked to appropriate transcriptional/translational control signals. See, for example, the techniques described in Sambrook et al, 2001, "Molecular Cloning: A Laboratory Manual"; Ausubel, ed., 1994, "Current Protocols in Molecular Biology" Volumes I-III; Celis, ed., 1994.

Suitable methods for transferring vector or plasmids into amnion-derived cells or cells differentiated therefrom include lipid/DNA complexes, such as those described in U.S. Pat. Nos. 5,578,475; 5,627,175; 5,705,308; 5,744,335; 5,976,567;

6,020,202; and 6,051,429. Suitable reagents include lipofectamine, a 3:1 (w/w) liposome formulation of the polycationic lipid 2,3-dioleyloxy-N-[2(sperminecarbox-amido)ethyl]-N,N-dimethyl-1-propanaminium trifluoroacetate (DOSPA) (Chemical Abstracts Registry name: N-[2-(2,5-bis[(3-aminopropyl)amino]-1-oxpentyl)amino)ethyl]-N,N-dimethyl-2,3-bis(9-octadecenyloxy)-1-propanamin-trifluoroacetate), and the neutral lipid dioleoyl phosphatidylethanolamine (DOPE) in membrane filtered water. Exemplary is the formulation Lipofectamine 2000™ (available from Gibco/Life Technologies #11668019). Other reagents include: FuGENE™ 6 Transfection Reagent (a blend of lipids in non-liposomal form and other compounds in 80% ethanol, obtainable from Roche Diagnostics Corp. #1814443); and LipoTAXI™ transfection reagent (a lipid formulation from Invitrogen Corp., #204110). Transfection of amnion-derived cells can be performed by electroporation, e.g., as described in Roach and McNeish (Methods in Mol. Biol. 185:1 (2002)). Suitable viral vector systems for producing stem cells with stable genetic alterations may be based on adenoviruses, lentiviruses, retroviruses and other viruses, and may be prepared using commercially available virus components.

Amnion-derived cells that are undifferentiated, partially differentiated, or fully differentiated may be administered or transplanted to a subject to provide various cellular or tissue functions specific to the differentiated cell type. For example, amnion-derived cells differentiated into hepatocytes may be transplanted into a patient suffering from liver disease. The progress of the recipient receiving such cells or transplants can be determined using assays that include blood tests known as liver function tests. Efficacy of treatment can be determined by immunocytochemical staining for liver cell markers, microscopic determination of whether canalicular structures form in growing tissue, and the ability of the treatment to restore synthesis of liver-specific proteins. Amnion-derived cell-derived hepatocytes of the invention can be assessed in animal models for their ability to repair liver damage. Hepatocytes derived from amnion-derived cells may be used in assays to detect the activity of specific metabolic pathways. For detailed examples of the above, see US2003/0235563 and US2004/0161419, which are incorporated herein by reference.

Pancreatic cells derived from amnion-derived cells can be used therapeutically for treatment of various diseases associated with insufficient functioning of the pancreas. Pancreatic diseases and treatment thereof using the pancreatic cells derived from amnion-derived cells of the subject invention are described in more detail below.

The present invention also provides for administration of neural cells derived from amnion-derived cells for treatment of neurological disease. Neurological disease refers to a disease or condition associated with any defects in the entire integrated system of nervous tissue in the body: the cerebral cortex, cerebellum, thalamus, hypothalamus, midbrain, pons, medulla, brainstem, spinal cord, basal ganglia and peripheral nervous system. Examples include but are not limited to: Parkinson's disease, Huntington's disease, Multiple Sclerosis, Alzheimer's disease, amyotrophic lateral sclerosis (ALS or Lou Gehrig's disease), Muscular dystrophy, choreic syndrome, dystonic syndrome, stroke, and paralysis.

The amnion-derived cells may be used in in vitro priming procedures that result in neural stem cells becoming neurons when grafted into non-neurogenic or neurogenic areas of the CNS. For details and examples, see US2003/0235563 and US2004/0161419, both which are incorporated herein by reference.

The amnion-derived cells can be used to produce vascular endothelial cells that may be used in methods for remodeling tissue or replacing a scar tissue in a subject. Vascular endothelial cells may also be used to repair vascular damage.

In an exemplary embodiment, a pharmaceutical composition comprising an effective amount of the vascular endothelial cells may be used to treat a subject with a vascular disease. Vascular disease refers to a disease of the human vascular system. Examples include peripheral arterial disease, abdominal aortic aneurysm, carotid disease, and venous disease.

The present invention also provides for cardiomyocytes derived from amnion-derived cells, which may be used therapeutically for treatment of various diseases associated with cardiac dysfunction. Cardiac disease or cardiac dysfunction as used herein refers to diseases that result from any impairment in the heart's pumping function. This includes, for example, impairments in contractility, impairments in ability to relax (sometimes referred to as diastolic dysfunction), abnormal or improper functioning of the heart's valves, diseases of the heart muscle (sometimes referred to as cardiomyopathy), diseases such as angina and myocardial ischemia and infarction characterized by inadequate blood supply to the heart muscle, infiltrative diseases such as amyloidosis and hemochromatosis, global or regional hypertrophy (such as may occur in some kinds of cardiomyopathy or systemic hypertension), and abnormal communications between chambers of the heart (for example, atrial septal defect). For further discussion, see Braunwald, Heart Disease: a Textbook of Cardiovascular Medicine, 5th edition, W B Saunders Company, Philadelphia Pa. (1997) (hereinafter Braunwald). Cardiomyopathy refers to any disease or dysfunction of the myocardium (heart muscle) in which the heart is abnormally enlarged, thickened and/or stiffened. As a result, the heart muscle's ability to pump blood is usually weakened. The disease or disorder can be, for example, inflammatory, metabolic, toxic, infiltrative, fibroblastic, hematological, genetic, or unknown in origin. There are two general types of cardiomyopathies: ischemic (resulting from a lack of oxygen) and nonischemic. Other diseases include congenital heart disease which is a heart-related problem that is present since birth and often as the heart is forming even before birth or diseases that result from myocardial injury which involves damage to the muscle or the myocardium in the wall of the heart as a result of disease or trauma. Myocardial injury can be attributed to many things such as, but not limited to, cardiomyopathy, myocardial infarction, or congenital heart disease.

The amnion-derived cells and/or differentiated cardiomyocytes may be administered and/or transplanted to a subject suffering from a cardiac disease in any fashion as previously discussed.

Methods are also provided for screening agents that affect cardiomyocyte differentiation or function. For details and examples see US2003/0235563 and US2004/0161419, which are incorporated herein by reference.

In another embodiment, amnion-derived cells, and their derivatives, can be used to screen various compounds to determine the effect of the compound on cellular growth, proliferation or differentiation of the cells. Methods of measuring cell proliferation are well known in the art and most commonly include determining DNA synthesis characteristic of cell replication. There are numerous methods in the art for measuring DNA synthesis, any of which may be used according to the invention. For example, DNA synthesis may be determined using a radioactive label ($^3$H-thymidine) or labeled nucleotide analogues (BrdU) for detection by immunofluorescence. The efficacy of the compound can be assessed by generating dose response curves from data obtained using various concentrations of the compound. A control assay can also be performed to provide a baseline for comparison. Identification of the amnion-derived cell population(s) amplified in response to a given test agent can be carried out according to such phenotyping as described above.

In order to assess the effect of a test agent on amnion-derived cell differentiation or function, the agent may be contacted with the amnion-derived cells and differentiation assessed using any means known to one of skill in the art. For examples and details, see US2003/0235563 and US2004/0161419, which are incorporated herein by reference.

In another embodiment, amnion-derived cell compositions prepared as describe herein are used as feeder layers for the growth of embryonic stem cells. Such amnion-derived cell compositions are preferably animal-free. Examples of use of such cells as feeders layers can be found in Miyamoto, K., et al. Stem Cells 2004:22:433-440 which is incorporated by reference in its entirely herein.

Wound Healing—

The compositions and methods of the present invention are effective in accelerating wound healing of wounds caused by a number of sources, including but not limited to incisional, compression, thermal, acute, chronic, infected, and sterile injuries. The instant invention is based upon the discovery that undifferentiated, partially differentiated or fully differentiated amnion-derived cells, conditioned medium therefrom, cell lysates therefrom, extracellular matrices therefrom, alone or in combination, as well as composition of placental-derived cells as defined herein can accelerate the wound healing process for all wound types, particularly when administered topically, i.e. to the surface of the wound site. Using amnion-derived cells and/or conditioned medium from such amnion-derived cells, all wound types, mechanical or thermal, acute or chronic, infected or sterile, undergo healing more rapidly than similar wounds left to heal naturally or which are treated with currently available methods. A "therapeutically effective amount" of a therapeutic agent within the meaning of the present invention will be determined by a patient's attending physician or veterinarian. Such amounts are readily ascertained by one of ordinary skill in the art and will enable accelerated wound healing when administered in accordance with the present invention. Factors which influence what a therapeutically effective amount will be include, the specific activity of the therapeutic agent being used, the wound type (mechanical or thermal, full or partial thickness, etc.), the size of the wound, the wound's depth (if full thickness), the absence or presence of infection, time elapsed since the injury's infliction, and the age, physical condition, existence of other disease states, and nutritional status of the patient. Additionally, other medication the patient may be receiving will effect the determination of the therapeutically effective amount of the therapeutic agent to administer.

In addition, compositions of the invention may play a role in more substantial wound healing, such as in the regeneration of limbs. US2003/0212024, which is incorporated by reference herein, sets forth methods of testing for such ability by measuring regeneration in the zebrafish, which is capable of complete regeneration following amputation of the distal fin. Following amputation, complete regeneration occurs in several steps, including formation of a wound epidermis, migration of fibroblasts and scleroblasts (or osteoblasts) toward the wound epidermis, formation of a blastema, and outgrowth of the blastema via cell division and differentiation of the proximal portion of the fin to form specific structures of the regenerated fin.

In a preferred embodiment of the present invention, amnion-derived cells and/or conditioned medium therefrom, and/or cell lysates thereof should be topically administered to the wound site to promote accelerated wound healing in the patient. This topical administration can be as a single dose or as repeated doses given at multiple designated intervals. It will readily be appreciated by those skilled in the art that the preferred dosage regimen will vary with the type and severity of the injury being treated.

Formulations suitable for topical administration in accordance with the present invention comprise therapeutically effective amounts of the therapeutic agent with one or more pharmaceutically acceptable carriers and/or adjuvants. Amnion-derived cells, conditioned media therefrom and cell lysates thereof may be used in conjunction with a variety of materials routinely used in the treatment of wounds, such as collagen based creams, films, microcapsules, or powders; hyaluronic acid or other glycosaminoglycan-derived preparations; creams, foams, suture material; and wound dressings. Alternatively, the amnion-derived cell compositions can be incorporated into a pharmaceutically acceptable solution designed for topical administration.

Cosmetic Applications—

The same properties that make undifferentiated, partially differentiated or fully differentiated amnion-derived cells, conditioned medium therefrom, cell lysates therefrom, extracellular matrices therefrom, alone or in combination, as well as composition of placental-derived cells as defined herein useful for wound healing make them similarly well-suited for the treatment of cosmetic and/or dermatological conditions, including aging skin. The dermal layer of skin, important in maintaining the elasticity and appearance of the skin, thins with age, leading to sagging and wrinkles.

As described above, fetal skin has much more effective repair mechanisms, and, once wounded, it is able to heal without the formation of scars. This capability does appear to require the fetal immune system, fetal serum, or amniotic fluid (Bleacher J C, et al., J Pediatr Surg 28: 1312-4, 1993); Ihara S, Motobayashi Y., Development 114: 573-82. 1992). Such abilities of fetal tissue have led to the suggested use of compounds produced by fetal tissue for regenerating and/or improving the appearance of skin (see, for example, US 2004/0170615, which is incorporated by reference in its entirety herein).

The present invention contemplates the use of the amnion-derived cell compositions described herein, as well as conditioned medium therefrom, and cell lysates thereof, in the use of novel cosmetic skin care compositions. Such compounds may be delivered to skin by way of, but not limited to, a solution, a lotion, an ointment, a cream, a gel, or a skin peelable strip.

The methods generally include the step of topically applying a safe and effective amount of the composition to the skin of a mammal in need thereof. Additional skin care components, as well as cosmetically acceptable, dermatologically acceptable or pharmaceutically acceptable carriers may be included in such compositions.

Cosmetic compositions usually comprise an aqueous phase that is gelled, i.e. thickened, using one or more thickener(s) or gelling agent(s). These may be, for example, lotions which are aqueous solutions not containing an oily phase, or emulsions which may be direct oil-in-water emulsions including a fatty phase or oily phase dispersed in an aqueous continuous phase, or water-in-oil reverse emulsions including an aqueous phase dispersed in an oily continuous phase. The term "emulsions" means herein both the dispersions obtained in the absence of emulsifying surfactants and the emulsions obtained in the presence of emulsifying surfactants.

Oil-in-water emulsions are the emulsions most frequently sought in cosmetics due to the fact that, when applied to the skin, they give a softer, less greasy, fresher and lighter feel than water-in-oil emulsion systems, by virtue of the presence of water in the continuous outer phase.

The nature of the compounds used for gelling the aqueous phase and their content in the composition are chosen as a function of the desired type of texture, which may range from fluid lotions to more or less thick emulsions that may constitute milks or creams. The main thickeners or gelling agents used in cosmetics are chosen from the following compounds natural polymers such as xanthan gum and guar gum or cellulose derivatives, starches and alginates and crosslinked polymeric gelling agents such as the Carbopols or crosslinked and at least partially neutralized 2-acrylamido-2-methylpropanesulfonic acid polymers.

Hearing Loss—

Undifferentiated, partially differentiated or fully differentiated amnion-derived cells, conditioned medium therefrom, cell lysates therefrom, extracellular matrices therefrom, alone or in combination, as well as composition of placental-derived cells as defined herein may also be used to treat hearing loss. Heretofore, hearing loss has been considered incurable because hair cells, which are the sensory cells of the cochlea, do not regenerate. Recently, however, both embryonic and adult stem cells have been shown to be capable of differentiating into mechanosensory hair cells (Li, H. et al. Nature Med. 9:1293-1299 (2003); Li, H. et al. Proc. Natl. Acad. Sci. USA 100:13495-13500). In addition, Atoh1 gene therapy has been used to promote phenotypic transgeneration, thus promoting the generation of hair cells from nonsensory cells in deaf mammals (Izumikawa, M. et al. 2005 Nature Medicine 11 (3):271-276). Further, human amniotic epithelial cells transplanted into the inner ear of guinea pigs have been shown to survive for up to three weeks and express crucial proteins which may maintain homeostasis (Yuge, I. et al. (2004):77 (9) 1452-1471).

Methods of Differentiating Amnion-Derived Cells and Differentiated Cell Types

The amnion-derived cells may be contacted with various growth factors (termed differentiation factors) that influence differentiation of such stem cells into particular cell types such as hepatocytes, pancreatic cells, vascular endothelial cells, muscle cells, cardiomyocytes and neural cells. For examples, see US2003/0235563 and US2004/0161419, the contents of which are incorporated herein by reference).

The literature is replete with additional differentiation protocols for embryonic as well as non-embryonic stem or other multipotent cells, including stem cells. For example, U.S. Pat. Nos. 6,607,720 and 6,534,052 described methods of improving cardiac function using embryonic stem cells and genetically altered embryonic stem cells in which differentiation has been initiated, for improving cardiac function and repairing heart tissue. U.S. Pat. No. 6,387,369 provides methods of cardiac tissue and muscle regeneration using mesenchymal stem cells. Shin, S. et al. have recently reported the differentiation of embryonic stem cells into motor neurons using a combination of basic fibroblast growth factor, sonic hedgehog protein, and retinoic acid. (Human motor neuron differentiation from human embryonic stem cells. Stem Cells Dev. 2005 June; 14(3):266-9). All of these references are incorporated herein in their entirety. One skilled in the art will recognize that any of these protocols can be applied to the amnion-derived cell compositions described herein to produce partially or fully differentiated cells for such uses. Other exemplary protocols are set forth below:

Endoderm (Pancreatic Differentiation).

Amnion-derived cell are exposed to conditions for differentiation of an islet progenitor cell population expressing PDX1. Briefly, cells are initially exposed to antagonists of the Sonic Hedgehog (SHh) signaling pathway to promote endoderm differentiation. Subsequent differentiation to early islet progenitor cells is accomplished using a combination of factors and conditions that promote cessation of cell growth, aggregation of differentiating cells, and expression of early pancreatic determination genes. Cells are harvested for RNA and analyzed by reverse transcriptase-PCR (RT-PCR) for Sox-17 and PDX1.

Mesoderm (Cardiac Differentiation).

Clusters of cells taken from the suspension cultures are transferred to gelatin- or poly-L-lysine coated plates for 8 days in culture medium with serum (80% KO-DMEM, 1 mM glutamine, 0.1 mM β-mercaptoethanol, 1% non-essential amino acids, and 20% FBS). For Days 2-4 in this culture 1 or 10 μM 5-aza-2'-deoxycytidine are added to the medium (Xu, C. et al. (2002) Circ. Res. 91:501-508). Analysis is performed on Day 8. Cells are harvested for RNA and analyzed by reverse transcriptase-PCR (RT-PCR) for GATA-4, Nkx2.5 and MEF-2. These transcription factors are expressed in precardiac mesoderm and persist in cardiac development.

Ectoderm (Neural Differentiation).

Clusters are removed from the large-scale apparatus and transferred to ultra-low adherence 6-well plates. The differentiation protocol described by Carpenter, M. K. et al. (2001) Exp Neurol 172:383-397 for human embryonic stem cells is followed for differentiation as follows. 10 mM all-trans retinoic acid (RA) will added to the culture medium (80% KO-DMEM, 1 mM glutamine, 0.1 mM β-mercaptoethanol, 1% non-essential amino acids, and 20% FBS) containing these clusters in suspension. After 4 days in suspension, clusters are plated onto poly-L-lysine/fibronectin-coated plates in differentiation medium (DMEM/F-12 with B27 (Gibco), 10 ng/ml human epidermal growth factor (hEGF), 10 ng/ml human basic fibroblast growth factor (hbFGF) (Gibco), 1 ng/ml human platelet-derived growth factor-AA (hPDGF-AA) (R & D Systems), and 1 ng/ml human insulin-like growth factor-1 (hIGF-1) (R & D Systems) for 3 days. After 3 days under these conditions, the cells are harvested for RNA or fixed. Fixed cells are immunostained for nestin, polysialylated neural cell adhesion molecule (PS-NCAM), and A2B5. RNA is analyzed by reverse transcriptase-PCR (RT-PCR) for nestin, GFAP and MAP-2.

Differentiated cells derived from amnion-derived cells may be detected and/or enriched by the detection of tissue-specific markers by immunological techniques, such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods.

Alternatively, differentiated cells may be detected using selection markers. For example, amnion-derived cells can be stably transfected with a marker that is under the control of a tissue-specific regulatory region as an example, such that during differentiation, the marker is selectively expressed in the specific cells, thereby allowing selection of the specific cells relative to the cells that do not express the marker. The marker can be, e.g., a cell surface protein or other detectable marker, or a marker that can make cells resistant to conditions in which they die in the absence of the marker, such as an antibiotic resistance gene (see e.g., in U.S. Pat. No. 6,015, 671).

Pancreatic Progenitor Cells

In another embodiment of the invention, cells are treated such that they differentiate into pancreatic progenitor cells, In this embodiment, amnion-derived cells, non-insulin producing embryonic, neonatal or fetal cells are cultured in serum-free culture medium comprising a SHh antagonist such as cyclopamine or jervine to obtain pancreatic cells having the identifying characteristics of endoderm, which include but are not limited to protein expression of HNF1α, HNF1β, HNF4α, HNF6, Fox2a and PDX1. The cells may be cultured in such medium after culturing in basal medium.

Pancreatic progenitor cells of the present invention expressing PDX1 protein in the nucleus may also be obtained by culturing cells in medium comprising an SHh antagonist. The cells may subsequently be cultured in medium comprising TAT-PDX1 fusion protein. Procedures for obtaining TAT-PDX1 are described infra. In a preferred embodiment, at least 20% of the cells in the composition, culture or population of the present invention express PDX1 protein in the nucleus. In other embodiments, at least 30%, 40%, 50%, 60%, 70%, 80%, or 90% of the cells in the composition, culture or population of the present invention express PDX1 protein in the nucleus. In a specific, preferred embodiment, 100% of the cells express PDX1 protein in the nucleus.

The composition, culture or population of cells of the present invention may be cultured in suspension or on a solid support, such as an adherent matrix or substrate. Details of such solid supports are described above. In one embodiment, the composition of cells is cultured on a Matrigel layer. Matrigel (Collaborative Research, Inc., Bedford, Mass.) is a complex mixture of matrix and associated materials derived as an extract of murine basement membrane proteins, consisting predominantly of laminin, collagen IV, heparin sulfate proteoglycan, and nidogen and entactin, and was prepared from the EHS tumor (Kleinman et al, (1986) Biochemistry 25: 312-318). Other such matrices can be provided, such as Humatrix. Likewise, natural and recombinantly engineered cells can be provided as feeder layers to the instant cultures. In another embodiment, the culture vessels are coated with one or more extra-cellular matrix proteins including, but not limited to, fibronectin, superfibronectin, laminin, collagen, and heparin sulfate proteoglycan.

In another embodiment, the progenitor cells of the present invention are cultured in the presence of three dimensional matrices. Examples of such three dimensional matrices are described in detail above.

Pancreatic Progenitor Cell Nuclei—

The invention is further directed to the nuclei of the pancreatic progenitor cells of the present invention. The nuclei of these cells may be obtained using methods known in the art. These include removing the membranes from cells by either mechanical disruption or chemical means such as treatment with hyaluronidase or performed by mechanically extracting the nucleus with a pipet and inserting it into a different or similar cell that has had its nucleus removed.

The nuclei may then subsequently be transferred into somatic or germ cells by, for example, intracytoplasmic injection, chemical fusion or electrofusion using methods known in the art as described in, for example, US 20030234430 or US 20040268422.

In a particular embodiment, therapeutic cloning may be undertaken using these nuclei to obtain cells that can be used for endoderm or other cell differentiation. In a more particular embodiment, the nuclei may be used to obtain embryonic stem-like cells. Details concerning therapeutic cloning are described above.

In addition to germ cells, the recipient cell may be any mammalian cell. In one embodiment, the mammalian cell is enucleated prior to receiving the donor nucleus. In another embodiment, the mammalian cell in not enucleated prior to receiving the donor nucleus. In this embodiment, both the recipient and donor nuclei are present in the recipient cell. The nuclei may fuse or they may stay separate. Instances in which it is desirable for both recipient and donor nuclei to be present are ones in which the object is to confer the tissue-specific functionality of the donor cell onto the recipient cell while still maintaining the tissue-specific functionality of the recipient cell. One of skill in the art will recognize that other combinations are within the scope of the invention.

Detection of Pancreatic Cells—

The pancreatic cells of the present invention described hereinabove can be detected in the composition, culture or population of cells of the present invention by detecting the presence or absence of various markers, such as HNF1α, HNF1β, HNF4α, HNF6, Foxa2, PDX1, Nkx2.2, Nkx6.1, Sox17, Cerberus, Hesx1, LeftyA, Otx1 and/or Otx2, insulin, human C-peptide, somatostatin and islet-1. In one embodiment, fragments of HNF1α, HNF1β, HNF4α, HNF6, Foxa2, PDX1, Nkx2.2, Nkx6.1, Sox17, Cerberus, Hesx1, LeftyA, Otx1 and/or Otx2, insulin, human C-peptide, somatostatin or islet-1 may be used as probes or primers for detecting RNA transcription of the markers. The markers may be detected by Northern blot analysis, for example, by hybridizing either total or poly A RNA isolated from the cells with probes and primers between 10-500 nucleotides in length, preferably between 20-200 nucleotides in length, more preferably between 20-100 nucleotides in length and most preferably between 20-50 nucleotides in length and subjecting to agarose gel electrophoresis. Alternatively, these fragments may be used as RT-PCR primers between about 10-100 nucleotides in length to amplify the RNA isolated from the cells. Cells suitable for such an analysis include cells isolated from human tissue. Methods for performing primer-directed amplification (routine or long range PCR) are well known in the art (see, for example, PCR Basics: From Background to Bench, Springer Verlag (2000); Gelfand et al., (eds.), PCR Strategies, Academic Press (1998)). Such probes may be between 20-5000 nucleotides in length and may preferably be between 20-50 nucleotides in length.

Alternatively, the above-mentioned markers may be detected using antibodies to the markers in RIA, ELISA, Western Blot or immunocytochemical techniques. The invention is thus directed to kits comprising antibodies binding to two or more of the above-mentioned markers.

TAT-PDX1 Fusion Protein—

The invention also relates to TAT-PDX1 fusion protein used in the culture medium for the purpose of obtaining pancreatic progenitor cells comprising PDX1 protein in the nucleus of the progenitor cells. TAT-PDX1 has the formula:

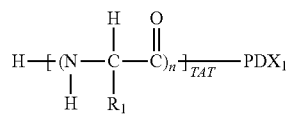

Wherein TAT is a TAT peptide having a self cell penetration property. The TAT peptide is derived from human immunodeficiency virus type-1 and is capable of passing through a cell membrane to easily penetrate the cell. This property is thought to be due to the protein transduction domain in the middle region of the TAT peptide sequence. R1 may be side chains of glutamine, lysine, arginine and/or glycine and n is an integer of 4 to 12.

In a specific embodiment, the TAT peptide may be Arg-Lys-Lys-Arg-Arg-Gln-Arg-Arg-Arg [SEQ. ID. NO. 1]; Lys-Lys-Lys-Lys-Lys-Lys-Lys-Lys [SEQ. ID. NO. 2]; or Arg-Arg-Arg-Arg-Arg-Arg-Arg-Arg-Arg [SEQ. ID. NO. 3].

PDX1 is a homeodomain-containing protein and is thought to be a key regulator of islet development and insulin gene transcription in beta cells (Inoue et al., 1996, Diabetes 6:789-794). It has the following amino acid sequence:

[SEQ. ID. NO. 4]
MNGEEQYYAATQLYKDPCAFQRGPAPEFSASPPACLYMGRQPPPPPPHPF

PGALGAEQGSPPDISPYEVPPLADDPAVAHLHHHLPAQLALPHPPAGPFP

EGAEPGVLEENRVQLPFPWMKSTKAHAWKGQWAGGAYAAEPEENKRTRTA

YTRAQLLELEKEFLFNKYISRPRRVELAVMLNLTERHIKIWFQNRRMKWK

KEEDKKRGGGTAVGGGGVAEPEQDCAVTSGEELLALPPPPPPGGAVPPAA

PVAAREGRLPPGLSASPQPSSVAPRRPQEPR and is encoded by the following nucleotide sequence

[SEQ. ID. NO. 5]
gccctgtgtc gcccgcaggc ggcgcctacg ctgcggagcc ggaggagaac aagcggacgc gcacggccta cacgcgcgca cagctgctag agctggagaa ggagttccta ttcaacaagt acatctcacg gccgcgccgg gtggagctgg ctgtcatgtt gaacttgacc gagagacaca tcaagatctg gttccaaaac cgccgcatga agtggaaaaa ggaggaggac aagaagcgcg gcggcgggac agctgtcggg ggtggcgggg tcgcggagcc tgagcaggac tgcgccgtga cctccggcga ggagcttctg gcgctgccgc cgccgccgcc ccccggaggt gctgtgccgc ccgctgcccc cgttgccgcc cgagagggcc gcctgccgcc tggccttagc gcgtcgccac agccctccag cgtcgcgcct cggcggccgc aggaaccacg atgagaggca ggagctgctc ctggctgagg ggcttcaacc actcgccgag gaggagcaga gggcctagga ggaccccggg cgtggaccac ccgccctggc agttgaatgg ggcggcaatt gcggggccca ccttagaccg aaggggaaaa ccc The entire PDX1 sequence may be used in the fusion protein of the present invention. Alternatively, a fragment of the PDX1 having PDX1 activity (e.g., regulation of insulin transcription, regulation of PDX1 transcription, regulation of Nkx2.2 transcription) may be used. A non-limiting example of such a fragment would be a peptide sequence encompassing the homeobox domain and comprising the sequence:

[SEQ. ID. NO. 6]
NKRTRTAYTRAQLLELEKEFLFNKYISRPRRVELAVMLNLTERHIKIWF

QNRRMKWKKEE

The PDX1 peptide may contain conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain. Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse. Alternatively, the nucleotide sequence encoding PDX1 may contain alterations which produce silent substitutions, additions, or deletions, but do not alter the properties or activities of the encoded polypeptide. Nucleotide variants produced by silent substitutions due to the degeneracy of the genetic code are preferred.

The fusion protein or peptide may be obtained using recombinant DNA methods. For example, a nucleic acid sequence encoding PDX1 or PDX1 peptide may be inserted into a vector containing nucleic acid sequences encoding the TAT peptide. In a particular embodiment, the TAT sequence is obtained by PCR and inserted, for example, into a pET vector, or other protein expression vector capable of expressing a fusion protein. The fusion protein is expressed, isolated and purified using procedures known in the art, such as HPLC and column chromatography.

Alternatively, the fusion protein may be produced by solid phase synthesis using an organosynthesizer for peptide synthesis. The method is Merrifield solid-phase peptide synthesis (J. Am. Chem. Soc. 85, 2149-2154 (1963)). The peptide is synthesized by sequentially coupling an alpha-amino protected amino acid to an amino terminal of a peptide chain attached to a solid support resin after activation. After synthesis, the peptide is cut from the resin, and the protecting group is removed with a reagent such as trifluoroacetic acid (TPA). The peptide is separated from the TFA solution by filtration, centrifugation, or extraction with diethylether, and it can be purified by high performance liquid chromatography (HPLC) or other methods.

In addition, other TAT fusion proteins may be made. For example, TAT-PDX1, TAT-Hblx9, TAT-Ngn3, TAT-p48, or TAT-Foxa2 may be used in practicing the methods of the invention. Such fusion proteins made be made using the methods described above.

Uses of Pancreatic Progenitor Cells—

The pancreatic progenitor cells of the present invention and compositions thereof can be used therapeutically for treatment of various diseases associated with insufficient functioning of the pancreas. As used herein, the term "pancreatic disease" may include but is not limited to pancreatic cancer, insulin-deficiency disorder such as Insulin-dependent (Type 1) diabetes mellitus (IDDM) and Non-insulin-dependent (Type 2) diabetes mellitus (NIDDM), hepatitis C infection, exocrine and endocrine pancreatic diseases.

The progenitor cells of the present invention can be used to produce populations of differentiated pancreatic cells for repair subsequent to partial pancreatectomy, e.g., excision of a portion of the pancreas. Likewise, such cell populations can be used to regenerate or replace pancreatic tissue loss due to, pancreatolysis, e.g., destruction of pancreatic tissue, such as pancreatitis, e.g., a condition due to autolysis of pancreatic tissue caused by escape of enzymes into the tissue. Pancreatic cells may be transplanted into the pancreas or to ectopic sites, such as, but not limited to the liver, portal vein, spleen, mammary gland, kidney or at or near the intestines. In one embodiment the cells of the invention may be administered subcutaneously.

Methods of administration include encapsulating differentiated beta islet cells producing insulin in implantable hollow fibers. Such fibers can be pre-spun and subsequently loaded with the differentiated beta islet cells of the invention (see U.S. Pat. No. 4,892,538; U.S. Pat. No. 5,106,627; Hoffman et al. Expt. Neurobiol. 110:39-44 (1990); Jaeger et al. Prog. Brain Res. 82:41-46 (1990); and Aebischer et al. J. Biomech. Eng. 113:178-183 (1991)), or can be co-extruded with a polymer which acts to form a polymeric coat about the beta islet cells (U.S. Pat. No. 4,391,909; U.S. Pat. No. 4,353,888; Sugamori et al. Trans. Am. Artif. Intern. Organs 35:791-799 (1989); Sefton et al. Biotechnol. Bioeng. 29:1135-1143 (1987); and Aebischer et al. Biomaterials 12:50-55 (1991)).

The cells of the present invention may be genetically engineered to produce a particular therapeutic protein. As used herein the term "therapeutic protein" includes a wide range of biologically active proteins including, but not limited to, growth factors, enzymes, hormones, cytokines, inhibitors of cytokines, blood clotting factors, peptide growth and differentiation factors. Particular differentiated cells may be engineered with a protein that is normally expressed by the particular cell type. In a particular embodiment, pancreatic cells can be engineered to produce digestive enzymes.

Methods which are well known to those skilled in the art can be used to construct expression vectors containing a nucleic acid encoding the protein of interest linked to appropriate transcriptional/translational control signals and are described in more detail above.

The pancreatic progenitor cells and compositions, populations and cultures of the present invention may be used to determine if a test agent is toxic to a pancreatic cell by contacting the cells of the present invention with an appropriate amount of the test agent for a time sufficient for a toxic effect on the pancreatic cell to be detected and determining whether the test agent has a toxic effect on the pancreatic cell.

The pancreatic progenitor cells differentiated therefrom may also be used to humanize animal organs. Human amnion-derived cells may be similarly transplanted into another organ such as pancreas or brain or heart. The animal organ may or may not be depleted of its native cells prior to the transplant.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Preparation of Amnion-Derived Cell Compositions

Recovery of Amnion-Derived Cells—
Amnion-derived cells were dissociated from starting amniotic membrane using the dissociation agents PXXIII, and trypsin. The average weight range of an amnion was 18-27 g. The number of cells recovered per g of amnion was about $10\text{-}15 \times 10^6$ for dissociation with PXXIII and $5\text{-}8 \times 10^6$ for dissociation with trypsin.

Culture Conditions—
The primary amnion-derived cells were cultured for 5 passages in the following media: Stemline II+10% FBS, Stemline II+10% plasbumin (pb), Ultraculture+10% plasbumin (pb), and DMEM+10% FBS. Each culture condition was tested using 15 million cells/g amnion, 10 million cells/g amnion, and 5 million cells/g amnion, depending on the enzyme used for recovery of the primary cells. For instance, using PXXIII, 15 million cells/g amnion were obtained, while using trypsin, 10 million cells/g amnion were obtained, while other enzymes resulted in even lesser recovery (5 million cells/g amnion).

Passaging—
Cells were passaged 5 times as follows: The cells were grown attached to a culture flask (on tissue culture treated plastic). The cells were left to divide and grow. The cells were removed from the plastic using "tryple" (Gibco), a trypsin-like product that is animal-free GMP grade. Once unattached, the cells were centrifuged, and the cell pellet removed and resuspended in the culture medium with protein and additives (10 ng/ml EGF) and replated back onto fresh flasks. Cells were grown in a humidified atmosphere at 37° C. and 5% $CO_2$.

Results.
The results are show in Table 1 below. The data are reported as amnion-derived cells×$10^6$/gram of amnion.

TABLE 1

| Starting Isolation Efficiency | 5 mill/g | 10 mill/g | 15 mill/g |
|---|---|---|---|
| Stemline + 10% pb | 1363 | 2726 | 4089 |
| Stemline + 10% FBS | 1024 | 2048 | 3072 |
| Ultraculture + 10% pb | 575 | 1151 | 1726 |
| DMEM + 10% FBS | 128 | 256 | 384 |
| DMEM + 10% pb | 391 | 783 | 1174 |

The results indicate that the use of either Stemline or Ultraculture with added plasbumin (pb) or albumin, the primary cultures are expanded to a level that is at least 4 fold and as much as 10 fold higher than is obtained using previous methodology (DMEM with fetal bovine serum). Even the use of plasbumin (pb) in the basal media DMEM resulted in an expanded amnion-derived cell composition, having a 3-fold increase in multipotent cells as compared to the previous method of using DMEM with fetal bovine serum.

Another significant result observed was that cells grown in medium containing plasbumin displayed a spheroidal phenotype after passaging. When the amnion-derived cells were removed from the tissue culture surface with the digestive enzyme and replated, amnion-derived cells formed small clusters of cells that were not firmly adhered to the culture surface. Some of the clusters of cells were completely in suspension. These amnion-derived cell clusters proliferated until up to 200 cells were present in the clusters. After a period of 1-5 days, the clusters of cells reattached and flattened out to form an adherent monolayer. This clustering phenotype was observed at each passage. Further studies indicated that such clustering occurs in the following media containing either recombinant human albumin, plasbumin, or plasmanate: OptiPRO SFM, VP-SFM, Iscove's MDM, HPGM, UltraM-DCK, Stemline II and Stemline I, DMEM, and DMEM:F12, but not in Advanced DMEM, Knockout DMEM, 293 SFM II, Pro 293S-CDM, Pro 293A-CDM or Ultraculture VP-SFM.

Example 2

Scale-Up of Amnion-Derived Cells on Microcarrier Beads in Spinner Flasks

Methods—

One of the most common and oldest techniques for maintaining cells in suspension culture is by the use of spinner flasks. The cells can be either attached to microcarrier beads (adherent) or growing completely without any surface attachment (non-adherent). In either case, these flasks consist of a sterile vessel that contains a magnetic stirring mechanism that permits continuous stirring of the medium and cells under sterile conditions. This continuous stirring facilitates the diffusion of nutrients, promotes oxygenation of the medium, and eliminates concentration gradients. The vessels are stirred in a temperature-controlled, $CO_2$ incubator.

Amnion-derived cells are an epithelial cell type that are anchorage-dependent which may interfere with or prevent their adaptation to a pure suspension system. Although amnion-derived cells may survive in suspension culture, the proliferation of these cells may not be optimal without any substrate for attachment and/or many of the cells in suspension may undergo preliminary differentiation. One method of addressing this while maintaining the ability to grow the cells in a 3-dimensional system is to grow the cells on microcarrier beads. Microcarriers are typically small (30-1000 µm diameter) glass, polystyrene or dextran beads with a surface treatment to enhance attachment. The microcarriers provide the advantage of a very large surface area to which the cells attach allowing for culture at very high densities in a minimal volume of medium. For example, 1 gram dry weight of typical microcarriers is equal to 2000 $cm^2$ of surface area. A small number of microcarriers in cell culture medium can support the growth of significant numbers of anchorage-dependent cells.

Adherent Culture:

Amnion-derived cells isolated from 3 different placentas were placed into either spinner flasks with microcarrier beads (adherent cells) or normal T-flasks (control static adherent cells) and incubated at 37° C. at 5% $CO_2$ in air. The cells and beads were seeded into the spinner flasks at a ratio of 1 g of beads per 66×10^6 cells. 10×10^6 cells were plated into each T-flask. Periodically, cells were counted, and viability assessed, using a Guava PCA-96 Personal Cell Analyzer (ViaCount package). As little as 20 µl of sample was used for this analysis. A graph of total and viable cell counts per ml was blotted with time to ensure that the cells were able to divide and remain viable over time in culture.

Results—

In all three experiments, amnion-derived cells were shown to be capable of proliferating to at least 1.5 times seeding density, thus demonstrating that microcarrier bead spinner flask culture methods are a feasible alternative to static culture.

Example 3

Scale-Up of Amnion-Derived Cell Compositions in Suspension

Amnion-derived cells were cultured in ultra-low adherence tissue culture 6-well plates (Corning) in various mammalian cell culture media. These culture media were selected on the basis of their ability to promote proliferation of other mammalian cell types in suspension culture (i.e. 293S, Ultraculture, Opti-MEM). Additives to the culture medium in these experiments include a proprietary source of protein, and EGF (10-20 ng/ml) which preliminary experiments show is required for proliferation of amnion-derived cells. Amnion-derived cells were plated at a density of $1.3×10^6$ cells/well, and the cultures were maintained at 37° C., in 5% $CO_2$ in air. Culture medium was replaced every two days and cell number was assessed weekly. Preliminary experiments showed that amnion-derived cells sometimes form small floating clusters in suspension culture conditions. These clusters must be dispersed to ensure accurate cell counts and this was achieved by incubating the cultures in trypsin for 5-10 minutes prior to counting. Cells were counted, and viability assessed, using a Guava PCA-96 Personal Cell Analyzer (ViaCount package). As little as 20 µl of sample was used for this analysis. A graph of total and viable cell counts per ml was plotted with time to ensure that the cells were able to divide and remain viable over time in culture. Cells were subcultured at $1.3-1.5×10^6$ cells per well. The cultures were maintained until proliferation ceased. Control adherent cultures were maintained on tissue culture treated 6-well plates to compare rates of proliferation between adherent and suspension culture. Cultures were maintained at 37° C., in 5% $CO_2$ in air. Passage of adherent cells was performed at confluency. Adherent cultures were trypsinized and washed before replating at $1.3×10^6$ cells/well. Cell counts and viability were measured in the adherent cells at each passage. Culture media was tested on 5 different donor tissues to account for tissue variability.

Results:

Of the 5 placentas tested, 4 showed at least 2 fold proliferation at least through day 20 under all conditions tested, thus demonstrating that non-adherent static culture methods are a feasible alternative to microcarrier bead or adherent flask culture.

Example 4

Addition of Growth Factor Additives to Promote More Extensive Proliferation

After selection of a culture medium that supports suspension culture in 6-well plates, various growth factor additives are tested to promote more extensive proliferation in suspension culture conditions. These growth factors include EGF, IGF-1, IGF-II, αFGF, αFGF-h, βFGF, FGF-4, FGF-8, KGF, SCF, Fsk, SHh, Prog, Wnt-1, CT, VPA. These and other factors known to either promote cell proliferation or decrease apoptosis or anoikis are tested at various concentrations in the suspension cultures to determine their effect on proliferation.

Additional testing is performed to ensure that these factors are not promoting differentiation or changing the secretory profile of the cells.

Example 5

Culturing of Amnion-Derived Cells in Spinner Flasks or Roller Bottles without Microcarrier Attachment After selection of a culture medium that supports proliferation of amnion-derived cells in suspension, with or without the addition of growth factors other than EGF, experiments are performed to assess the proliferation of the cells in a stirred bioreactor. Amnion-derived cells are placed into the spinner flasks (suspension cells; $3 \times 10^5$ cells/ml). Adherent cells cultured in T-flasks are used as controls (adherent cells; $1.3 \times 10^5$ cells/cm$^2$). All cultures are incubated at 37° C. in 5% $CO_2$ in air. The spinner flasks are treated with Sigmacote (Sigma-Aldrich) prior to use, to prevent the cells from attaching to the glass. The flasks are agitated by placing them on magnetic stir-plate. Daily samples of cells are withdrawn, in a class II biosafety cabinet, from each spinner flask, and the number of cells is counted, and viability assessed, using a Guava PCA-96 Personal Cell Analyzer (ViaCount package). The use of multiple spinner flasks permits the use of 2 or 3 replicates of each condition per experiment.

One of the challenges of a spinner flask system is the exposure of the cells to sheer forces caused by the rotating impeller. A gentler alternative to spinner flasksis to culture the cells in roller bottles. Tissue culture treated roller bottles (1.2 L; Corning) are pre-treated with poly 2-hydroxyethyl methacrylate (Poly-Hema) to prevent cell attachment. Roller bottles containing 30-40×10$^6$ amnion-derived cells are placed on a roller bottle apparatus (Integra Biosciences). Cells are sampled on a biweekly basis and assessed for viability and proliferation, as indicated above.

Example 6

Generation of Monoclonal Antibodies

In one embodiment, Balb/c mice are immunized with amnion-derived cells previously cultured for up to 5 days, preferably 1-2 days. In this embodiment, both adherent and non-adherent cells are recovered from the culture and used to immunize the mice. In another embodiment, after culturing for up to 5 days, preferably 1-2 days, only the adherent cells are recovered and used for immunization of the mice. In another embodiment, after culturing for up to 5 days, preferably 1-2 days, only the non-adherent cells are recovered and used for immunization of the mice. Four to six weeks after immunization, the spleens are removed and the spleen cells are fused to a mouse myeloma cell line, SP2/0-Ag14, using techniques known in the art, resulting in the generation of viable hybridoma cells. As many as 1000 hybridomas may be expanded, screened for the expression of monoclonal antibodies, and further tested for their specific reactivity to cell-surface protein markers on amnion-derived cells. Antibody samples are analyzed by flow cytometry and, along with commercially available antibodies, will be used to identify unique protein markers on amnion-derived cells. Thus, the invention is directed to hybridomas producing the monoclonal antibodies of the present invention as well as the monoclonal antibodies.

Example 7

Antibodies which React with Amnion-Derived Cell Surface Protein Markers

Monoclonal antibodies which react with amnion-derived cell protein markers on the surface of amnion-derived cells may be used to separate the cell population into substantially purified population of amnion-derived cells and will be useful in characterizing each substantially purified population of amnion-derived cells for its stem cell characteristics. The monoclonal antibodies of the present invention may be used to isolate a stem cell protein marker unique to the substantially purified population of amnion-derived cells. The newly identified protein marker may be used to isolate a nucleic acid sequence encoding the protein. Thus, the invention is directed to unique markers on amnion-derived cells, the isolated protein marker, the isolated nucleic acid encoding the protein marker, as well as expression vectors capable of expression the protein marker when transfected into mammalian cells such as CHO, COS, etc. The invention is further directed to bacterial cells carrying the vector for vector propagation.

In addition, the invention contemplates using known antibodies to identify and create substantially purified populations of amnion-derived cells having unique combinations of markers useful as identifying characteristics of the substantially purified populations. This unique combination of markers can be used to isolate, characterize, purify or create a substantially purified population of amnion-derived cells having those characteristics.

All cell characterizations described herein were done using freshly isolated amnion-derived cells. One of skill in the art will recognize that the expression pattern of the markers may vary depending upon culture conditions and time in culture. For example, the protein marker expression pattern seen in the expanded populations of the invention described herein may be different from that seen in freshly isolated amnion-derived cells. In addition, one of skill in the art will recognize that the order in which the cells are contacted with the antibodies is not critical to obtaining the desired populations of amnion-derived cells. Table 2 shows the results of FACS analysis of amnion-derived cells freshly isolated from the amnion of a placenta. The antibodies used, alone or in combination, may be useful to identify, characterize or create a substantially purified population of amnion-derived cells. One preferred embodiment is the use of anti-CD90 and anti-CD117 antibodies to identify, isolate, characterize or create a substantially purified population of amnion-derived cells. Other preferred embodiments for identifying, isolating, characterizing or creating substantially purified populations of amnion-derived cells include contacting the cells with anti-CD90, anti-CD117, and anti-CD105 antibodies; contacting the cells with (i) anti-CD90, anti-CD117, and anti-CD105 antibodies and (ii) with at least one antibody selected from the group consisting of anti-CD140b, anti-CD34, anti-CD44, and anti-CD45 antibodies; contacting the cells with (i) anti-CD90 and anti-CD117 antibodies and (ii) with an anti-CD29 antibody; contacting the cells with (i) anti-CD90, anti-CD117 and anti-CD105 antibodies and (ii) with an anti-CD29 antibody; contacting the cells with (i) anti-CD90, anti-CD117 antibodies and (ii) anti-CD29 antibodies and (iii) with one or more antibodies selected from the group consisting of anti-CD9, anti-CD10, anti-CD26, anti-CD71, anti-CD166, anti-CD227, anti-EGF-R, anti-SSEA-4, and anti-HLA-G antibodies; contacting the cells with (i) anti-CD90, anti-CD117, and anti-CD105 antibodies and (ii) and anti-CD29 antibodies and (iii) with one or more antibodies selected from the group consisting of anti-CD9, anti-CD10, anti-CD26, anti-CD71, anti-CD166, anti-CD227, anti-EGF-R, anti-SSEA-4, and anti-HLA-G antibodies; contacting the cells with (i) anti-CD90, anti-CD117, and anti-CD105 antibodies and (ii) and anti-CD29 antibodies and (iii) with one or more antibodies selected from the group consisting of anti-CD140b, anti-CD34, anti-CD44, and anti-CD45 antibodies; b) contacting the cells with (i) anti-CD90, anti-CD117, and anti-CD105 antibodies and (ii) and anti-CD29 antibodies and (iii) one or more antibodies selected from the group consisting of anti-CD140b, anti-CD34, anti-CD44, and anti-CD45 antibodies and (iv) one or more antibodies selected from the group consisting of anti-CD9, anti-CD10, anti-CD26, anti-CD71, anti-CD166, anti-CD227, anti-EGF-R, anti-SSEA-4, and anti-HLA-G antibodies; and contacting the cells with one or more antibodies selected from the group consisting of anti-CD90, anti-CD117, anti-CD140b, anti-CD34, anti-CD44, and anti-CD45 antibodies; and one or more antibodies selected from the group consisting of anti-CD29, anti-CD9, anti-CD10, anti-CD26, anti-CD71, anti-CD166, anti-CD227, anti-EGF-R, anti-SSEA-4, and anti-HLA-G antibodies.

TABLE 2

| Population % | Designation | Surface Marker | | | |
|---|---|---|---|---|---|
| ~95-100% | +++ | CD9 | CD29 | | |
| ~70-95% | ++ | SSEA4 | CD10 | CD166 | CD227 |
| ~60-95% | + | HLA-G | EGFR | CD26 | |
| ~10-50% | +/− | CD71 | | | |
| <1% | − | CD34 | CD44 | CD45 | CD140b |
| | | CD90 | CD105 | CD117 | |

Table 3 shows where antibodies useful for practicing the methods of the invention can be obtained.

TABLE 3

| Antibody Name | Manu. | Cat. # |
|---|---|---|
| CD117 PE | BD-Pharm | 555714 |
| CD44 PE | BD-Pharm | 555479 |
| CD45 PE | BD-Pharm | 555483 |
| EGFR PE | BD-Pharm | 555997 |
| CD105 FITC | Chemicon | CBL418F |
| CD117 APC | BD-Pharm | 550412 |
| CD29 APC | BD-Pharm | 559883 |
| CD34 APC | BD-Pharm | 555824 |
| CD227 | BD-Pharm | |
| CD44 APC | BD-Pharm | 559942 |
| CD45 APC | BD-Pharm | 555485 |
| CD140b PE | BD-Pharm | 558821 |
| CD90 Biotin | BD-Pharm | 555594 |
| CD26 | BD-Pharm | |
| CD166 | BD-Pharm | |
| CD10 | BD-Pharm | |
| CD71 | BD-Pharm | |
| CD9 | BD-Pharm | |

Example 8

Generation of Enriched Populations of Amnion-Derived Cells

Amnion-derived cell protein markers expressed on the cell surface may be used to enrich for populations of amnion-derived cells expressing those protein markers using a variety of methods. Such procedures may involve a positive selection, such as passage of sample cells over a column containing anti-protein marker antibodies or by binding of cells to magnetic bead-conjugated antibodies to the protein markers or by panning on plates coated with protein marker antibodies and collecting the bound cells. Alternatively, a single-cell suspension may be exposed to one or more fluorescent-labeled antibodies that immuno-specifically bind to amnion-derived cell protein markers. Following incubation with the appropriate antibody or antibodies, the amnion-derived cells are rinsed in buffer to remove any unbound antibody. Amnion-derived cells expressing the protein marker(s) can then be sorted by fluorescence-activated cell sorting (FACS) using, for example, a Becton Dickinson FACStar flow cytometer. To enrich for populations of cells expressing a desired protein marker(s), the cells may be subjected to multiple rounds of FACS sorting.

In addition, protein markers that are not expressed on the surface of amnion-derived cells may also be used to enrich for populations of amnion-derived cells not expressing those markers. Such procedures may involve a negative selection method, such as passage of sample cells over a column containing anti-protein marker antibodies or by binding of cells to magnetic bead-conjugated antibodies to the protein markers or by panning on plates coated with protein marker antibodies and collecting the unbound cells. Alternatively, a single-cell suspension may be exposed to one or more fluorescent-labeled antibodies that immuno-specifically bind to the protein markers. Following incubation with the appropriate antibody or antibodies, the cells are rinsed in buffer to remove any unbound antibody. Cells expressing the protein marker(s) can then be sorted by fluorescence-activated cell sorting (FACS) using, for example, a Becton Dickinson FACStar flow cytometer and these cells can be removed. Remaining cells that do not bind to the antibodies can then be collected. To enrich for populations of cells that do not express a desired protein marker(s), the cells may be subjected to multiple rounds of FACS sorting as described above.

Non-limiting examples of antibodies that may be useful to generate such enriched populations of amnion-derived cells include anti-CD10, anti-CD26, anti-CD71, anti-CD166, anti-CD227, anti-EGF-R, anti-SSEA-4, and anti-HLA-G antibodies.

Alternatively, antibodies may be useful to generate enriched populations of amnion-derived cells by removing undesired cells (i.e. by conjugating antibodies to beads and adding the beads to a culture dish containing a heterogeneous population of amnion-derived cells such that cells in the heterogeneous population that express the marker to which the antibody is directed will bind to the beads thus removing them from the population of cells that do not express the marker). Non-limiting examples of antibodies that may be useful in this process anti-CD140b, anti-CD34, anti-CD44, and anti-CD45, anti-CD90, anti-CD105, and anti-CD117 antibodies.

Example 9

Monoclonal Antibody Library

To construct a "monoclonal antibody library" a collection of several monoclonal antibodies may be selected which identifies and isolates the particular cell population responsible for the multipotent cell activity characteristic of the population of amnion-derived cells of the present invention. The panel of monoclonal antibodies may be reacted with placental tissue, a placental-derived cell suspension, or a culture of placental-derived cells. Cells reacting with the collection of monoclonal antibodies may be identified and isolated using methods known in the art, e.g., FACS. The invention is therefore directed to a collection of monoclonal antibodies that are used to form a monoclonal antibody library.

Example 10

Use of Amnion-Derived Cell Compositions in Wound Healing

Methods.

The keratinocyte cell line isolated from epidermis (ATCC CRL-1555) was seeded onto 6-well plates at a density of $0.3 \times 10^6$ cells per well. Cells were left to grow to confluency then placed into serum-free conditions for 48 hours. In each well a scrape or wound of the confluent monolayer was made from the top to the bottom of the well using a 1 ml pipette tip. Images of the scrape were taken at 0, 24, 30 and 48 hours to determine cell migration or percent of wound closure in response to addition of conditioned medium to each well. Conditions tested were 0%, 50%, and 100% of the following: 1) No conditioned media (control, 0%); 2) Conditioned media from amnion-derived cells passaged normally at ratio of 1:3; 3) Conditioned media from amnion-derived cells that were never passaged; 4) Conditioned media from amnion-derived cells grown in the ATCC cells' media; and 5) Conditioned media from ATCC cells grown in their own media. Approximately 6 measurements were taken in microns of each scrape at each time point using phase microscopy and MetaMorph imaging software. The percent of healing was calculated by comparing the width of each wound at 24, 30, and 48 hours to the starting width of the wound at time zero.

Results.

Conditioned media (CM) from amnion-derived cells showed a significant increase in cell migration or healing of the scrape compared to control. CM from other cell types, however, did not show this increase. Cells that grew in CM from amnion-derived cells were the only condition that showed complete closure of the scrape before 24 hours. CM from cells passaged at a ratio of 1:3 and at a concentration of 50% (CM/non-CM) produced the best results. These results suggest that components of CM from amnion-derived cells have properties that increase cell migration or wound healing.

Example 11

Amnion-Derived Cells, Conditioned Media, and Cell Lysates Accelerate Re-Epithelialization, Collagen Synthesis, and Regain to Tissue Tensile Strength The following experiment was done to assess whether the application of amnion-derived cells, amnion-derived cell conditioned media or amnion-derived cell lysates could: 1) accelerate the rate of re-epithelialization, 2) accelerate collagen synthesis and deposition in the wound bed and 3) speed up regain to tissue tensile strength and demonstrate that transplantation of stem cells may have the same properties. It was also done to assess whether transplanted amnion-derived cells could incorporate into epidermal and dermal structures including follicles, glands and blood vessels.

Animal Model:

This initial study utilized a total of 90 rats, distributed into the following groups (5 sacrifice time points, 3 animals per treatment group, 6 groups per time point), Table 4.

TABLE 4

| Group # | Treatment | Time Points (days) | | | | |
| --- | --- | --- | --- | --- | --- | --- |
| | | 3 | 5 | 7 | 14 | 21 |
| 1 | Control (no treatment) | 3 | 3 | 3 | 3 | 3 |
| 2 | Non-conditioned media + gelfoam | 3 | 3 | 3 | 3 | 3 |
| 3 | Amnion-derived cell conditioned media + gelfoam | 3 | 3 | 3 | 3 | 3 |
| 4 | Hyaluronic acid vehicle | 3 | 3 | 3 | 3 | 3 |
| 5 | Amnion-derived cell + hyaluronic acid vehicle | 3 | 3 | 3 | 3 | 3 |
| 6 | Amnion-derived cell lysate + hyaluronic acid vehicle | 3 | 3 | 3 | 3 | 3 |

Each animal received 2 dorsal, full-thickness excisional wounds, for a total of 180 wounds for the entire study, with 6 wounds/group/time point.

Skin Wounding:

A pair of wounds was made on each side of the dorsal midline, using a disposable punch biopsy (6 mm diameter) These wounds were full-thickness through the epidermis and dermis. Wounds were treated with: nothing (control), vehicle (10 mm Gelfoam sponge saturated with non-conditioned media), conditioned media (10 mm Gelfoam sponge saturated with amnion-derived cell conditioned media), hyaluronic acid vehicle (0.1 ml of Hylan A gel, Genzyme Corporation), hyaluronic acid+fluorescently (CM-DiI dye, Molecular Probes, Eugene Oreg.) labeled amnion-derived cells ($10^6$ cells/wound) or hyaluronic acid+amnion-derived cell lysate (from $10^6$ cells/wound), immediately following injury (See above Table 5). The entire dorsal skin was covered with a sterile dressing (Tegaderm, 3M, Minneapolis, Minn.) secured with a biocompatible adhesive (Mastisol, Ferndale Laboratories Inc, Ferndale, Mich.). Wounds in the first three treatment groups were re-treated in an identical manner on days 2, 3, 4 and 5 post wounding. Following the 5th wound treatment, the wounds were left undisturbed until day 7, at which time the Gelfoam as well as the sterile dressing was removed and the wound allowed to heal exposed to the surrounding environment. Wounds in the last three treatment groups were left undisturbed until time of sacrifice.

Imaging and Clinical Assessment:

Two blinded observers assessed the degree of wound healing for each of the 180 wound samples at the following days post injury: 1, 2, 3, 4, 5, 7, 14 and 21. The following parameters were ascertained: hemostasis, wound contraction, re-epithelialization and inflammation. Digital images were taken of representative wound samples for each treatment group and stored for later analysis.

Tissue Analysis:

Animals were be euthanized according to the above time table by intracardiac administration of pentobarbital sodium and phenyloin sodium following heavy sedation with ketamine/xylazine. Dorsal skin was removed using aseptic technique and each wound was individually dissected and divided. One half of each wound was used for tensile strength measurements, with the other embedded for frozen sectioning and image analysis.

Tensiometry:

Wound samples from the day 7, 14 and 21 groups were analyzed by tensiometry. For tensile strength measurements the frozen specimens were trimmed of sub-cutaneous fat and any muscle that was taken along with the biopsy, and divided into 4-5 samples. The cross-sectional area of each specimen was measured with calipers. Then the specimen was clamped in the tensiometer, and force exerted until the skin teared. Measurements were recorded by a computer and tensile strength calculated using the formula: Maximum Tensiometer Reading (converted to g) divided by Cross-sectional Area (sq-mm)=Tensile strength (g/sq-mm). The results for individual specimens from one wound were combined to determine an average TS/wound (tensile strength per wound). This value was normalized for the TS/skin (tensile strength of uninjured skin from the opposite side); TS/wound divided by TS/skin=relative TS/wound. The relative TS/wound was tabulated for each group at each time point and the mean and standard deviations determined using Excel database software (Microsoft Office 2000).

Microscopic Analysis:

Tissue specimens were embedded in O.C.T. (Miles, Inc., Elkhart, Ind.) and cryostat-sectioned into approximately 10 μm thick sections, at −23° C. Thin sections, mounted on glass microscope slides, were stored in moisture-proof slide boxes at −70° C. Representative slides were processed for immunohistochemical characterization of the connective tissue components using standard techniques. Hematoxylin and eosin staining were used to ascertain the overall histological appearance of the injured mucosa. Collagen presence in the wound was assayed using Masson's trichrome stain. Picrosirius-polarization method was used to analyze collagen fiber organization. Grafting and survival of fluorescently labeled stem cells in the wound bed was semi-quantitatively analyzed by measuring the total amount of fluorescence present in the wound bed. Localization of cells was recorded and analyzed.

Effect on the rate of wound re-epithelialization and dermal collagen deposition and organization was determined. Each of these, as well as other components of the wound healing process, were analyzed using specific markers. Transplantation of live amnion-derived cells into the dermal wound bed was expected to result in: 1) differentiation and engrafting of stem cells into various skin compartments and 2) continual regulated release of various stem cell factors.

Results—

The results of this experiment are set forth in Table 5 below.

TABLE 5

| Summary | Amnion-derived cell conditioned medium | Amnion-derived cells |
|---|---|---|
| Positive Effects | 1. Day 5: CM wounds, >contracted granulation formation 2. Day 14: CM wounds appeared smaller, >contracted, >healed 3. CM wounds exhibited faster re-epithelialization and angiogenesis. | 1. Re-Epithelialization in early time points 2. Angiogenesis in early time points 3. Dynamics of collagen deposition and organization |
| Negative Effects | None | No detection of engrafted cells |
| Unaltered | 1. Synthesis and deposition of collagen 2. Regain of tissue tensile strength | 1. Clinical observations 2. Regain of tissue tensile strength |

As shown in Table 5, treatment of wounds with amnion-derived cell conditioned media showed an increase in contracted granulation formation by Day 5, and smaller wounds, greater contraction and healing by Day 14. In addition, the wounds exhibited faster re-epithelialization and angiogenesis as compared to controls. Synthesis and deposition of collagen and regain of tissue tensile strength were unaltered over the course of the experiment. Treatment of wounds with amnion-derived cells showed re-epithelialization and angiogenesis at early time points, as well as evidence of collagen deposition and organization. Engrafted cells were not detected. No differences based on visual inspection in clinical observations (redness, swelling, size, etc.) were seen nor was regain of tissue tensile strength altered over the course of the experiment.

Example 12

Detection of Cytokines in Conditioned and Unconditioned Media Samples

In addition to pluripotency, amnion-derived cells may play a significant role in the inflammatory response. In the early phases of wound healing, chemokines and cytokines regulate chemotaxis and activation of inflammatory cells. Growth factors play dominant roles in regulating cell proliferation, differentiation, and synthesis of extracellular matrix. Amnion epithelial cells have been shown to secrete many cytokines and growth factors. These factors include prostaglandin E, PDGF, TGF-α, EGF, IL-4, IL-8, TNF, interferons, activin A, noggin, b-FGF, angiogenic factors, and other neuroprotective factors (Koyano, S., et al., (2002) Dev Growth Differ 44, 103-12; Blumenstein, M., et al., (2000) Placenta 21, 210-7; Tahara, M., et al., (1995) J Clin Endocrinol Metab 80, 138-46; Paradowska, E., et al., (1997) Placenta 18, 441-6; Denison, F. C., et al., (1998) Hum Reprod 13, 3560-5; Keelan, J. A., (1998) Placenta 19, 429-34; Sun, K., et al., (2003) J Clin Endocrinol Metab 88, 5564-71; Uchida, S., et al., (2000) J Neurosci Res 62, 585-90).

Many of these cytokines are associated with wound healing and some have been credited with contributing to scarless healing in the fetus (Robson, M. C., et al., (2001) Curr Probl Surg 38, 72-140; Ferguson, M. W. et al., (2004). Philos Trans R Soc Lond B Biol Sci 359, 839-50).

To determine which of these cytokines may be secreted by the amnion-derived cells of the present invention, conditioned media from amnion-derived cells was isolated from cell cultures that were seeded onto tissue culture treated flasks at a density of ~40,000 cells per $cm^2$. Cells were cultured in a proprietary serum-free medium supplemented with 10 ng/ml of EGF. Culture media was exchanged every 2 days during the growth period. After cells reached near confluency (~1-2 wk after isolation), fresh media was applied and conditioned media was collected after three days and stored at −80 C for subsequent analysis.

Conditioned media was analyzed for secreted protein content via antibody arrays for multiple protein detection (RayBiotech, Norcross, Ga. using RayBio® Human Cytokine Antibody Arrays V, VI, and VII). The samples that were analyzed are shown in Table 6 below.

TABLE 6

1. Complete unconditioned media + plasbumin
2. Complete unconditioned media + EGF (no plasbumin)
3. Conditioned media from placenta 1 + plasbumin
4. Conditioned media from placenta 1 (no plasbumin)
5. Conditioned media from placenta 2 + plasbumin Results—
Table 7 provides the results of this experiment.

TABLE 7

| Wound Healing Relevant Cytokines | |
|---|---|
| Positive in Conditioned Media | Negative |
| Angiopoietin-2, Angiogenin, bFGF, EGF, FGF-7, FGF-4, IGF-1, IL-1 beta, IL-2, IL-4, IL-6, IL-8, IL-10, PDGF-AA, PDGF-AB, PDGF-BB, PDGF-Ra, PDGF-Rb | TGF-a, TGF-beta 1, TGF-beta 2, TGF-beta 3 |

Example 13

Amnion-Derived Cell/Fibroblast Co-Cultures

It has been reported in the literature that under certain conditions when ES cells are co-cultured with fibroblasts, the ES cells are induced to differentiate into keratinocyte-like cells. To determine what effect co-culture of amnion-derived cells with fibroblasts would have on amnion-derived cells, an experiment was done in which $3.3 \times 10^6$ amnion-derived cells were co-cultured with $0.4 \times 10^6$ fibroblasts on a collagen IV-coated T25 flask for 3, 5, 10, 15, and 25 days.

Results—

When treated with the trypsin-like enzyme Tryple (Invitrogen), both amnion-derived cell cultures and fibroblast cell cultures alone release cells as a single cell suspension. However, when the amnion-derived cell/fibroblast co-culture was treated with Tryple, the cells came off the treated culture surface as sheets rather than as a single cell suspension. Furthermore, the sheets were very stable and somewhat resistant to enzymatic and mechanical disruption.

It is theorized that these sheets may be suitable for use as wound dressings when it is desirable to have a dermal-type graft. With demonstrated recent success with mitral resuscitation, management of inhalation injuries, control of burn wound sepsis, and understanding of the hypermetabolic response, early excision and rapid closure of the burn wound with a serviceable integument becomes a therapeutic imperative. In small surface area burns, this can be accomplished by autogenous skin grafts. For large surface area burns, both partial and full-thickness, there is not yet a totally satisfactory solution. Cutaneous epithelial autografts can be grown from the patient's skin and massively expanded to cover the entire body. Unfortunately, the lack of dermis leads to prolonged fragility and significant scarring, therefore, many believe that a "dermis" is required along with an epithelium.

Recent products with a supposed dermal substitute or neodermis such as Integra, Alloderm, Transcyte, Apligraf, and Dermagraft have attempted solve the problem. However, all of these "skin" substitutes have the problem of being expensive and having lower resistance to infection than autografts. Without a satisfactory rapid reliable wound closure for burn injuries, the wound remains in the inflammatory phase of healing for a prolonged period of time resulting in excessive scarring.

Robson et. al., (Robson, M. C., and Krizek, T. J. (1973) *Ann Surg* 177, 144-9) reported success in treatment of experimental and clinical burns (both partial and full thickness) using human amniotic membranes. It was thought that part of the effect seen from the treatment with amniotic membranes was due to a humoral substance or substances stimulating wound healing. These observations were prior to present knowledge of cytokines and growth factors. More recently, attempts have been made to use recombinant growth factors and growth hormones to affect more rapid healing of the burn wound. Amniotic membranes proved not to be practical because of the risk of virally transmitted diseases. However, the observations from those early experiments and coupled with new knowledge support the possibility that the pluripotentiality of amnion-derived cells and their now demonstrated protein secretory profile of cytokines and other humoral substances stimulatory for wound healing may be useful in providing rapid early closure for thermal injuries.

Example 14

Effects of Amnion-Derived Cell Conditioned Media in an Animal Model of Acute Wound Healing An animal model of acute excisional granulating wound was used to evaluate the effect of amnion-derived cell conditioned media on wound healing.

Methods:

Acute excisional granulating wound model: Twenty male Sprague-Dawley rats weighing 250-300 g were anesthetized using ketamine (40 mg/kg), xylazine (10 mg/kg) and acepromazine (0.75 mg/kg). Following anesthesia, the dorsum of each animal was depilated and four symmetrical midline areas 1.5×1.5 cm were traced on the skin using a copper template. Four wounds were then created by excision of the marked areas through the skin and the panniculus carnonsus muscle. The animals were divided into the following groups of 5 (Table 8):

TABLE 8

| Group No. | Experimental Conditions |
|---|---|
| I | Conditioned media, non-infected |
| II | Unconditioned media, non-infected |
| III | Conditioned media, infected |
| IV | Unconditioned media, infected |

Analog tracings were made every 72 hours onto acetate sheets of both open wound areas and of the advancing full-thickness skin edges of all wounds. To eliminate site-related variability in the wounds, only the three caudal wounds were measured for statistical purposes, since the most cephalad wound has been shown to demonstrate different healing characteristics. Wound area calculations were performed with the use of digital planimetry (Sigma Scan; Jandel Scientific, Corte Modera, Calif.). Weekly quantitative bacterial analyses were performed on a subset of wounds in each group and are expressed as CFUs/g of tissue.

After all four wounds of each animal were completely epithelialized as determined by visual inspection, the animals were euthanized and the entire dorsum of the rat including the panniculus carnosus was removed. A 1 cm wide skin strip perpendicular to each resultant scar, was harvested for breaking strength analysis. An Instron tensiometer (Model No. 4201; Instron Corp., Canton, Mass.) with a 5 kg tension load cell and cross head speed of 10 mm/min was used. Breaking strength is defined as the force required to rupture the scar and is reported in kilograms.

Results—

Figure 2:
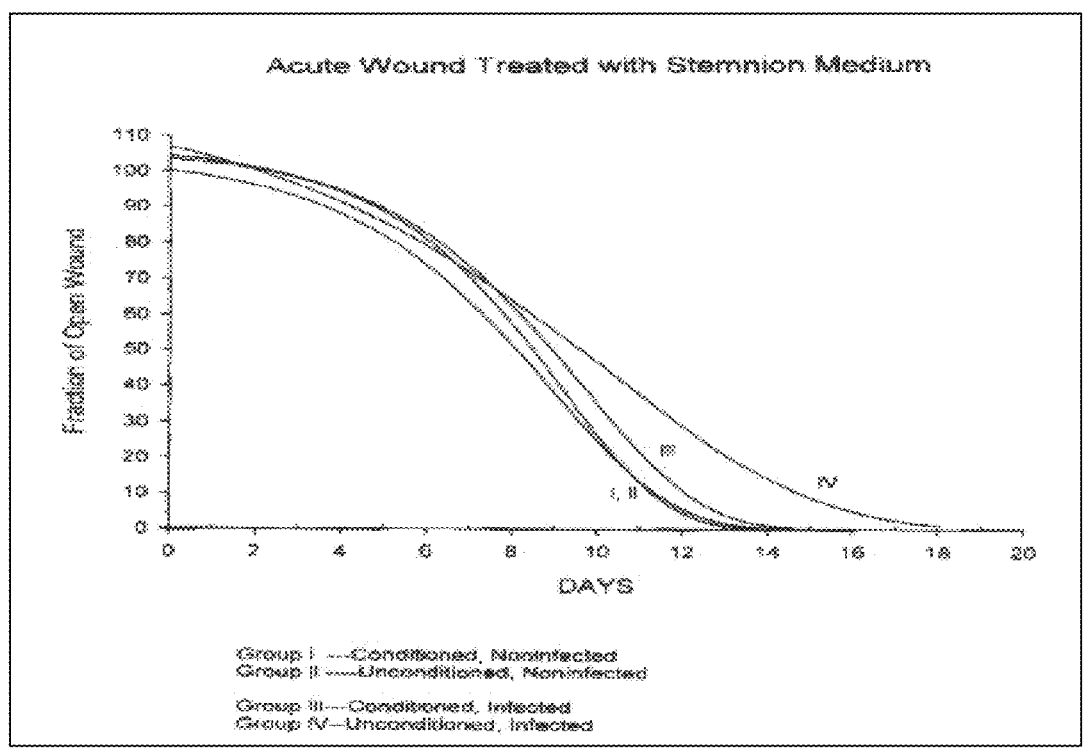
FIG. 2—The application of conditioned media overcomes the inhibition of wound healing caused by bacteria and shifts the healing trajectory in contaminated wounds to that of near normal healing.

The application of conditioned media overcomes the inhibition of wound healing caused by bacteria and shifts the healing trajectory in contaminated wounds to that of near normal healing (FIG. 2).

Example 15

Effects of Amnion-Derived Cell Conditioned Media in an Animal Model of Chronic Wound Healing Methods:

Chronic granulating wound model: Twenty male Sprague-Dawley rats weighing 300-350 g are anesthetized using ketamine (40 mg/kg), xylazine (10 mg/kg) and acepromazine (0.75 mg/kg). Following anesthesia, the dorsum of each animal is shaved and depilated. A full-thickness dorsal burn measuring 30 cm$^3$ is created by immersion in boiling water.

Animals in the contaminated group are seeded with 5×10^8 *Escherichia coli* ATCC #25922 after the rats have been allowed to cool for 15 minutes. Bacteria is obtained from fresh 18 hour broth culture and inoculum size is confirmed by backplating. The animals are divided into 8 equal groups of 5 for different treatments after the day 5 escharectomies.

Animals are individually caged and given food and water ad libitum. Five days after burning, the eschar is excised from anesthetized animals, resulting in a chronic granulating wound. Histological characteristics of this wound with comparison to human granulating wound have been previously performed. The wounds are treated with the same experimental groups as described in Table 9 above. Any dried exudates that form are atraumatically removed prior to wound tracings or biopsies. Every 72 hours the outlines of the wounds are traced onto acetate sheets and area calculations are performed using digital planimetry. Care is taken only to record the advancing full-thickness margin rather than any advancing edge of epithelium. This avoids the small component of advancement provided by the smooth, pink, translucent, hairless neoepithelium. Serial area measurements are plotted against time. For each animal's data, a Gompertz equation is fitted (typical r2=0.85). Using this curve the wound half-life is estimated. Comparison between groups is performed using life table analysis and the Wilcoxon rank test. The statistical analysis is done using the SAS (SAS/STAT Guide for Personal Computers, Version 6 Edition, Cary, N C, 1987, p. 1028).

Example 16

Effects of Amnion-Derived Cells in Two Animal Models of Wound Healing

The two animal models of granulating wounds described above in Examples 14 and 15 are used to evaluate the effect of amnion-derived cells on wound healing. The experimental groups are as follows in Table 9.

TABLE 9

| Group No. | Experimental Conditions |
| --- | --- |
| I | Non-contaminated control (PBS only) |
| II | Contaminated control (PBS + bacteria) |
| III | Non-contaminated treated with cells |
| IV | Contaminated treated with cells |

Example 17

Ability of Amnion-Derived Cells to Promote Complete Regeneration of Deep Wounds

Experiments are designed to promote complete regeneration of deep wounds through re-creating the all of the necessary tissues including bone, muscle, cartilage, skin, and neural tissue. Initially, in vitro experiments are designed to determine if amnion-derived cells can differentiate into all of the cells of interest. Amnion-derived cells will be cultured as previously described. Mesenchymal stem cells (Cambrex, Rutherford, N.J.) will be used as a control for differentiation experiments. MSC's will be seeded at 5,000-6,000 cells per $cm^2$ and cultured in Mesenchymal Stem Cell Growth Medium (MSGM, Cambrex, Rutherford, N.J.).

Osteogenic:

Once cells are confluent, growth media will be changed (DMEM, 10% FBS, 1% pen/strep) to osteogenic differentiation media (Shi, Y. Y., et al., (2005) *Plast Reconstr Surg* 116, 1686-96) (DMEM, 10% FBS, 1% pen/strep, 250 uM ascorbate-2-phosphate, 10 mM beta-glycerophosphate, 2.5 uM retinoic acid). Osteogenic differentiation media will be changed every 2-3 days. Alkaline phosphatase activity of adipose-derived mesenchymal cells will be evaluated in duplicate wells after 7 days of culture. Alkaline phosphatase staining will be performed using the Alkaline Phosphatase Staining Kit (Sigma) following the manufacturer's recommendations. Experiments will be performed in triplicate. Von Kossa staining will be performed in duplicate wells to assess the ability of cells to mineralize the extracellular matrix and form bone nodules. Staining will be performed on cells after 21 days of culture in duplicate wells in differentiation media conditions. Cells will be fixed in neutral buffered formalin for 30 minutes, incubated with 1% aqueous silver nitrate for 15 minutes under ultraviolet light, stained with 5% sodium thiosulfate for 2 minutes, and finally counterstained with 1% Safranin O for 10 minutes. In addition, calcium concentration in the extracellular matrix will be determined via a biochemical colorimetric assay using the Calcium Reagent Set (Biotron Diagnostics, Hemet, Calif.) in duplicate wells. Experiments will be performed in triplicate.

Adipogenic:

Amnion-derived cells and MSC will be cultured in adipogenic differentiation media (Shi, Y. Y., et al., (2005) *Plast Reconstr Surg* 116, 1686-96) for 3 days (DMEM, 10% FBS, 1% pen/strep, 10 ug/ml insulin, 1 uM dexamethasone, 0.5 mM methylxanthine, 200 uM indomethacin), then change to adipocyte maintenance media for 2 more days (DMEM, 10% FBS, 1% pen/strep, 1 ug/ml insulin). Oil Red 0 staining will be performed to assess for adipogenic differentiation in duplicate wells (as indicated by the presence of intracellular lipid-filled droplets) after 5 days of culture in adipogenic media. Cells will be fixed in 10% neutral buffered formalin for 30 minutes and then incubated in 60% Oil Red 0 solution for 30 minutes at 37° C. Experiments will be performed in triplicate.

Chondrogenic:

Amnion-derived cells and MSC will be cultured in standard non differentiation conditions and then collected and resuspended at $1\times10^7$ cells/ml concentration. Ten µl droplets will then be placed onto a culture dish and allowed to adhere to substratum at 37° C. for 2 hours. Then chondrogenic media (Malladi, P., et al., (2006) *Am J Physiol Cell Physiol* 290, C1139-46) will be added carefully around cell aggregates (DMEM, 1% FBS, 1% pen/strep, 37.5 ug/ml ascorbate-2-phosphate, ITS premix (BD Biosciences), 10 ng/ml TGF-B1 (Research Diagnostics, Inc., Flanders, N.J.). Micromasses will be fixed in 4% paraformaldehyde with 4% sucrose for 15 minutes, embedded with Optimal Cutting Temperature (O.C.T.) compound. Ten µm cryosections will be mounted on slides and stained by hematoxylin and eosin and alcain blue. Immunohistochemistry will be performed as follows. Sections will be blocked at room temperature for 30 minutes and incubated with primary antibody at 4° C. overnight (anti-collagen II, Santa Cruz Biotechnology, Santa Cruz, Calif.). Followed by secondary antibody (Vector Labs, Burlingame, Calif.) incubation, 8 sections will be labeled with ABC reagent (Vector Labs, Burlingame, Calif.) for 10 minutes at room temperature. DAB (Vector Labs, Burlingame, Calif.) was applied to each section and hematoxylin will be used for counterstaining.

Skeletal Myogenic:

Amnion-derived cells and MSC will be cultured as previously described. Skeletal myogenic differentiation will be induced by culturing cells in myogenic medium (Gang, E. J., et al., (2004) *Stem Cells* 22, 617-24) (culture medium supplemented with 5% horse serum, 0.1 µM dexamethasone, and 50 µM hydrocortisone) for up to 6 weeks. Myogenic differentiation will analyzed by FACS for MyoD1, myogenin, and myosin heavy chain (MyHC). For FACS, cells will be detached and stained sequentially with primary antibodies (human-anti MyoD and anti-myogenin antibodies; Becton Dickinson) and FITC-conjugated secondary antibodies (FITC-rat anti-human IgG1; Becton Dickinson). Cells will be fixed with 2% formaldehyde until analysis with FACS. For detection of an intracellular protein MyHC, cells were permeabilized with cold methanol/PBS for 2 minutes at −20° C. before staining with primary mouse anti-myosin (fast, Sigma) and FITC-conjugated secondary antibody.

Example 18

Evaluation of Accelerated Wound Strength and Prevention of Acute Wound Failure

One object of the invention is to reduce the incidence of surgical wound failure and to optimize surgical wound outcomes by treating these acute wounds with conditioned growth media from amnion-derived cells. The focus is muscle, fascial and skin wound healing in vivo following surgical injury. Wound fibroblasts are isolated to measure the effect of soluble mediators derived from amnion-derived cells on repair fibroblast function in vitro.

Methods:

Male, Sprague-Dawley rats are used for all experiments. Ventral abdominal wall hair is shaved and the field is cleansed with alcohol and sterile water. A 6 cm full-thickness skin incision is placed 2 cm lateral to the ventral midline and a rectangular skin flap 4 cm in width is subsequently fashioned and raised through the avascular prefascial plane exposing the linea alba. In the Sham Operated rats, this skin flap is replaced and sutured using 4-0 Prolene. In the Experimental group rats, a 5 cm isolated laparotomy incision is placed through the midline of muscular layer of the abdominal wall (linea alba). The design of the ventral abdominal wall skin flap model allows laparotomy healing to occur isolated from the overlying skin wound. In the Mechanically Intact Wound group, the laparotomy is repaired with a running, 3-0 polypropylene suture using 0.3 cm suture bites and 0.5 cm progress between stitches. The suture is tied to itself at the end of the wound. Experience with this model predicts a 100% intact wound healing rate. In the Hernia Wound group, the laparotomy incision is left un-sutured. In both the Disrupted Wound and Hernia Wound models, the skin flap is sutured in place, acting as a sling to prevent the evisceration of the abdominal organs. Mortality using these models has been found to be less than 1%. Following 30 minutes of recovery on a heated pad, the rats are returned to individual cages. Food and water are provided ad libitum. All rats are observed daily and weighed weekly. Experience with these models predicts that by post operative day 28, 100% of the Intact Wound rats heal the laparotomy incision, and 100% of the Disrupted Wound rats go on to form incisional hernias.

Five rats are used at each time point to generate 5 distinct fibroblast cell lines for each of the four laparotomy wound types. Necropsies are performed 1, 7, 14, 28 and 60 days after operations. In the Disrupted Wound group, Day 0 is re-defined at the time of wound disruption on post-operative day 3. The entire ventral abdominal wall is excised from each euthanized rat, and the skin separated from the muscular layer. The peritoneal and subcutaneous (ventral) surfaces of each abdominal wall is carefully inspected for the presence of laparotomy wound disruption and herniation. An incisional hernia is defined as minimum of 2 mm of myo-fascial separation and/or obvious trans-abdominal wall herniation of abdominal contents. Biopsies are taken perpendicular to the axis of the linea alba. One biopsy from each rat is immediately snap frozen in liquid nitrogen for subsequent RNA isolation and real-time PCR measurement of collagen and integrin expression. A second adjacent biopsy from each rat is immediately fixed in 10% buffered formalin for subsequent paraffin fixation and immunohistological analysis of wound structure, fibroblast morphology, inflammatory response, angiogenesis and extracellular matrix formation. The final wound biopsy is placed in PBS (see Methods below). Primary, first pass fibroblast cell cultures are used to measure fibroblast proliferation, collagen synthesis and fibroblast populated collagen matrix compaction in vivo and following controlled patterns of mechanical strain in vitro.

Rapid gain in wound strength is tested in this model as follows: Animals are randomly assigned into one of 12 Groups (n=10 per group). In Experimental Designs 1 and 2, each of the three animal models (Sham laparotomy, Healing laparotomy and Hernia) are treated with four experimental conditions of amnion-derived cell conditioned media containing the humoral products of amnion-derived cells. (No treatment, Control amnion-derived cell media (0% conditioned), 50% amnion-derived cell CM and 100% amnion-derived cell CM). See Table 10 for Experimental Groups. 100 IU of media is delivered to the site of the laparotomy myofascial and skin incisions prior to wounding. This is defined as simple priming and establishes that this is a reliable and efficient way to deliver liquid growth media to the site of surgical incisions with a large experience in this model. Fibroblasts are isolated from healing wounds over time and assayed for the effect of amnion-derived cell media on proliferation and collagen matrix compaction in vitro.

TABLE 10

Table of Experimental Groups

| No Treatment | Unconditioned media (0% CM) | 50% CM | 100% CM |
| --- | --- | --- | --- |
| Sham | Sham | Sham | Sham |
| Wound | Wound | Wound | Wound |
| Hernia | Hernia | Hernia | Hernia |

Myofascia (laparotomy) and skin incision tensile strength rats are randomly selected and euthanized at serial timepoints following laparotomy with an overdose of Nembutal (100 mg/kg i.p.). The entire ventral abdominal wall is excised and the skin separated from the musculofascial layer. The wound healing interface is closely examined for evidence of acute failure (dehiscence) or primary incisional hernia formation, defined as a fascial defect greater than 2 mm on or after POD 7. Fascial and skin sutures are removed. Two myofascial and two skin strips in the shape of the uppercase letter "I" are taken perpendicular to the wound healing interface from each abdominal wall. A cutting template is used to mark the abdominal wall in order to minimize size variability between specimens. The abdominal wall myofascia and skin strips are labeled and stored in PBS until tensiometric mechanical analysis is performed. Biopsies are taken of the myofascial (laparotomy) and skin wounds and immediately snap frozen in liquid nitrogen for biochemical analysis or fixed in formalin for histology.

Mechanical testing of the abdominal wall fascial and skin strips is performed within 6 hours of necropsy. The sample width and thickness is measured with Digimatic calipers (Mitutoyo American Corp., Chicago, Ill.). The samples are each loaded in tension to failure, during which time the force-extension data are collected. Force extension curves are generated using an Instron Tensiometer (model 5542, Instron Corporation, Canton, Mass.) equipped with a 50 Newton static load cell set at a crosshead speed of 10 mm per minute. Samples are mounted into the load frame using pneumatic graspers, preloaded to 0.1 Newtons, and the gauge length measured between the grips. The load frame applies tensile loads perpendicular to the suture repaired wounds until mechanical tissue disruption occurs. The anatomic location of the wound failure is noted for each specimen. Force and tissue deformation data are simultaneously recorded and captured on a computer connected to the load frame via a digital interface card. Data analysis is performed using the Merlin materials testing software package (Instron Corporation, Canton, Mass.).

Data from the stretch loading is used to determine the following clinically important biomechanical properties: Breaking strength—the maximum load ($F_{max}$) at mechanical failure (Newtons); Tensile strength—the maximum stress developed in the specimen per unit area, calculated as $F_{max}$/cross sectional area ($N/mm^2$); Toughness—the energy absorbed by the specimen under tension, calculated as the entire area under the force-extension curve from the origin to mechanical rupture (Joules); Elongation—the increase in length of the tissue under a load, defined as the length of the specimen at mechanical disruption minus the original length (mm); Stiffness—the slope of the linear elastic region of the force-extension curve (N/mm).

Histological analyses of provisional matrix structure, fibroblast migration, inflammatory response and wound angiogenesis is used to compare the groups using H&E and trichrome staining The density of wound collagen formation is measured using antibodies specific for rat collagen types I and III (Chemicon International, Inc., Temecula, Calif.). Cellular infiltration into the wounds at each time-point is measured as the mean cell number from three high-powered fields by a blinded observer using a microscope. In addition, histological specimens are digitized using a UMAX Astra 1200S scanner and analyzed using the computer software application Adobe PhotoShop version 5.0. Differences in cellularity and intensity of collagen staining are compared using the Students t test (SigmaStat, Jandel).

Samples are collected from laparotomy wounds or incisional hernias from rats or humans as described previously and are placed in a sterile 50 mL conical tube (Corning, Corning N.Y.) in cooled PBS and placed on ice. Each sample is minced into small pieces and placed in a sterile 6 cm diameter Petri dish (Falcon, Franklin Lakes N.J.) containing 0.1% collagenase in PBS for 45 minutes at room temperature. During this time, tissues and cells are triturated several times using a tissue culture pipette. The solution is poured into a sterile 50 mL conical tube and centrifuged at 800 rpm for 6 minutes. The collagenase in PBS is suctioned off and the remaining cell and macerated tissue pellet is reconstituted in 15 mL complete growth medium consisting of low glucose DMEM (GIBCO, Grand Island N.Y.) supplemented with 10% newborn calf serum (GIBCO, Grand Island N.Y.), 25 µg/mL gentamicin (GIBCO, Grand Island N.Y.), and 0.375 µg/mL amphoteracin B (Sigma, St. Louis Mo.). Cells are transferred into a sterile T75 flask (Corning, Corning N.Y.) and placed into an incubator at 37° C. with 5% $CO_2$. Complete growth medium is changed every two days as soon as cells reached 10-15% confluence with a minimum of 6 colonies visible using an inverted microscope with the 5× objective. Standard cytokeratin, alpha smooth muscle actin, vimentin and van Willebrand factor staining is done to precisely characterize the cells as fibroblasts.

Once cells reach confluence, they are passaged 1:2. The medium is removed and the cell layer is washed with 10 mL of HBSS (GIBCO, Grand Island N.Y.). Cells are trypsinized with 10 mL of 0.05% trypsin with 0.53 mM EDTA (GIBCO, Grand Island N.Y.) for 4-6 minutes at 37° C. The trypsin is inhibited using 10 mL of complete growth medium. Cells are poured into a sterile 50 mL conical tube and centrifuged at 600 rpm for 5 minutes. The supernatant is removed and the cell pellet is resuspended in complete growth medium. Cells are divided into flasks to give a final passaging concentration of 1:2. Cells are trypsinized and centrifuged as above and reconstituted in 4 mL of DMEM with 40% newborn calf serum. This solution is divided into four 2 mL cryovials (Corning, Corning N.Y.), and 1 mL of cooled 20% DMSO (Fischer, Fairlawn N.J.) in DMEM is added to each vial. Vials are placed in a container with isopropyl alcohol and cooled at 1° C./min in a −80° C. freezer. When completely frozen, they are transferred to liquid nitrogen for storage.

One cryovial is removed from liquid nitrogen and quickly thawed in warm ethanol. The contents are placed in a 50 mL conical tube with 20 mL warm complete growth medium and centrifuged at 600 rpm for 5 minutes. The supernatant is removed and the cellular pellet is reconstituted in 15 mL warm complete growth medium. The cells are plated in a T75 flask. A MIT colorimetric assay is used to access viability of the fibroblasts by measuring their mitochondrial activity.

In vitro protein matrices (FPCL's) fashioned with collagen, fibrin, and fibronectin are used. Extracellular matrix protein lattices are prepared as described by the manufacturer (Upstate Biotechnology, Lake Placid, N.Y.). The gels are incubated for 24 hours at 4° C. The fibroblasts are counted and their cell number adjusted to $1×10^5$ cells/ml. One hundred thousand first passage-cultured fibroblasts are added to each prefabricated 3.5 cm lattice. The lattices are incubated at 37° C. with 5% $CO_2$ and the extent of gel contraction is measured every 24 hours for 5 days. The gels are digitally imaged each day and contraction measurements calculated using Sigma Scan software (Jandel Scientific, Corte Madera, Calif.). Alternatively, FPCL's fabricated from rat tail collagen is used for corroborative data. This assay runs from 30 minutes to several hours and allows determination of the response of the cells to various functional inhibitors. Measurement of gel contraction are performed overtime. Collagen gels are detached from petri dishes, treated with 2.5% FCS or 2 u/ml thrombin, and the diameter of the gel measured at perpendicular axis at various times. One function that is evaluated is the role of MAP kinases on collagen contraction.

To further characterize the fascial fibroblasts to explain the effects seen from the animal experiments, a series of tests are performed on the wound fascial and dermal fibroblast cultures. These include collagen types I and II gene expression using quantitative RT-PCR on extracted RNA; measurement of tissue collagen levels of biopsies of the wound healing interface using the Sircol collagen assay method (Acurate Chemical and Scientific Corp., Westburg, N.Y.); measurement of fibroblast, alpha-1 and beta-1 integrin expression to assure that any reduction in FPCL contraction was not due to poor migration and reduced fibroblast function; and immunohistochemistry to evaluate alpha-smooth muscle action, and Proliferating Cell Nuclear Antigen (PCNA) using specific monoclonal antibodies for PCNA and alph-SMA (Sant Cruz Biotechnology, Santa Cruz, Calif.).

Statistical analyses is as follows: For each experiment, a factorial design with balanced sample sizes in each group ensures that the main effect, independent variables in each experiment can be isolated with appropriate statistical analysis. Outcome variables are compared using parametric (continuous variables) and non-parametric (proportions) ANOVA. Nested ANOVA designs are used to incorporate the main effect variables from each experiment into a single analysis. If the F ratio for the overall ANOVA is significant, post hoc comparisons of individual group means are conducted via t-prime tests of least-squares means for each comparison. Inherent in this approach is a Bonferonni correction of the significance level when making multiple pairwise comparisons. The ANOVA calculations are performed using the general linear models (GLM) algorithm from the Statistical Analysis System (SAS, Carey, N.C.), which accounts for unbalanced sample sizes, should they occur. Post-hoc pairwise testing is conducted using the lsmeans option with the GLM procedure. The correlations between the measured variables and if significant covariance is observed between variables for a given experiment are examined, analysis of covariance (ANCOVA) is performed as appropriate. A 5% level of significance is considered statistically significant.

Example 19

Use of Amnion-Derived Cells, Conditioned Media, Cell Lysates, and Cell Products for Rapid Early Wound Closure of Thermal Injuries Outcome and rehabilitation of thermal injuries rely on early burn wound excision and rapid wound closure. The speed of wound closure with a serviceable integument or integument substitute is the key to an improvement in survival. Providing novel approaches that will facilitate early, rapid wound closure, while minimizing long-term scarring, is an object of the present invention.

Established in vitro, animal models, and clinical patients are used to evaluate the use of amnion-derived cells for early, rapid wound closure of partial-thickness and full-thickness burns. In addition to thermal injuries, experiments are done with established models for chemical, electrical, and cold injuries.

It is theorized that amnion-derived cells can differentiate into mesodermal and ectodermal cells. Thus, it may be possible that use of such cells will provide early and permanent closure of the burn wound. Since presently, the prolonged time the wound is in the inflammatory phase is the known variable leading to proliferative scarring, it is expected that early, permanent closure of the burn wound would result in decreased scarring and, thus, increased function.

Methods:

Three animal models of partial-thickness and full-thickness thermal injuries are used. The three models are different because the first mimics partial-thickness healing by epithelialization in approximately three weeks while the second and third mimic full-thickness healing by contraction and epithelialization and can remain unhealed for up to eight weeks. The last two models have been histologically compared to the human granulating wound. The difference in the last two full-thickness wounds is the host. One group is a normal rat with an intact immune system, while the other is an athymic "nude" rat which is devoid of T-lymphocytes.

Partial-thickness burn injury: Forty female Hartley strain guinea pigs weighing 350 to 450 grams are used throughout this part of the experiment. Under Nembutal anesthesia (35 mg/kg administered intraperitoneally), the animals' backs are shaved and depilated. A uniform scald burn over 10% of the body surface is performed at 75° C. for 10 seconds. Guinea pigs are used for this model because of their lack of an estrus (hair) cycle, and the ability to develop uniform partial-thickness injuries in them. Animals are caged individually and fed food and water ad libitum.

At 24 hours, the animals are reanesthetized and the partial-thickness eschar gently abraded. The 40 animals are divided into four groups of 10 animals each. The groups are as follows: Group 1-guinea pigs burned, abraded, and left untreated as controls; Group II—burned, abraded and treated with non-conditioned media on day 1 (day of abrasion) and day 7; Group III—burned, abraded and treated with amnion-derived cell conditioned media on day 1 and day 7; Group IV—burned, abraded, and treated with a suspension of amnion-derived cells over the entire burn, and dressed with Adaptic and bulky dressing. The outer dressing is gently removed every five days or prn. The animals are premedicated with buprinorphine (0.1 mg/kg), anesthetized with halothane inhalation and burn wound biopsies are obtained on a weekly basis until the time of healing. The biopsy specimens are sectioned and stained, and the hair follicles are counted microscopically and expressed as the number per high power field. Additionally, histological analyses of the healing skin is done. Gross observations are made and photographically documented for the quality of healing and hair distribution.

Full-Thickness Burn Injury (Normal Rat):

Fifty male Sprague-Dawley rats weighing 300-350 grams are acclimatized for one week prior to use. Under intraperitoneal Nembutal anesthesia, the rat dorsum is shaved and depilated. A full-thickness dorsal burn measuring 30 square cms is created by immersion in actively boiling water. Seven mL of Ringer's lactate by subcutaneous injection is given to each rat to prevent dehydration. Animals are individually caged and given food and water ad libitum. Five days after burning, the eschar is be excised from anesthetized animals resulting in a granulating wound. Histological characterization of this wound with comparison to a human granulating wound has previously been performed (Robson M C, et al., J Surg Res 16: 299-306, 1974). The rats are divided into five groups of 10 animals each and treated as follows: Group I receive no wound treatment and serve as controls; Group II receives treatment with nonconditioned media on day 0 (day of escharectomy) and on day 7; Group III receives treatment with amnion-derived cell conditioned media on day 0 and day 7; Group IV is treated with a suspension of amnion-derived cells and dressed with Adaptic and a bulky dressing. The dressing is changed every five days or prn. Group V is treated with an extracellular matrix seeded with amnion-derived cells and dressed as in Group IV. Groups I-III animals' wounds are left exposed. Any dried exudates are atraumatically removed prior to any wound tracings or biopsies. Every 72 hours for rats in Groups I-III or whenever dressings require changing in Groups IV and V the rats are premedicated with buprinorphine (0.1 mg/kg), anesthetized with halothane inhalation, and the outlines of their wounds are traced onto acetate sheets. Area calculations are performed using digital planimetry. Serial measurements are plotted against time. For each animal's data, a Gompertz equation is fitted (typical $r2=0.85$). Using this curve the wound half-life is estimated. Comparison between groups is performed using life table analysis and the Wilcoxon rank test. The statistical analyses is performed using the SAS (SAS/STAT Guide for Personal Computers, Version 6 Edition, Cary, N.C., 1987, p 1028) and BMDP (BMDP Statistical Software, Inc. 1988). From the best fit curves for the individual wounds, the number of days required for 25%, 50%, and 75% healing of the original wounds is calculated. Randomized wound biopsy sites are obtained from reanesthetized rats on days 5, 10, 15, 20, and 25 post escharectomy (or days 10, 15, 20, 25, and 30 post burn) and placed in appropriate preservative solutions for histological studies.

Full-thickness burn injury (immunologically impaired rat): Fifty outbred, congenitally athymic "nude" rats are purchased commercially (Harlan Sprague Dawley, Inc., Indianapolis, Ind.). All animals are male and weigh between 250 and 300 grams. Because of their immune defect, the animals are housed in pathogen-free barrier facilities, in cages with sealed air filters, animal isolators, laminar flow units, and laminar flow rooms. All supplies such as food, water, bedding etc. are sterilized to prevent infection. Procedures recommended in the Guide for the Care and Use of the Nude Mouse in Biomedical Research (Institute of Laboratory Animal Resources) are used at all times. Persons handling the rats wear caps, masks, sterile gowns, sterile gloves, and shoe covers. All operations on "nude" rats are carried out under intraperitoneal Nembutal anesthesia, 35 mg/kg body weight, using aseptic surgical techniques. Operations are performed under a unidirectional airflow biological hood. Surgical instruments are sterilized by autoclaving and surgical sites are prepared with povidone iodine solution. The 50 animals are divided into five groups of 10 each. The anesthesia, analgesia, procedures, wound treatments, and measurements are identical to the intact rat model described above. Handling of the tracings, planimetry, and statistics are also the same as previously described.

In vitro fibroblast-populated collagen lattice: The fibroblasts are prepared as previously described by Kuhn, et al (Kuhn M A, et al., Internat J Surg Invest 2: 467-474, 2001). The collagen lattices are prepared from type I rat tail collagen (acetic acid extracted) as recommended by the manufacturer (Upstate Biotechnology, Lake Placid, N.Y.) (11). Undiluted collagen (1 ml) is placed in 35 mm culture dishes (Falcon 1008) and evenly spread. The dishes are placed in an ammonia vapor chamber for 3 minutes to solidify. Sterile distilled water (5 ml) is added to the culture dishes, allowed to stand for one hour, and then aspirated. This is repeated four times to remove excess ammonia and the collagen lattices are incubated for 24 hours at 4° C. PBS with 1.0% serum is added to replace the final aspirate. An 18 gauge needle is used to detach the collagen gel lattices from the surface of the culture dishes so that they are loose and suspended in saline. A total of 30 collagen lattices are prepared to allow quintruplicate measurements based on 5 treatment groups plus an untreated control. To form the FPCLs, all saline is aspirated from the 35 mm culture dishes containing the lattices. Two ml of $2 \times 10^5$ fibroblasts/ml are placed on the surface of each of the prefabricated collagen gel lattices. FPCLs are divided into six groups as follows: Group I is kept as a control with no treatment; Group II receives nonconditioned media; Group III receives amnion-derived cell conditioned media; Group IV receives a suspension of amnion-derived cells; Group V is covered with an extracellular matrix; and Group VI is covered with an extracellular matrix seeded with amnion-derived cells. The FPCLs are incubated at 37° C., 5% carbon dioxide. The amount of gel contraction is measured every 24 hours for 5 days.

Acetate overlays are used for tracing the area of the gels. Gels are performed in quintruplicate (5 gels) for the fibroblast line established and measurements are calculated using digital planimetry and Sigma Scan software (Jandel Scientific, Corte Madera, Calif.). Each collagen gel area measurement is converted to reflect percentage of area remaining over time and subsequently percentage of gel contraction. A one-way analysis of variance is used to determine significant differences among groups. When a difference is identified, a Tukey's Test (all pairwise multiple comparison test) is used to delineate the differences. Sigma Stat statistical software is used for data analysis. In addition, the 24 hour FPCLs are examined microscopically and photographed. One of the gels is evaluated for fibroblast viability on day 5 utilizing Trypan blue exclusion assay. Another gel is included for cell number spectrophometrically as a function of mitochondrial activity using the MTT method. After exposure to test agents, the five day suspension cultures are reincubated and exposed to [4,5-dimethylthiazol-2-yl]-2,5-diphenyl tetrazolium bromide or MTT. Mitochondrial dehydrogenases from viable fibroblasts cleave the tetrazolium ring, yielding purple formazan crystals. These are dissolved in an acidified isopropanol resulting in a purple solution which is spectrophometrically measured. An increase or decrease in cell number results in a concomitant change in the amount of formazan formed, indicating any degree of toxicity of the applied test material.

Example 20

Differentiation of Amnion-Derived Cells to Early Pancreatic Progenitor Cells

All four pancreatic endocrine cell types that comprise the pancreatic islet develop by progressive differentiation from a common pancreatic progenitor cell. This common pancreatic progenitor cell expresses the PDX1 gene early in its developmental ontogeny and later, expression of this gene serves as an early distinguishable cell marker of pancreatic differentiation. Once this early pancreatic progenitor cell is generated and/or propagated in vitro, it may potentially give rise to all four endocrine cell types comprising the mature pancreatic islet.

Developmentally, the endocrine and exocrine pancreatic cells are derived from outgrowths of cuboidal epithelium from the foregut endoderm. This three-dimensional architecture is thought to be important in the development and expression of both exocrine and endocrine cell types. In an attempt to duplicate this environment, a novel culture condition that preferentially supports and maintains the spheroids of amnion-derived cell in suspension culture is used. Briefly, cells are grown as a monolayer, than treated with proteinase XXIII to obtain single cells or small clusters of cells. Detection of PDX1 protein expression (cytoplasmic and perinuclear) first occurs in cells present in buds on the outer-most surface of the amnion-derived cell spheroids. Immunocytochemical techniques show that these cells also express CD29 protein. These buds of pancreatic progenitor cells resemble the cells prominently observed in adult pancreatic duct cell differentiation (Bonner_Weir, S., et al., Proceedings of the National Academy of Sciences of the United States of America, 2000. 97 (14): p. 7999-8004., Jones, E. M. and N. Sarvetnick, Horm Metab Res, 1997. 29 (6): p. 308-10; Ramiya, V. K., et al., Nature Medicine, 2000. 6 (3): p. 278-82]

The cells are then plated on a substrate or in a matrix that maintains the three-dimensional structure of the spheroids but promotes protein expression of cytoplasmic PDX1. After several days, the cells are supplemented with factors that promote nuclear translocation of PDX1 protein in a small proportion of the differentiating cells. In the presence of factor/cell culture conditions that promote nuclear localization of PDX1 protein, large numbers of these buds appear on the majority of the amnion-derived cell spheroids cultured in suspension. Amnion-derived cells may also be cultured in the presence of an extracellular matrix in the presence of the

Example 21

Determination of Cells Expressing Islet Cell Proteins

Cells fixed in 4% buffered PFA and stored in 1×PBS containing 0.02% sodium azide, are rinsed with 1×PBS. The cells are then blocked for nonspecific binding with 5% BSA in Calcium and Magnesium-Free Phosphate Buffered Saline (CMF-PBS) for 30 minutes and permeabilized with PBS-TX (CMF-PBS/0.3% Triton-X-100). Staining for nuclear antigens is performed using an additional high salt treatment (0.3M NaCl, 20 mM Tris-HCl pH 7.2, 0.1% Tween-20, 0.1% Triton-X-100) and overnight incubation with the primary antibody. All antibodies are diluted in 5% BSA in PBS-TX, unless otherwise noted. Pancreatic transcription factors are identified by staining the cells with anti-PDX1 (rabbit polyclonal, 1:2000, C.V. Wright), anti-Nkx2.2 (mouse monoclonal 1:100, T. Jessell), anti-Nkx6.1 (mouse monoclonal, 1:8000, T. Jessell), and anti-HB9 (mouse monoclonal, 1:30, T. Jessell). Endocrine cells are identified by staining with anti-Insulin (1:2000, Linco 4012-01), anti-Proinsulin, (1:400, Novacastra Peninsula, IHC-7165) and anti-Somatostatin (1:2000, Peninsula, IHC-8001). Secondary antibodies used include: Fluorescein isothyocyanate (FITC) (1:200), Indocarbocyanine (Cy3) (1:1000) and Indodicarbocyanine (Cy5) (1:400)-conjugated donkey anti-mouse, rabbit and guinea pig IgG (Jackson ImmunoResearch, ML grade). Cell nuclei are visualized by DAPI fluorescence as part of the Vectashield mounting medium (Vector, H1200). Cells are analyzed with a Nikon Eclipse E2000U fluorescence/DIC inverted microscope equipped with Autoquant 3-D Imaging software and an Olympus FV300 FluoView Confocal Laser Scanning Microscope.

Example 22

Transplantation Studies—In Vivo Co-Culture of Amnion-Derived Cell with Embryonic Islet Progenitor Cells Under the Kidney Capsule Three experimental groups are used to determine if the dorsal pancreatic bud from embryonic day 12.5 (e12.5) mice promotes the differentiation of PDX1 protein-expressing amnion-derived cells:

A. Group 1—12 immuno-compromised mice, 4 months of age, are transplanted with $10^6$ PDX1 protein-expressing cells and two e12.5 dorsal pancreatic explants under the kidney capsule. Three mice are sacrificed for analysis every second week (time points: 2, 4, 6, and 8 weeks after transplantation).

B. Group 2 (control)—12 immuno-compromised mice, 4 months of age, are transplanted with $10^6$ freshly isolated amnion-derived cells and two e12.5 dorsal pancreatic explants under the kidney capsule. Three mice are sacrificed for analysis every second week (time points: 2, 4, 6, and 8 weeks after transplantation).

C. Group 3 (control)—12 immuno-compromised mice, 4 months of age, two e12.5 dorsal pancreatic explants under the kidney capsule. Three mice are sacrificed for analysis every second week (time points: 2, 4, 6, and 8 weeks after transplantation).

Dorsal pancreatic buds are manually dissected from the foregut of each embryo directly and/or incubated with 0.2 Wunsch U/ml Liberase Blendzyme-3 (Roche, 11814176) and 0.15 mg/ml DNase I at 37° C. for 15 min. The enzymatic dissociation is immediately terminated by the addition of an equal volume of 1×PBS containing 10% (w/v) BSA. The dorsal pancreatic buds are rinsed with HBSS at 4° C. and briefly triturated using a 200 µl pipet tip. The epithelium is stripped manually from the surrounding mesenchyme and transferred into HBSS at 4° C. prior to transplantation.

Mouse and human amnion-derived cells are placed under the kidney capsule of immuno-compromised mice to prevent immuno-rejection of the grafted cells over the course of the experiment. At each time point, three mice are sacrificed, the transplanted cells isolated and fixed in 4% PFA. The tissue is then soaked in a series of increasing concentrations of sucrose, embedded with OCT and sectioned. Cyro-sections (10 µm) are analyzed for the co-expression of human nuclear antigen protein and specific islet endocrine cell marker proteins. These markers include: pro-insulin, C-peptide, glucagon, somatostatin, Nkx2.2, Pax6, Nkx6.1 and PDX1 proteins.

Example 23

Transplantation Studies—In Vivo Co-Culture of Amnion-Derived Cells with Embryonic Islet Progenitor Cells in the Mammary Gland Three experimental groups are used to determine if the dorsal pancreatic bud from embryonic day 12.5 (e12.5) mice promotes the differentiation of PDX1 protein-expressing amnion-derived cells:

A. Group 1—12 immuno-compromised mice, 4 months of age, are transplanted with $10^6$ PDX1 protein-expressing cells and two e12.5 dorsal pancreatic explants in the mammary gland. Three mice are sacrificed for analysis every second week (time points: 2, 4, 6, and 8 weeks after transplantation).

B. Group 2 (control)—12 immuno-compromised mice, 4 months of age, are transplanted with $10^6$ freshly isolated amnion-derived cells and two e12.5 dorsal pancreatic explants in the mammary gland. Three mice are sacrificed for analysis every second week (time points: 2, 4, 6, and 8 weeks after transplantation).

C. Group 3 (control)—12 immuno-compromised mice, 4 months of age, two e12.5 dorsal pancreatic explants in the mammary gland. Three mice are sacrificed for analysis every second week (time points: 2, 4, 6, and 8 weeks after transplantation).

Dorsal pancreatic buds are manually dissected from the foregut of each embryo directly and/or incubated with 0.2 Wunsch U/ml Liberase Blendzyme-3 (Roche, 11814176) and 0.15 mg/ml DNase I at 37° C. for 15 min. The enzymatic dissociation is immediately terminated by the addition of an equal volume of 1×PBS containing 10% (w/v) BSA. The dorsal pancreatic buds are rinsed with HBSS at 4° C. and briefly triturated using a 200 µl pipet tip. The epithelium is stripped manually from the surrounding mesenchyme and transferred into HBSS at 4° C. prior to transplantation.

Mouse and human amnion-derived cells are placed in the mammary gland of immuno-compromised nude mice to prevent immuno-rejection of the grafted cells over the course of the experiment. At each time point, three mice are sacrificed, the transplanted cells isolated and fixed in 4% PFA. The tissue is then soaked in a series of increasing concentrations of sucrose, embedded with OCT and sectioned. Cyro-sections (10 µm) are analyzed for the co-expression of human nuclear antigen protein and specific islet endocrine cell marker proteins. These markers include: pro-insulin, C-peptide, glucagon, somatostatin, Nkx2.2, Pax6, Nkx6.1 and PDX1 proteins.

Example 24

Transplantation of Undifferentiated Amnion-Derived Cells, Semi-Differentiated Amnion-Derived Cells Expressing Peri-Nuclear PDX1 and Amnion-Derived Cells Stably Expressing the Nuclear PDX1 Fusion Protein into Immuno-Comprised Mice Transplantation of undifferentiated amnion-derived cells, semi-differentiated amnion-derived cells expressing peri-nuclear PDX1 and amnion-derived cells stably expressing the nuclear PDX1 fusion protein into non-diabetic immuno-compromised mice was done to determine if the mammary gland is a permissive transplantation site that will maintain the morphological characteristics of the differentiating cells and expression of the PDX1 protein.

Fifteen immuno-compromised mice (Hilltop Labs) were transplanted as follows: Group 1: Control Group, Reduced Factor Matrigel Injected, 5 mice; Group 2: Factor Induced PDX1 expressing amnion-derived cells; 5 mice; Group 3: amnion-derived cells infected with Lentiviral PDX1 fusion protein; 5 mice.

Mice were maintained after transplantation in normal housing conditions for 31 days. The mammary gland tissue containing the transplanted cells was subsequently removed, fixed, embedded with O.C.T. and frozen at −80 C. Additional control samples from the opposite (non-transplanted) mammary gland were also excised as a control. Sections will be analyzed for PDX1, Proinsulin and insulin expression.

Example 25

Further Transplantation Studies

PDX1 protein-expressing cells are also transplanted into the portal vein, spleen and mammary gland using non-diabetic immuno-compromised mice. Differentiating amnion-derived cells as above are initially transplanted with differentiating mouse e12 dorsal pancreatic buds to determine if they can respond to the same factors as early embryonic pancreatic epithelial cells and generate islet-like cells. All tissues transplanted with PDX1 protein-expressing cells are removed two and six weeks following transplantation, fixed, cryopreserved and sectioned. Tissue sections are stained with PDX1 anti-sera, Pro-insulin, C-Peptide, Glucagon and Somatostatin antibodies. Human nuclear antigen immunostaining will be used to verify the origin of cells expressing endocrine cell markers in the rat pancreas.

Example 26

Restoration of Normoglycemia in STZ-Induced Diabetic NOD-Immun-Compromised Mice

Further experiments are conducted to restore normoglycemia in STZ-induced diabetic NOD-immuno-compromised mice. Mice exhibiting initial blood glucose levels over 400 ng/dl are included in the experiment. Insulin therapy (Linbit) is administered to the animals after the initial blood glucose determination but prior to cell transplantation. This allows for the initial engraftment of amnion-derived cells in a normoglycemic environment. Initial evidence of human C-peptide expression will be determined using a human C-Peptide RIA or ELISA assay. Once detection of human C-peptide is confirmed, insulin therapy is discontinued and the blood glucose monitored every third day. If the differentiated cells are able to restore normoglycemia in the STZ-induced diabetic mice, the transplanted cells will be removed forty to sixty days after transplantation and the mice evaluated daily for reversion to the blood glucose levels (>400 ng/dl) previously observed.

Example 27

Factor-Priming Experiments

In one experiment, the pancreas of a mouse is primed with factors to promote differentiation of resident pancreatic cells into functional islets. These factors include any individual or combination of the following factors: FGF(s), Forskolin, Follistatin, angiogenic factors, glucocorticoid family members, Insulin, EGF, EGF-like factors, Heparin, Nicotinamide, SHh antagonists, HGF, GLP-1 analogs, between 1 and 20 mM Glucose, divalent cations.

In another experiment the pancreas of a mouse is primed with factors to promote the regeneration of transplanted undifferentiated amnion-derived cells to this site and to allow differentiation. Undifferentiated amnion-derived cells may be freshly isolated cells (not cultured) treated with factors to ensure endoderm differentiation (SHh antagonists, spheroid growth).

In another experiment the pancreas of a mouse is primed with factors to promote the regeneration of transplanted partially differentiated amnion-derived cells to this site and to allow further differentiation. Partially differentiated means the amnion-derived cells have been cultured in vitro in any condition described herein.

In another experiment the pancreas of a mouse is primed with other factors and then the following cells are transplanted: Co-culture of undifferentiated or partially differentiated amnion-derived cells with differentiating embryonic pancreatic or non-pancreatic tissue (epithelium, mesenchyme, islets, ducts, exocrine cells) or differentiating or pre-differentiated non-embryonic heterologous (donor) or autologous (self) tissue (epithelium, mesenchyme, islets, ducts, exocrine cells, etc.). These cells will provide active factors and/or the biological niche necessary for the differentiation of undifferentiated or partially differentiated amnion-derived cells to pancreatic cells. These factors and/or niche may also promote the molecular organization of the cells so the cells mature and function as pancreatic islet-like cells.

In another experiment the pancreas is primed with proprietary factor combinations and then transplanted with a co-culture of undifferentiated or partially differentiated amnion-derived cells with differentiating embryonic pancreatic or non-pancreatic tissue (epithelium, mesenchyme, islets, ducts, exocrine cells) or differentiating or pre-differentiated non-embryonic heterologous (donor) or autologous (self) tissue (epithelium, mesenchyme, islets, ducts, exocrine cells, etc.). These cells will provide active factors and/or the biological niche necessary for the differentiation of undifferentiated or partially differentiated amnion-derived cells to pancreatic cells. These factors and/or niche may also promote the molecular organization of the cells so the cells mature and function as pancreatic islet-like cells.

Another experiment is transplanting undifferentiated or partially differentiated amnion-derived cells that have been primed in vitro (not primed at the site of transplantation in vivo) directly into pancreas. In another experiment, the cells are transplanted subcutaneously, into liver, mammary gland, kidney capsule, spleen or any other site in which the cells are able to engraft.

Another experiment is transplanting undifferentiated or partially differentiated amnion-derived cells via intravenous injection to pancreas that has been injured surgically or chemically then primed or not primed with the factors listed above. In this experiment the cells will "home" to the inflammatory site and integrate with the resident cells.

Another experiment is the use of undifferentiated, partially differentiated or functionally differentiated amnion-derived cells transplanted into the pancreas or any other tissue (i.e. subcutaneously, into liver, mammary gland, kidney capsule, spleen or any other site in which the cells are able to engraft) (or introduced by intravenous injection) to induce immune tolerance in a patient with an autoimmune disease (for example, diabetes). Synchronized cell differentiation may occur between the transplanted amnion-derived cells alone and/or with cells in the patient (i.e. damaged islets, beta cells, etc). The amnion-derived cells may provide HLA antigens that will protect cells associated with them from the immune system.

Explants will be evaluated for human pancreatic islet progenitor cells. Undifferentiated and partially differentiated amnion-derived cells will differentiate into cells expressing islet cell-specific protein markers of differentiation. Analysis will include immunocytochemistry and GFP expression of pre-labeled cells.

The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification.

What is claimed is:

1. A composition comprising:
   a) a first component consisting of a substantially purified population of cultured amnion-derived cells, wherein the substantially purified population of cultured amnion-derived cells are made by a method comprising the steps of i) obtaining a placenta and isolating an amnion from the placenta, ii) enzymatically releasing amnion-derived epithelial cells from the amnion, iii) collecting the released amnion-derived epithelial cells, and iv) culturing the collected amnion-derived epithelial cells of step (iii) in basal culture medium that is supplemented with human serum albumin and, optionally, further supplemented with recombinant human protein factors capable of stimulating proliferation of the cultured amnion-derived epithelial cells; and b) a second component consisting of a matrix selected from the group consisting of a polyglycolic acid, a polyanhydride, a polyorthoester, and a polylactic acid.

2. The composition of claim 1 wherein the matrix is selected from the group consisting of a gel, an extracellular matrix, and a 3-dimensional scaffold.

3. The composition of claim 2 wherein the gel is selected from the group consisting of an ointment, a salve, and a cream, and a gel matrix.

* * * * *